(12) United States Patent
Jenkins et al.

(10) Patent No.: US 11,612,413 B2
(45) Date of Patent: Mar. 28, 2023

(54) TELESCOPING ATRIAL SEPTUM NEEDLE

(71) Applicant: Merit Medical Systems, Inc., South Jordan, UT (US)

(72) Inventors: Richard Jenkins, Kennett Square, PA (US); Christopher A. Heine, Schwenksville, PA (US); Shaun Lessik, West Chester, PA (US); Krista Killion, Philadelphia, PA (US); Thomas Chapman, Wilmington, DE (US)

(73) Assignee: Merit Medical Systems, Inc., South Jordan, UT (US)

( * ) Notice: Subject to any disclaimer, the term of this patent is extended or adjusted under 35 U.S.C. 154(b) by 699 days.

(21) Appl. No.: 16/598,159

(22) Filed: Oct. 10, 2019

(65) Prior Publication Data
US 2020/0113597 A1    Apr. 16, 2020

Related U.S. Application Data

(60) Provisional application No. 62/743,915, filed on Oct. 10, 2018.

(51) Int. Cl.
*A61B 17/34* (2006.01)
*A61M 29/00* (2006.01)
(Continued)

(52) U.S. Cl.
CPC ......... *A61B 17/3421* (2013.01); *A61M 29/00* (2013.01); *A61B 2017/00243* (2013.01);
(Continued)

(58) Field of Classification Search
CPC ...... A61B 17/3421; A61B 2017/00243; A61B 2017/00349; A61B 2017/00991; A61B 2017/3425; A61B 17/3496; A61B 2017/00247; A61B 2017/00309; A61B 2017/00331; A61B 2017/00455; A61B 2017/3443; A61B 2090/08021;
(Continued)

(56) References Cited

U.S. PATENT DOCUMENTS 6,238,355 B1    5/2001  Daum
6,572,593 B1 *  6/2003  Daum ................ A61B 17/3417
                                                          604/164.13
(Continued)

FOREIGN PATENT DOCUMENTS

| CN | 201719367 | 1/2011 |
|----|-----------|--------|
| CN | 201758652 | 3/2011 |
| WO | 2006083729 | 8/2016 |

OTHER PUBLICATIONS

International Search Report and Written Opinion dated Jan. 28, 2020 for PCT/US2019/055554.
European Search Report dated May 11, 2022 for EP19871017.0.

*Primary Examiner* — Richard G Louis
(74) *Attorney, Agent, or Firm* — Dorsey & Whitney LLP

(57) ABSTRACT

Devices used to provide transseptal access are disclosed. The devices may comprise at least one cannula, a needle, and a handle. The cannula and the needle may be configured to be inserted through a dilator while not damaging a lumen wall of the dilator. The handle may be configured to lock the needle in a retracted position. The devices may be configured to telescopically advance the needle through an atrial septum.

21 Claims, 45 Drawing Sheets

(51) Int. Cl.
*A61B 17/00* (2006.01)
*A61M 29/02* (2006.01)

(52) U.S. Cl.
CPC ........... *A61B 2017/00349* (2013.01); *A61B 2017/00991* (2013.01); *A61B 2017/3425* (2013.01); *A61M 2029/025* (2013.01)

(58) Field of Classification Search
CPC ....... A61B 2090/0811; A61B 17/3478; A61M 29/00; A61M 2029/025; A61M 25/0084; A61M 2025/0089; A61M 2025/0175
See application file for complete search history.

(56) References Cited

U.S. PATENT DOCUMENTS

| | | |
|---|---|---|
| 8,214,014 B2 | 7/2012 | Pacheco |
| 2003/0233115 A1* | 12/2003 | Eversull ............ A61M 25/1002 606/194 |
| 2004/0054377 A1* | 3/2004 | Foster ................. A61B 17/221 606/167 |
| 2007/0043388 A1* | 2/2007 | Greenwood .......... A61M 29/00 606/193 |
| 2007/0270741 A1 | 11/2007 | Hassett et al. |
| 2009/0125097 A1* | 5/2009 | Bruszewski ............... A61F 2/07 623/1.23 |
| 2009/0163942 A1* | 6/2009 | Cuevas ............. A61M 16/0472 606/167 |
| 2010/0160863 A1* | 6/2010 | Heuser ............. A61M 25/0662 604/164.1 |
| 2012/0239069 A1 | 9/2012 | Benscoter et al. |
| 2013/0304036 A1 | 11/2013 | Kimmel et al. |
| 2015/0045769 A1 | 2/2015 | Cabrera Aquino et al. |
| 2015/0173794 A1 | 6/2015 | Kurth et al. |
| 2018/0085027 A1 | 3/2018 | Kimmel et al. |

* cited by examiner

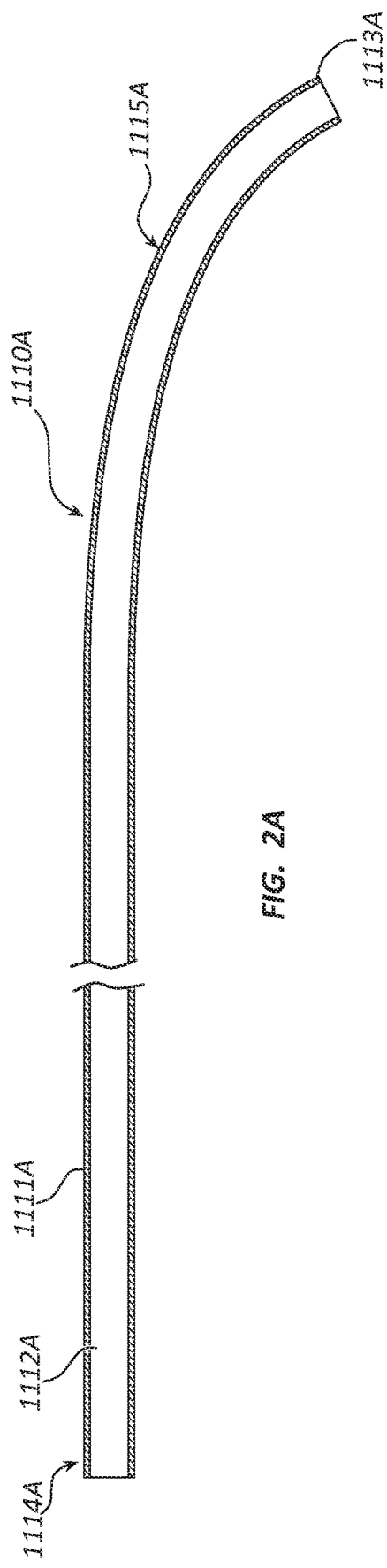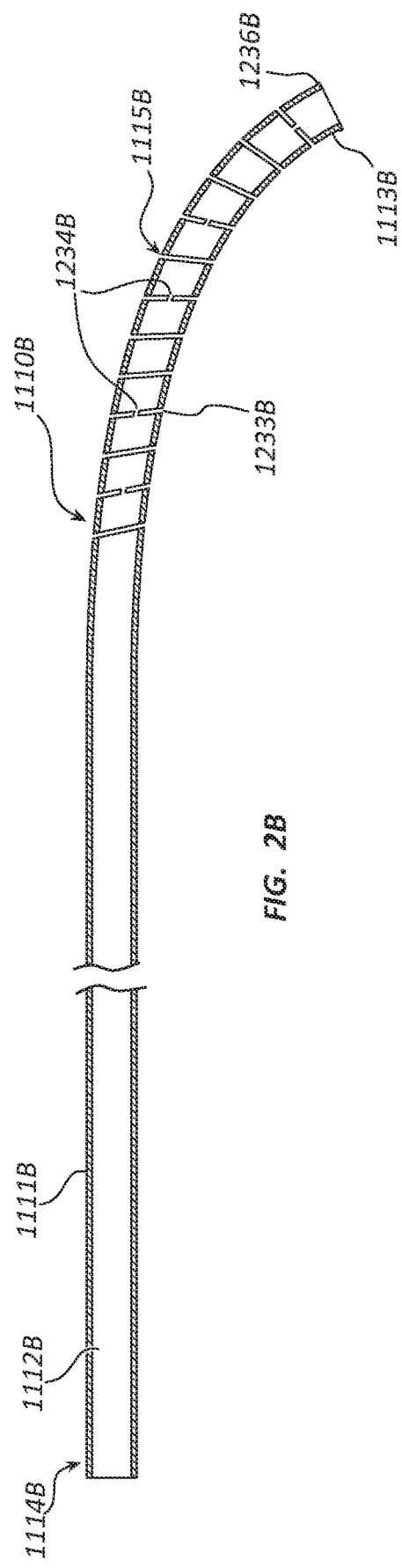
FIG. 2A
FIG. 2B

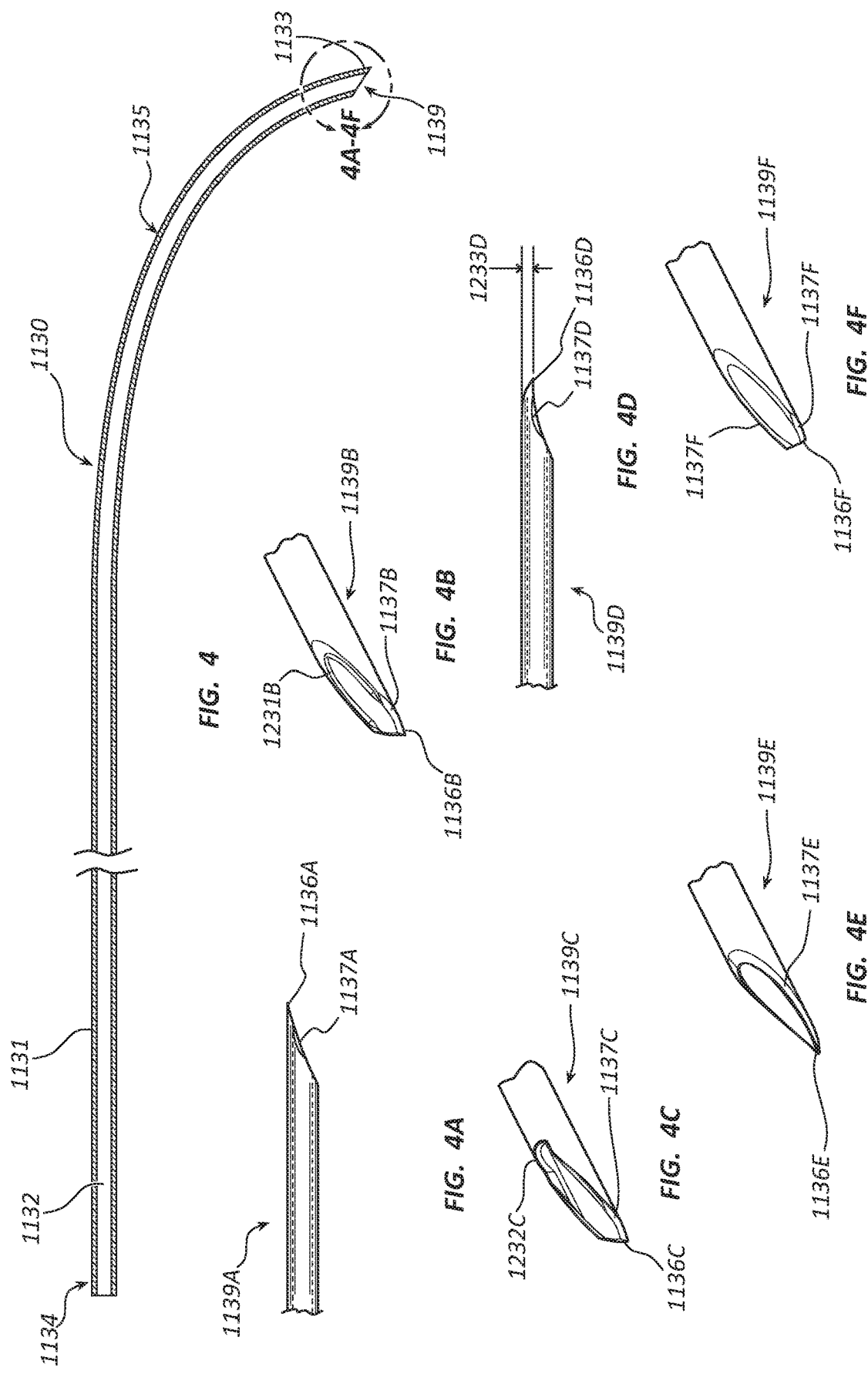

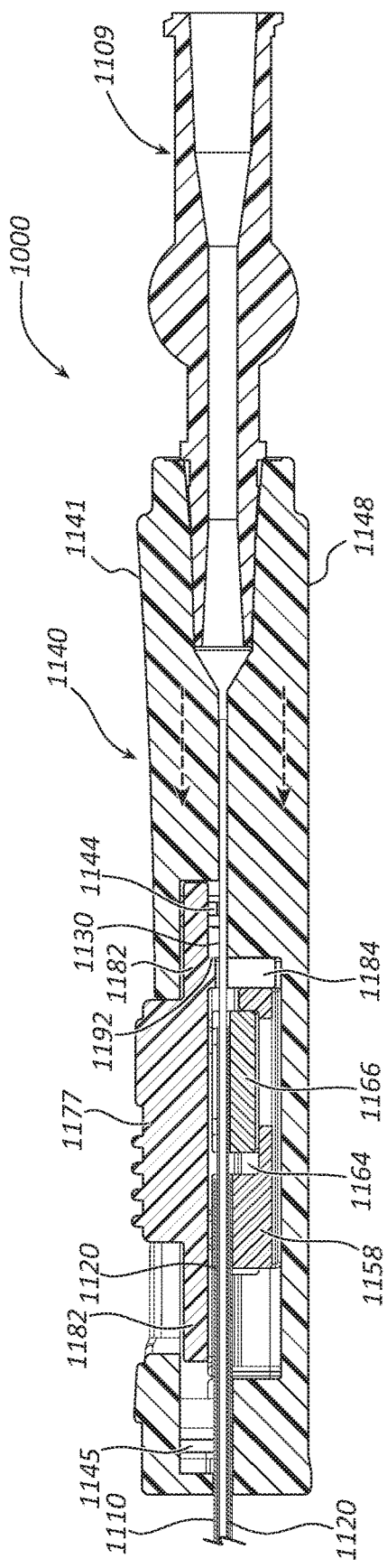
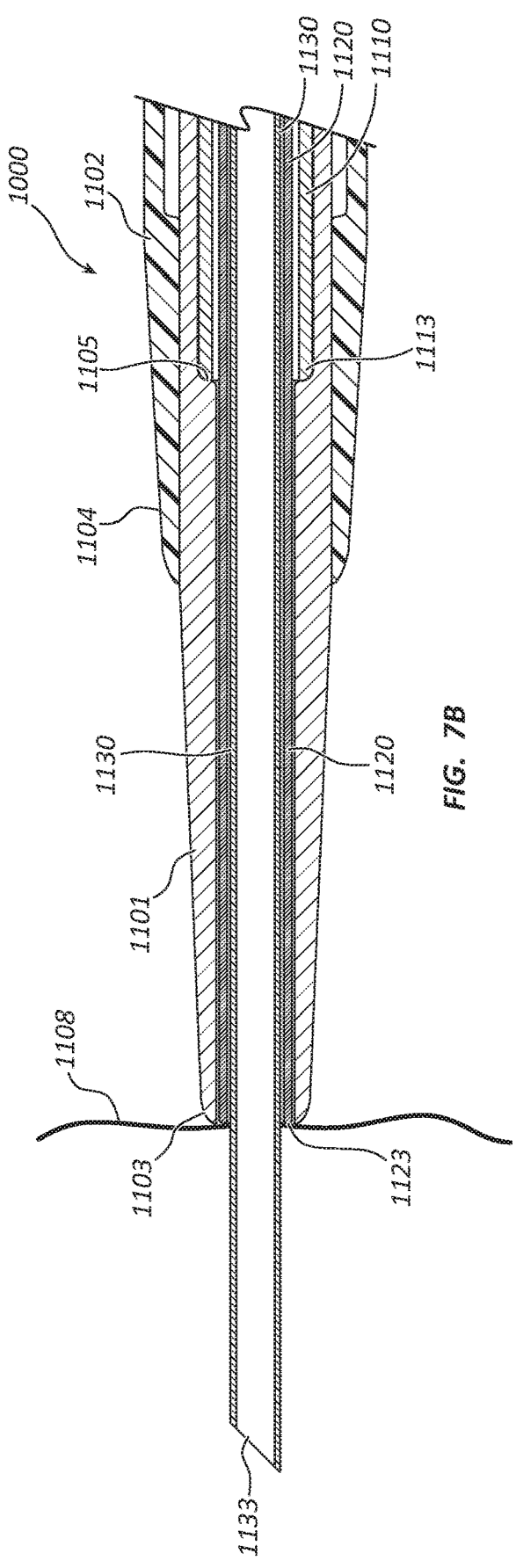
FIG. 7A
FIG. 7B

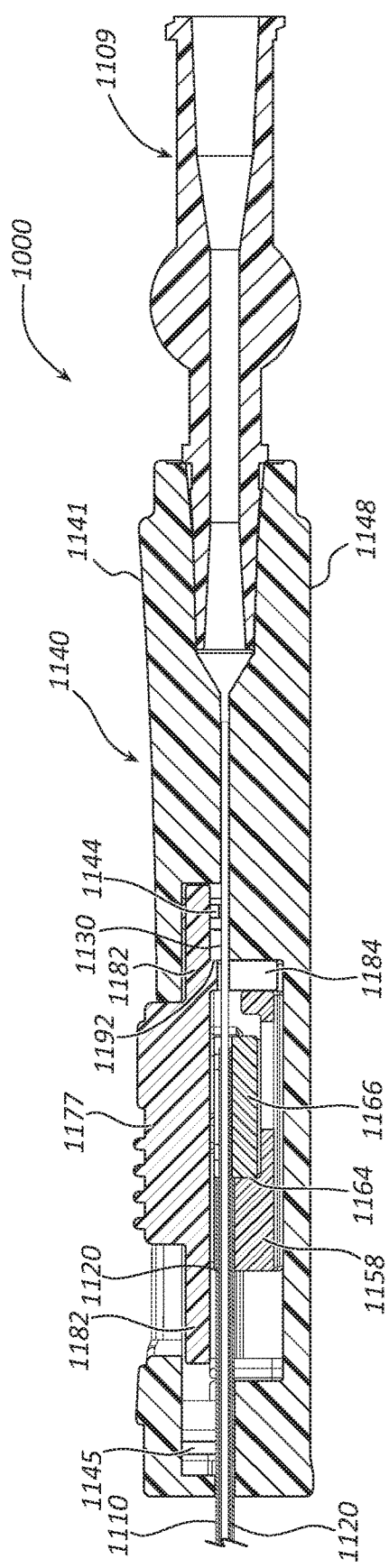
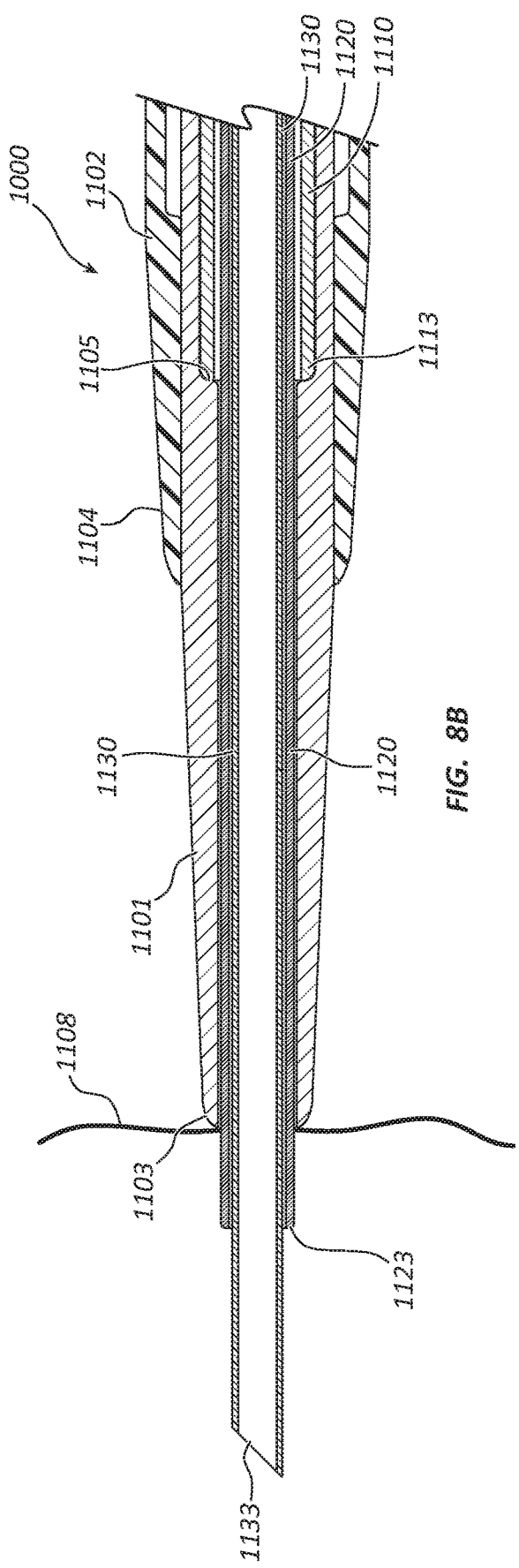
FIG. 8A
FIG. 8B

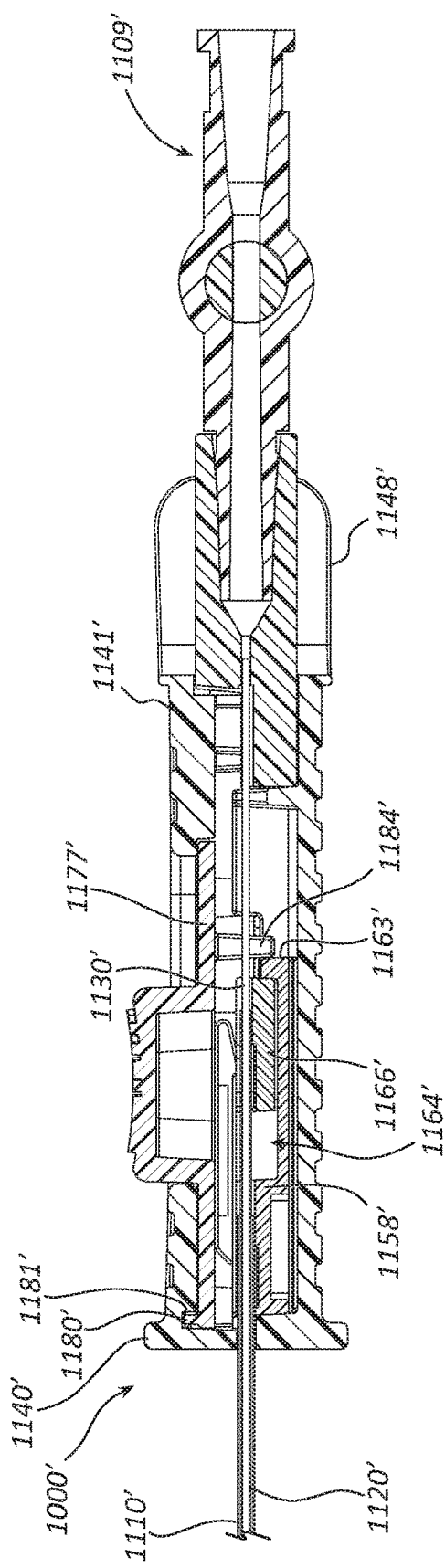
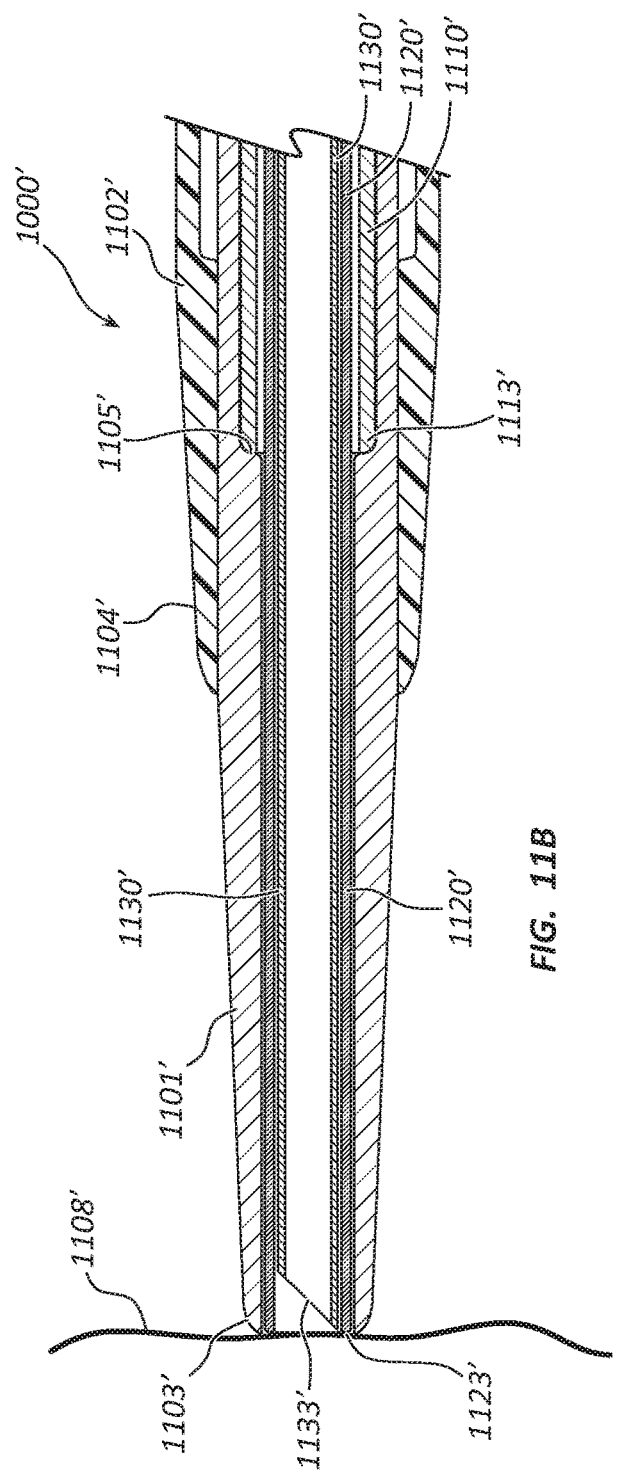
FIG. 11A
FIG. 11B

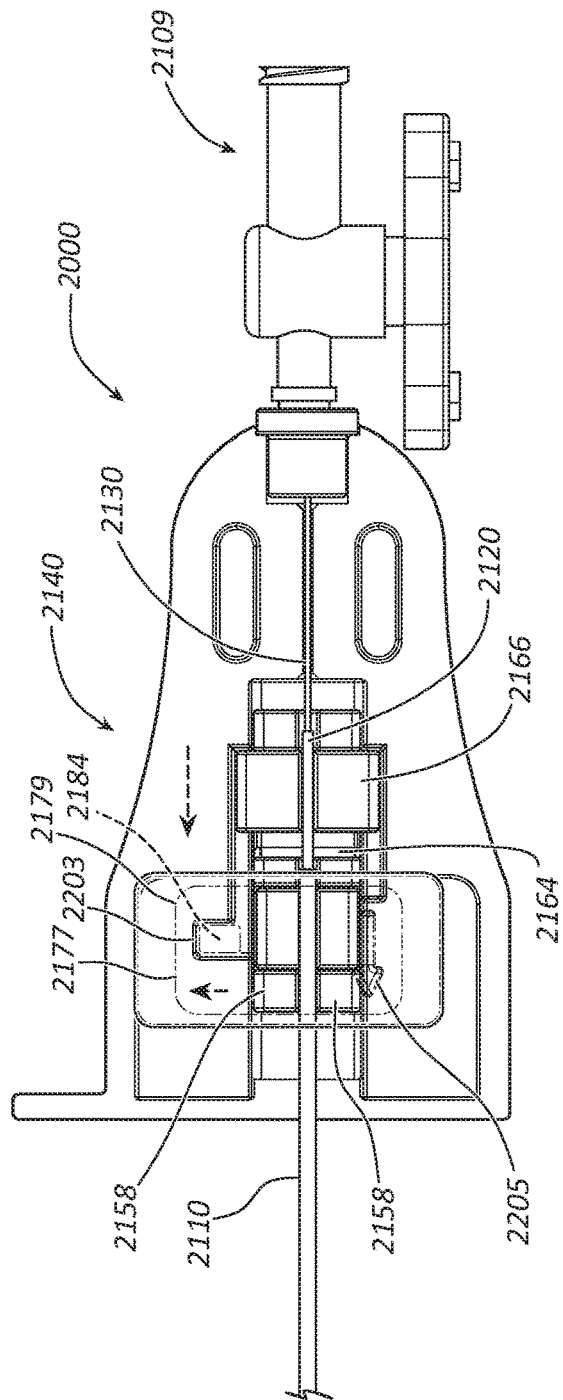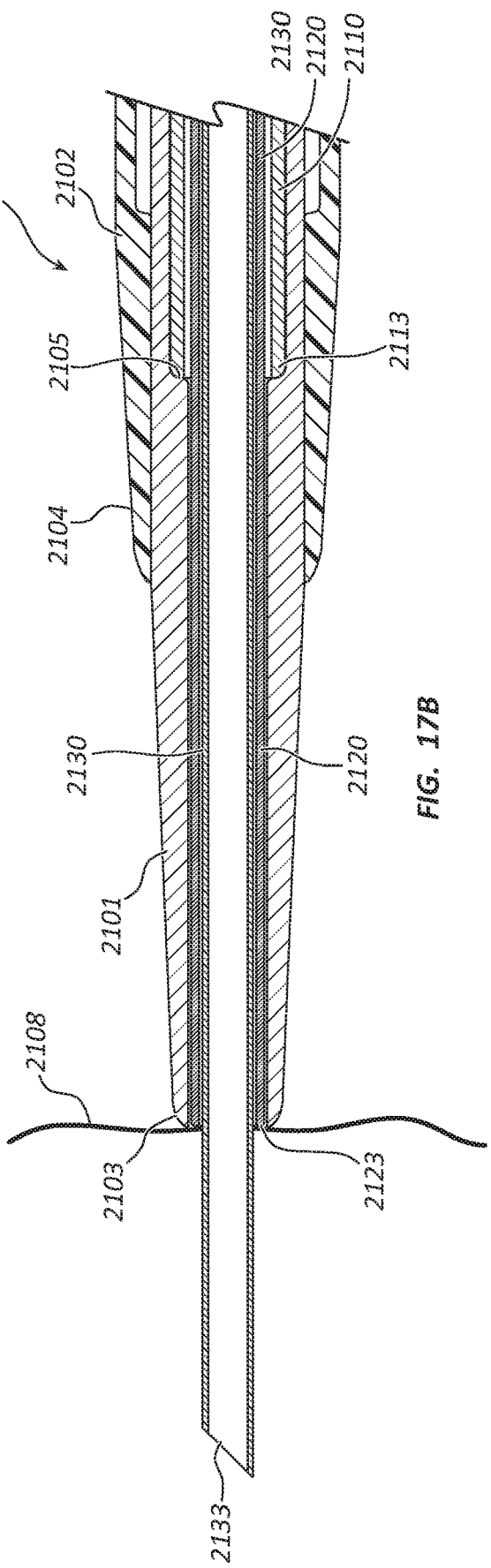
FIG. 17A
FIG. 17B

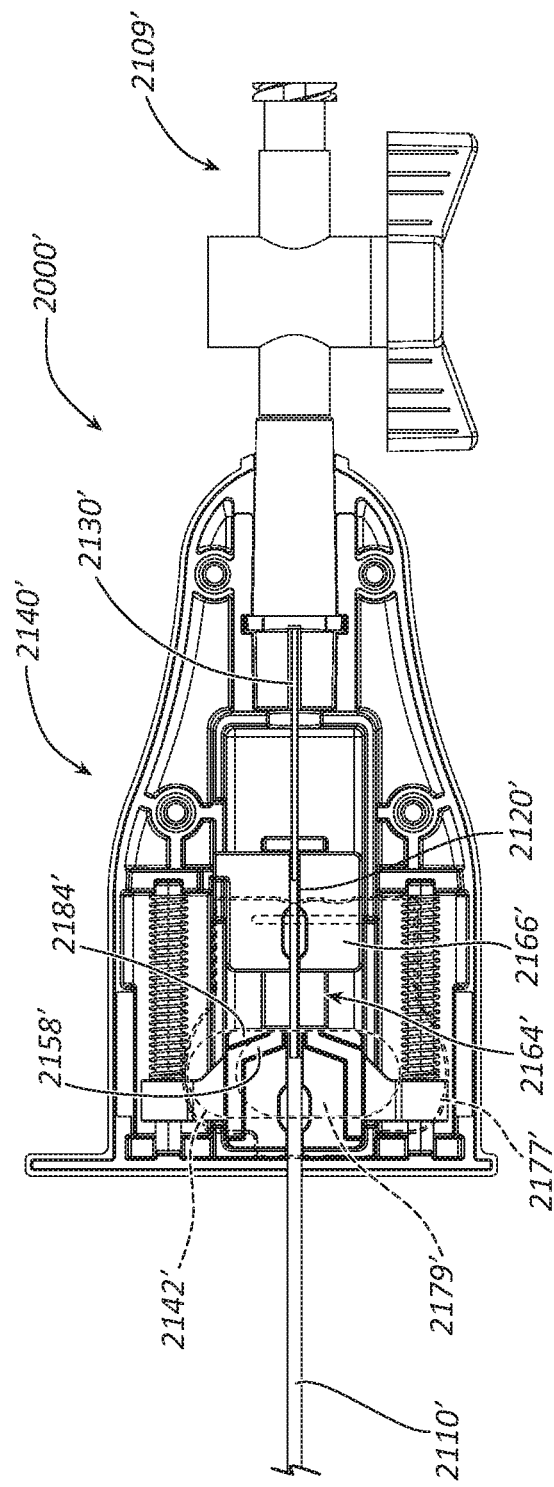
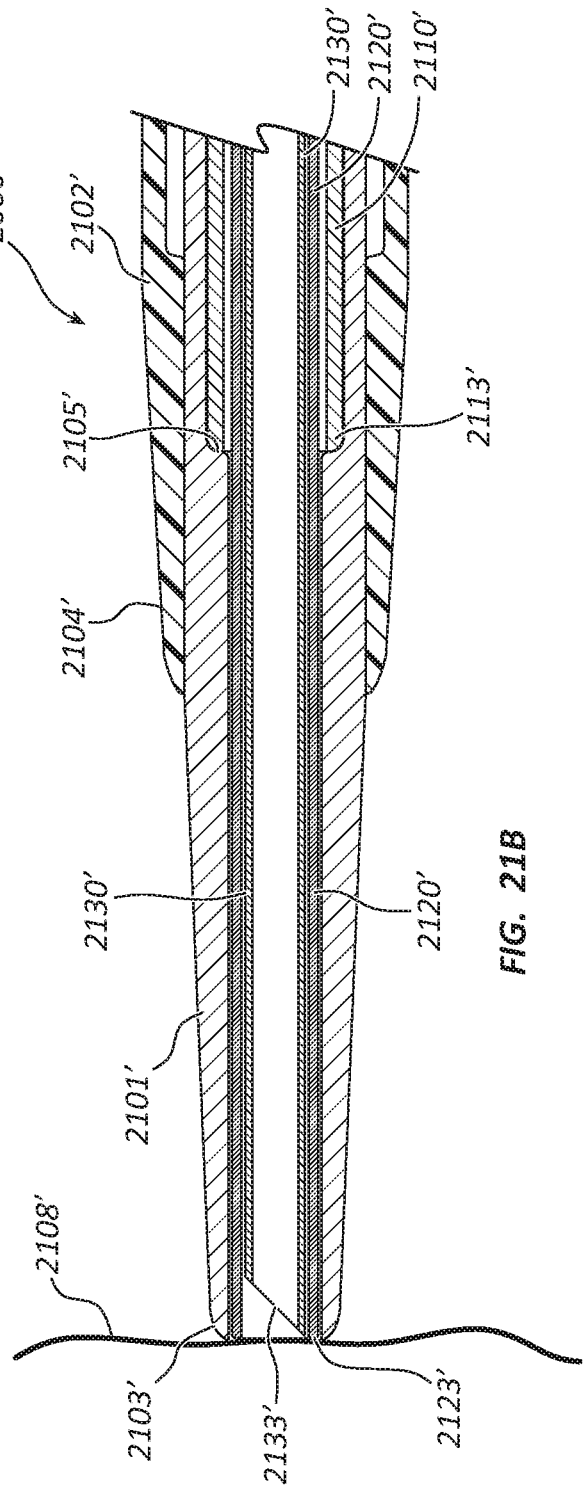
FIG. 21A
FIG. 21B

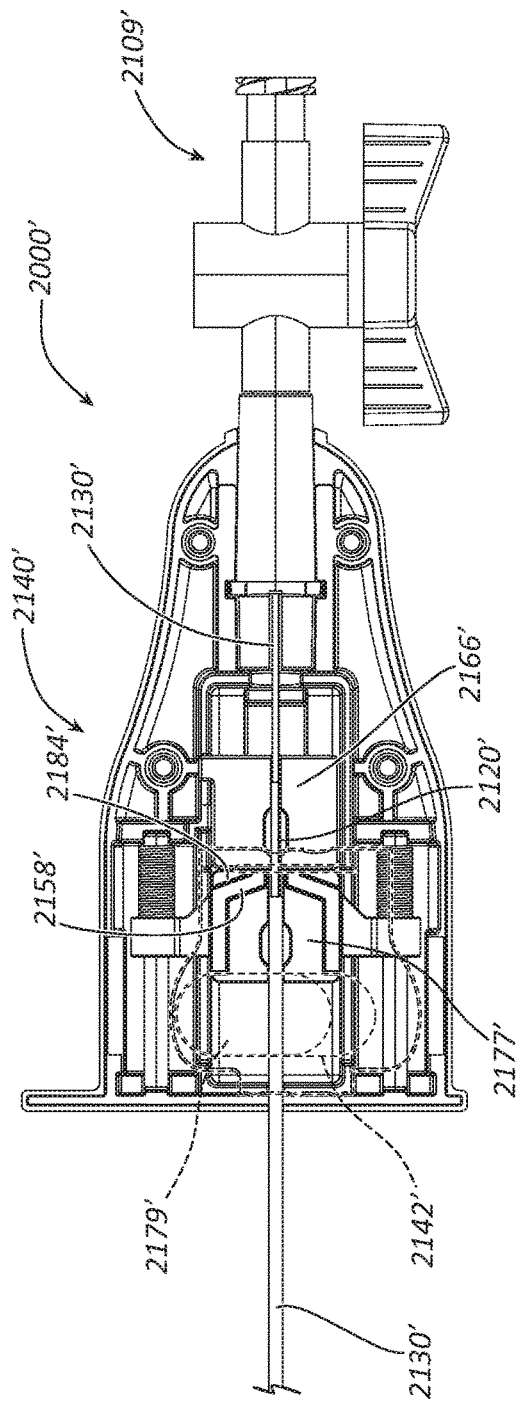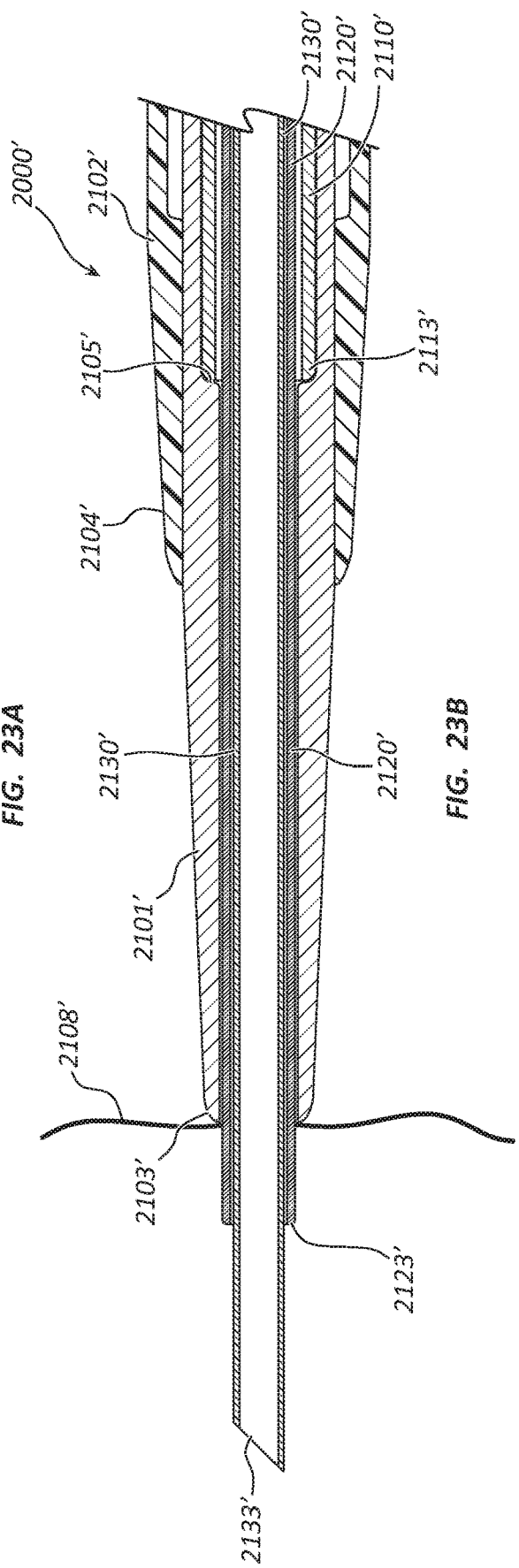
FIG. 23A
FIG. 23B

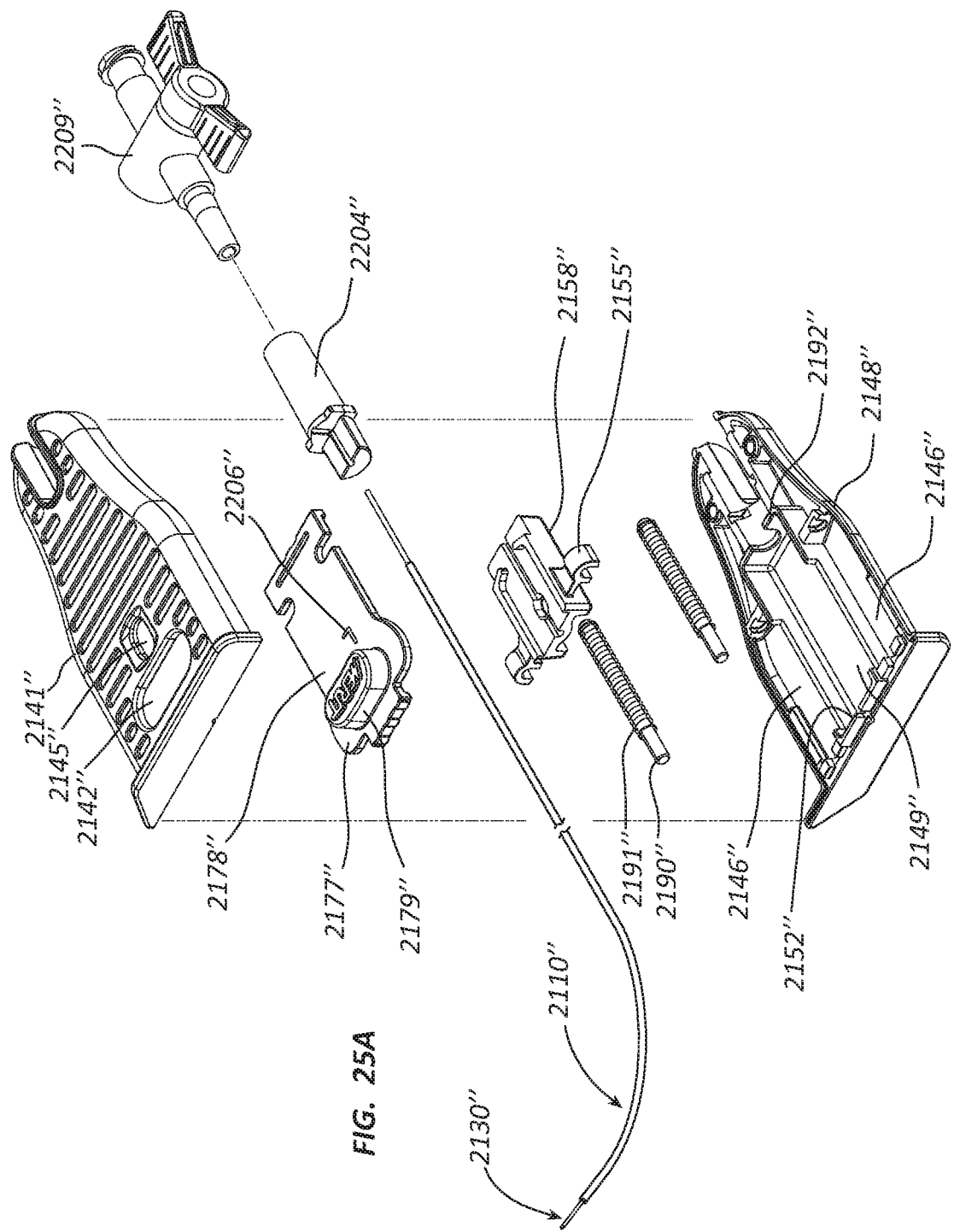

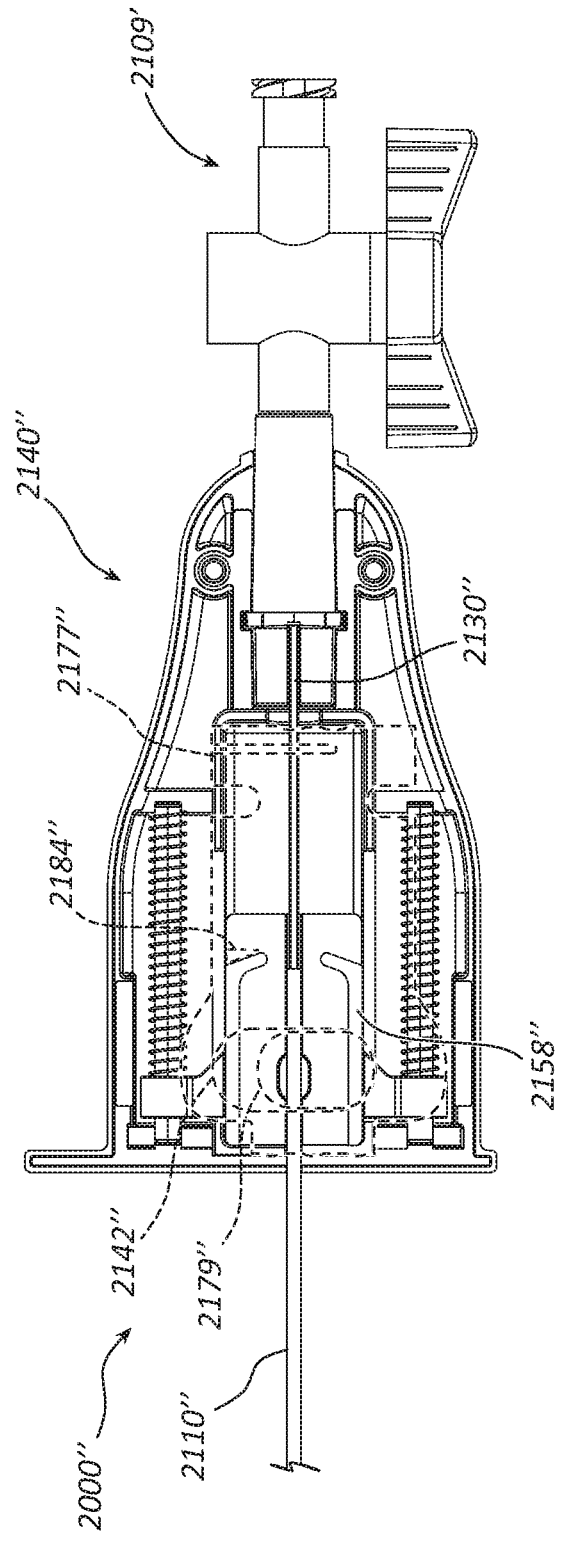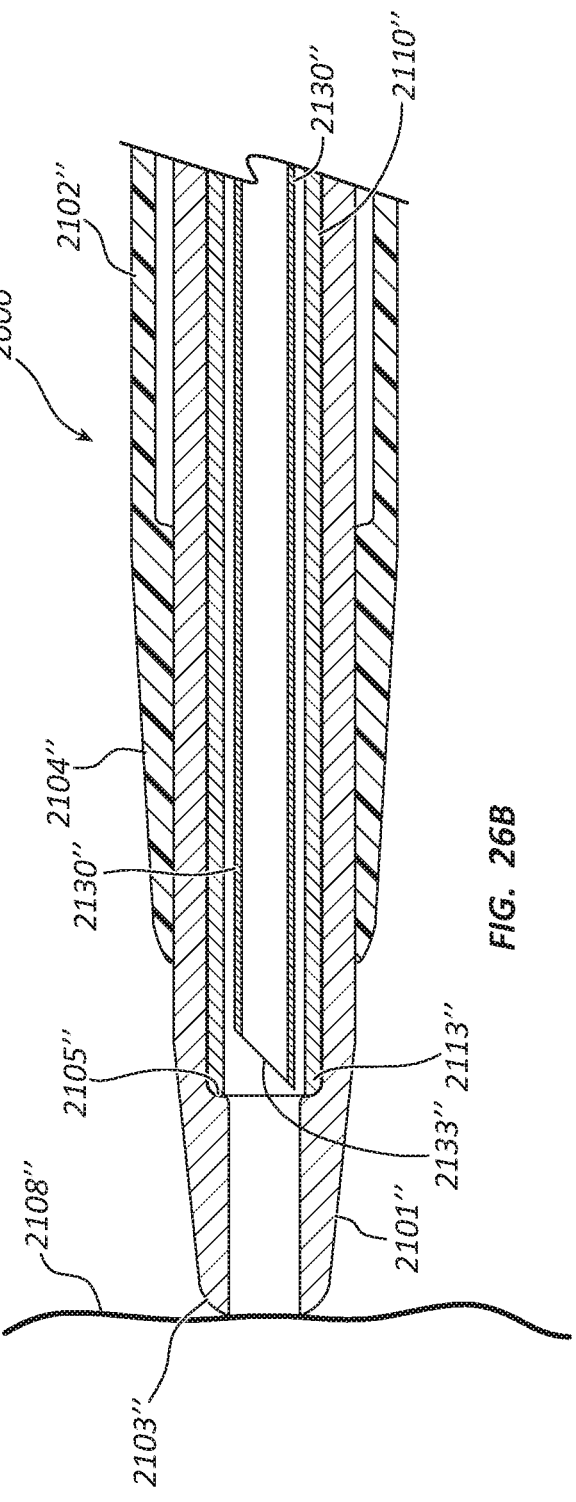
FIG. 26A
FIG. 26B

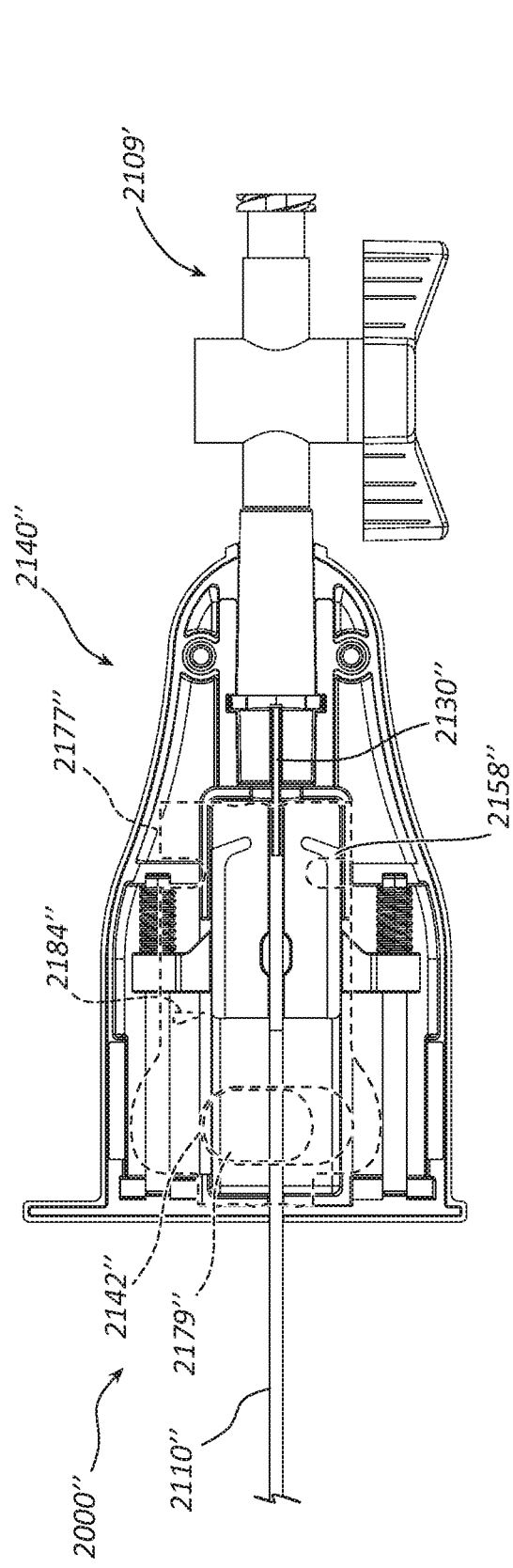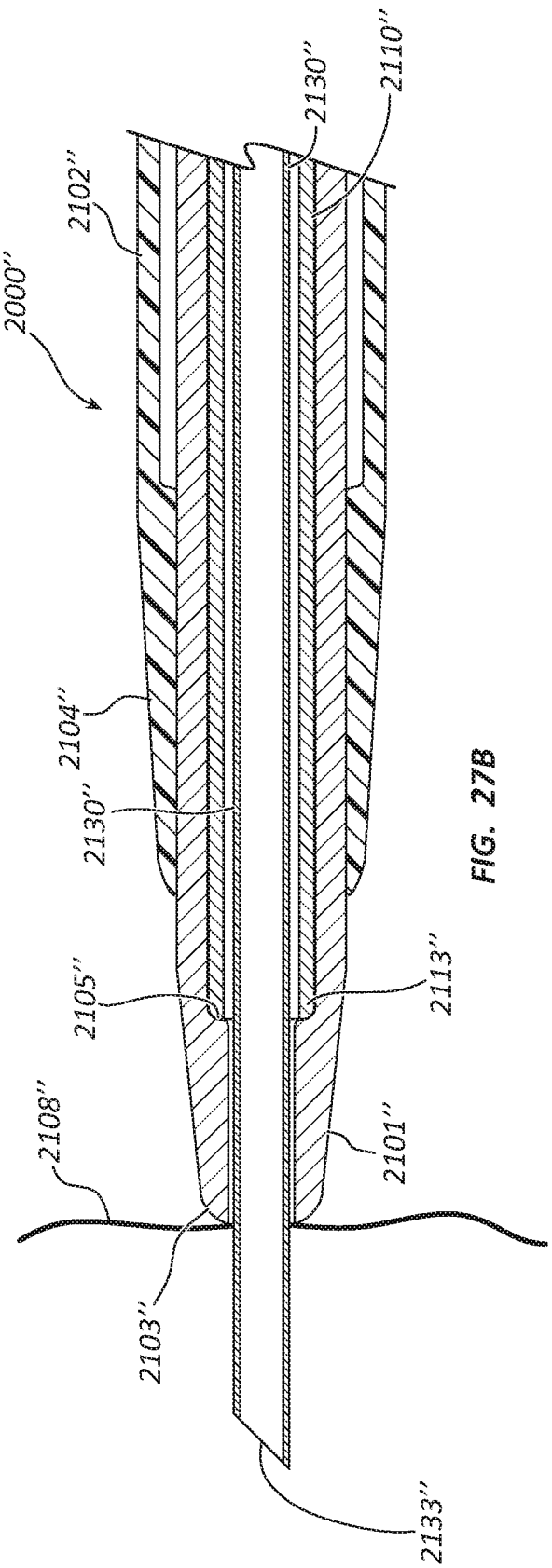
FIG. 27B

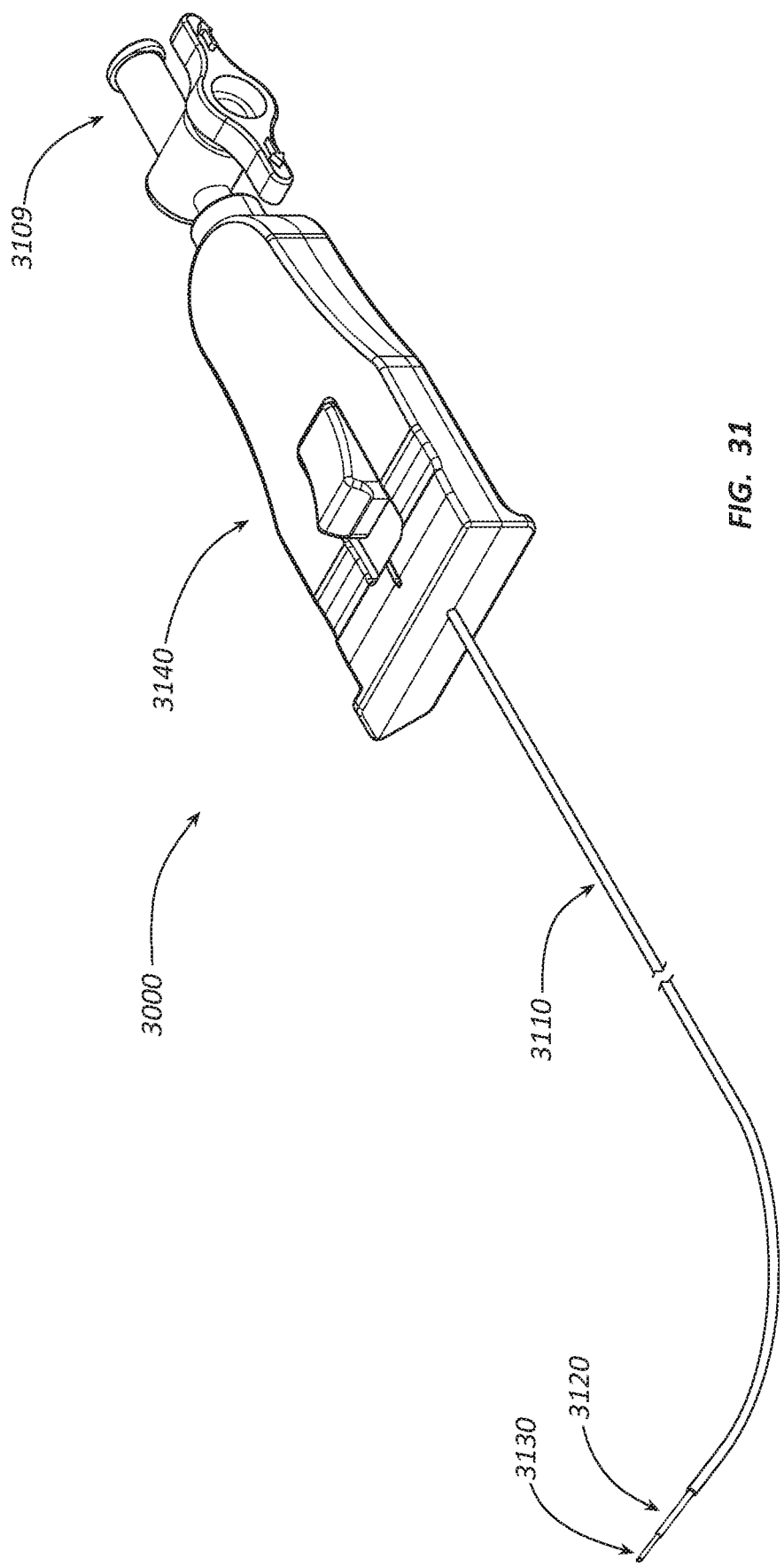

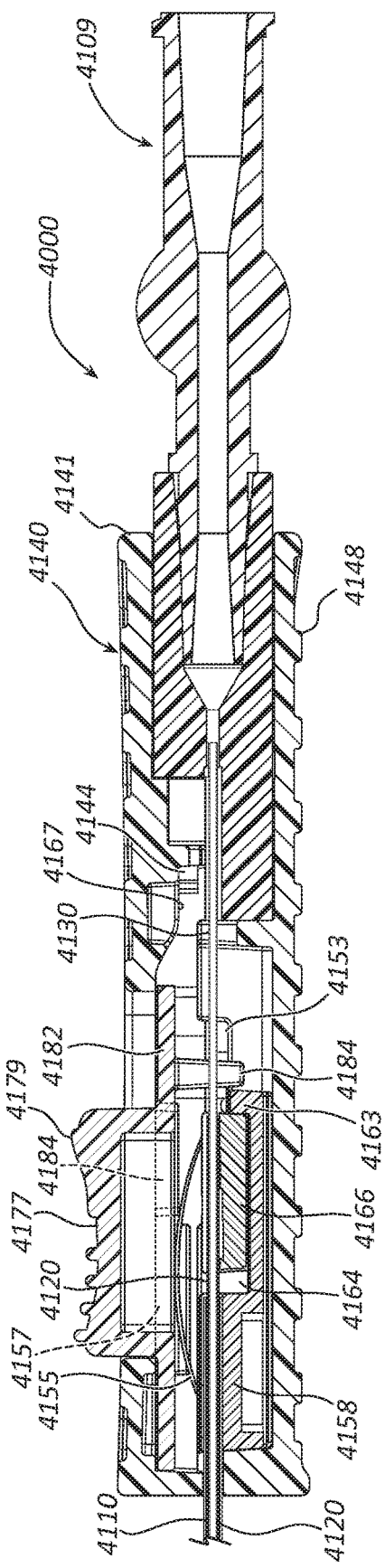
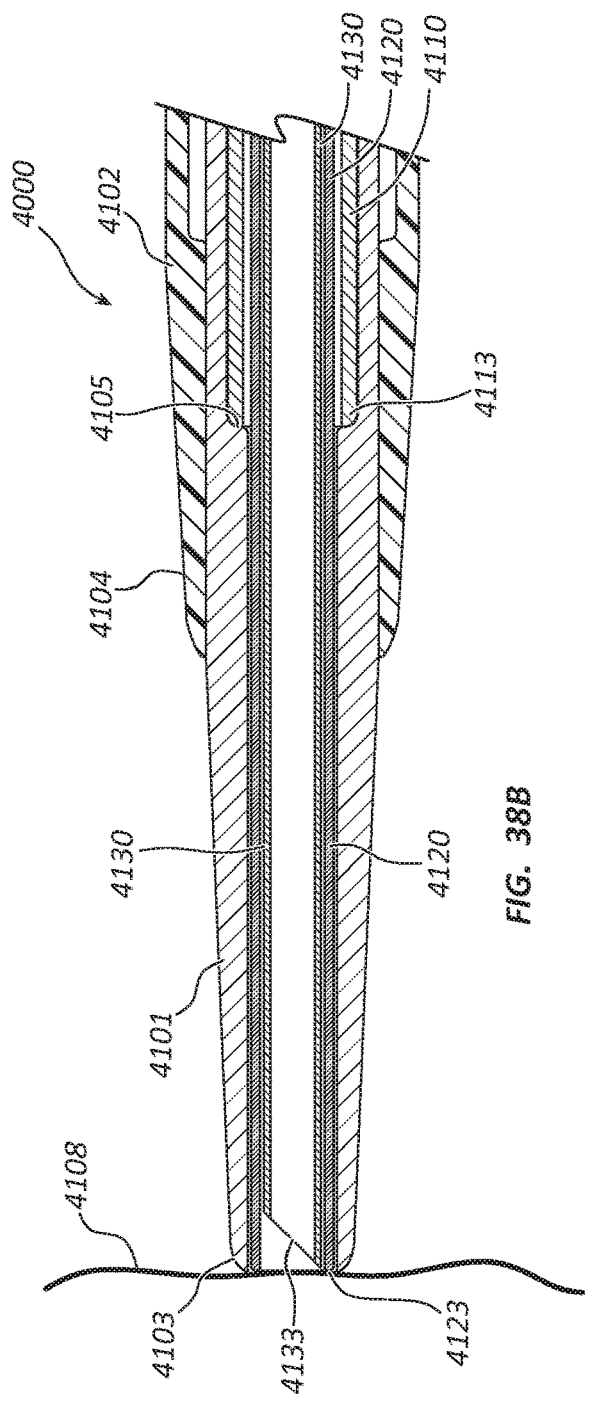
FIG. 38A
FIG. 38B

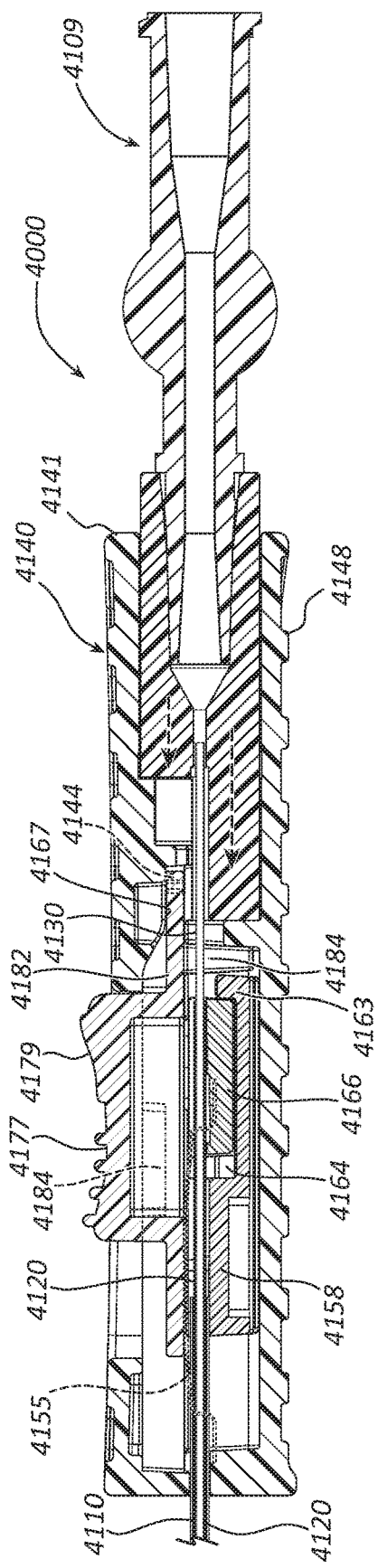
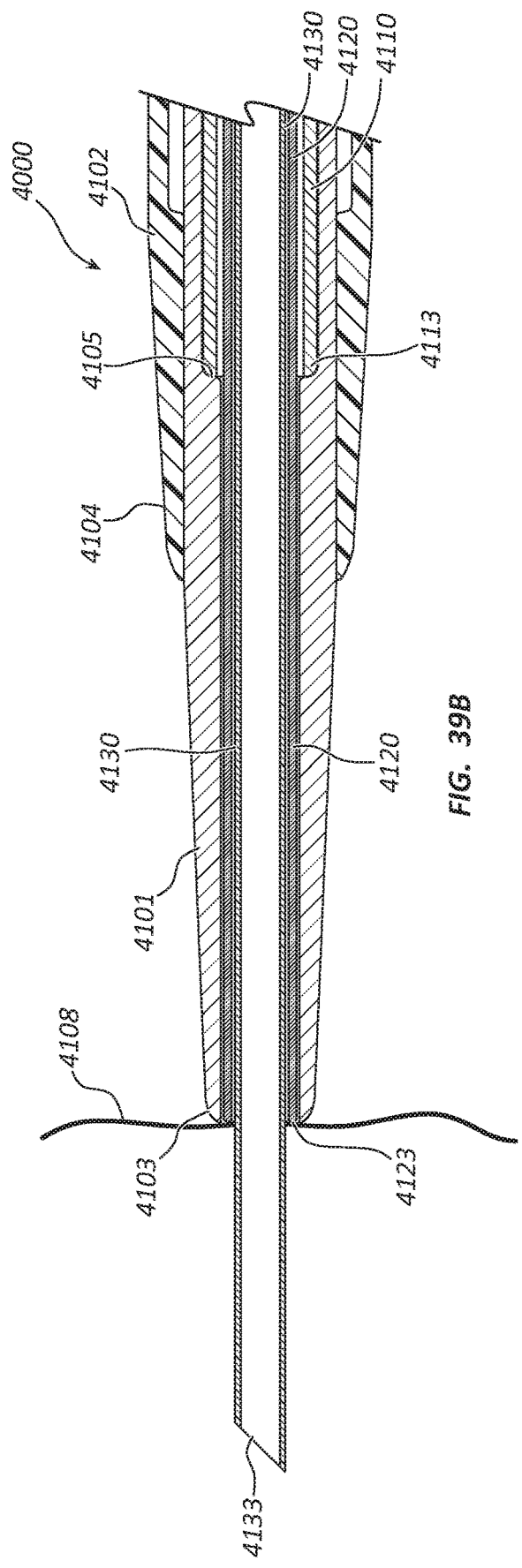
FIG. 39A
FIG. 39B

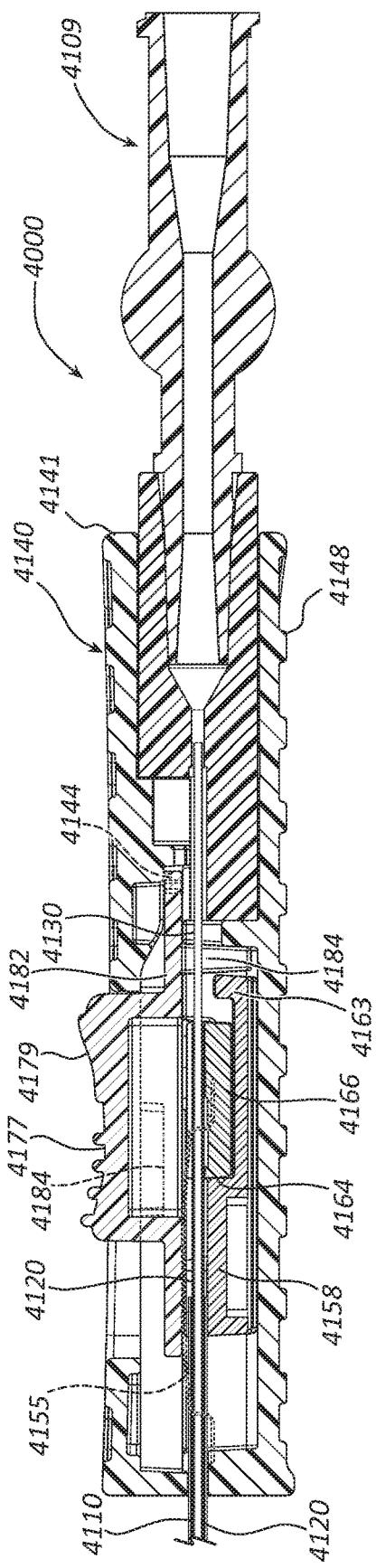
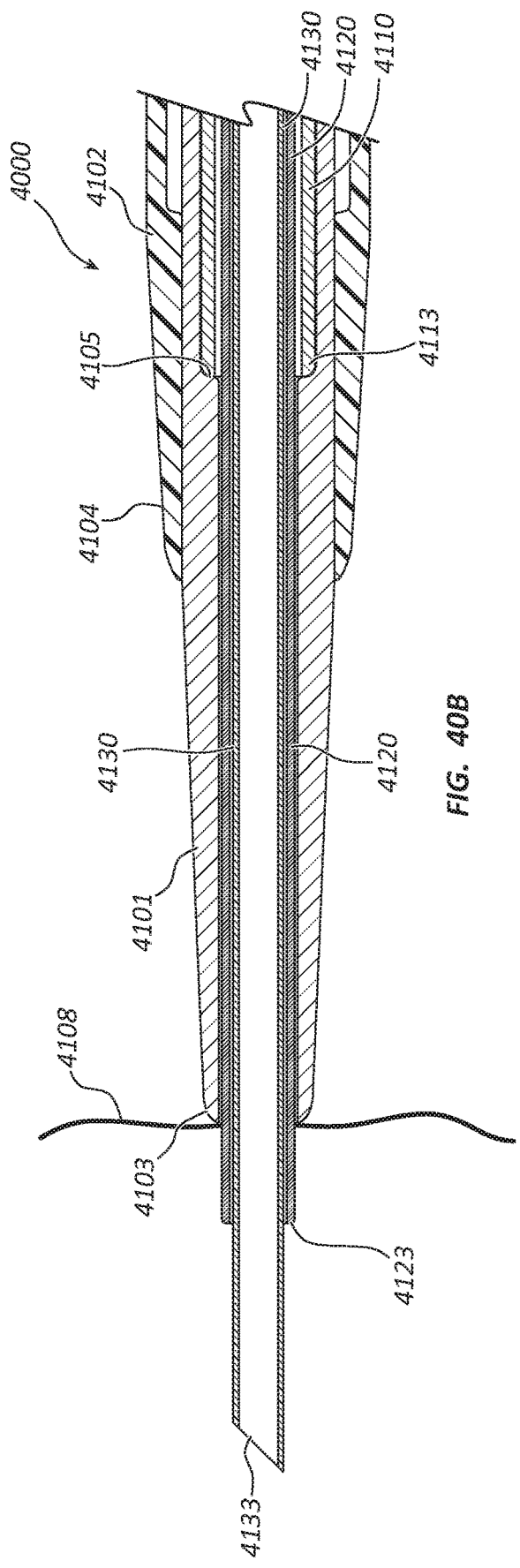
FIG. 40A
FIG. 40B

200

TELESCOPING ATRIAL SEPTUM NEEDLE

RELATED APPLICATIONS

The present application claims priority to U.S. Provisional Application No. 62/743,915 filed on Oct. 10, 2018 and titled "TELESCOPING ATRIAL SEPTUM NEEDLE" which is hereby incorporated by reference in its entirety.

TECHNICAL FIELD

The present disclosure relates generally to elongate devices such as needles, including needle assemblies. More specifically, in some embodiments, the present disclosure relates to telescoping needle assemblies used, for example, to cross an atrial septum.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 2A is a longitudinal cross-sectional view of an outer cannula of the telescoping needle assembly of FIG. 1 comprising a spiral cut.

FIG. 2B is a longitudinal cross-sectional view of an outer cannula of the telescoping needle assembly of FIG. 1 comprising a spiral cut.

FIG. 4 is a longitudinal cross-sectional view of a needle of the telescoping needle assembly of FIG. 1.

FIG. 4A is a longitudinal cross-sectional view of a first embodiment of the needle tip of FIG. 4.

FIG. 4B is a perspective view of a second embodiment of the needle tip of FIG. 4 comprising a lazer welded heel edge portion.

FIG. 4C is a perspective view of a third embodiment of the needle tip of FIG. 4 comprising a cut-away heel portion FIG. 4D is a longitudinal cross-sectional view of a fourth embodiment of the needle tip of FIG. 4 comprising a bent tip.

FIG. 4E is a perspective view of a distal portion of the needle tip of FIG. 4 comprising an off-center taper and smoothed edge corners.

FIG. 4F is a perspective view of a distal portion of the needle tip of FIG. 4 comprising secondary grinds on a back side.

FIG. 7A is a longitudinal cross-sectional view of a proximal portion of the telescoping needle assembly of FIG. 1 in an unlocked state.

FIG. 7B is a longitudinal cross-sectional view of a distal portion of the telescoping needle assembly of FIG. 1 in a needle extending state.

FIG. 8A is a longitudinal cross-sectional view of a proximal portion of the telescoping needle assembly of FIG. 1 in a middle cannula extending state.

FIG. 8B is a longitudinal cross-sectional view of a distal portion of the telescoping needle assembly of FIG. 1 in a middle cannula extending state.

FIG. 11A is a longitudinal cross-sectional view of a proximal portion of the telescoping needle assembly of FIG. 9 in a locked state.

FIG. 11B is a longitudinal cross-sectional view of a distal portion of the telescoping needle assembly of FIG. 9 in a cannula loaded state.

FIG. 17A is a longitudinal cross-sectional view of a proximal portion of the telescoping needle assembly of FIG. 14 in an unlocked state.

FIG. 17B is a longitudinal cross-sectional view of a distal portion of the telescoping needle assembly of FIG. 14 in a needle extending state.

FIG. 21A is a longitudinal cross-sectional view of a proximal portion of the telescoping needle assembly of FIG. 19 in a locked state.

FIG. 21B is a longitudinal cross-sectional view of a distal portion of the telescoping needle assembly of FIG. 19 in a cannula loaded state.

FIG. 23A is a longitudinal cross-sectional view of a proximal portion of the telescoping needle assembly of FIG. 19 in a middle cannula extending state.

FIG. 23B is a longitudinal cross-sectional view of a distal portion of the telescoping needle assembly of FIG. 19 in a middle cannula extending state.

FIG. 25A is an exploded perspective top view of a handle of the telescoping needle assembly of FIG. 24.

FIG. 26A is a longitudinal cross-sectional view of a proximal portion of the telescoping needle assembly of FIG. 24 in a locked state.

FIG. 26B is a longitudinal cross-sectional view of a distal portion of the telescoping needle assembly of FIG. 24 in a cannula loaded state.

FIG. 27A is a longitudinal cross-sectional view of a proximal portion of the telescoping needle assembly of FIG. 24 in an unlocked state.

FIG. 27B is a longitudinal cross-sectional view of a distal portion of the telescoping needle assembly of FIG. 24 in a needle extending state.

FIG. 31 is a perspective view of a telescoping needle assembly according to a sixth embodiment.

FIG. 38A is a longitudinal cross-sectional view of a proximal portion of the telescoping needle assembly of FIG. 36 in a locked state.

FIG. 38B is a longitudinal cross-sectional view of a distal portion of the telescoping needle assembly of FIG. 36 in a cannula loaded state.

FIG. 39A is a longitudinal cross-sectional view of a proximal portion of the telescoping needle assembly of FIG. 36 in an unlocked state.

FIG. 39B is a longitudinal cross-sectional view of a distal portion of the telescoping needle assembly of FIG. 36 in a needle extending state.

FIG. 40A is a longitudinal cross-sectional view of a proximal portion of the telescoping needle assembly of FIG. 36 in a middle cannula extending state.

FIG. 40B is a longitudinal cross-sectional view of a distal portion of the telescoping needle assembly of FIG. 36 in a middle cannula extending state.

DETAILED DESCRIPTION

Figure 1:
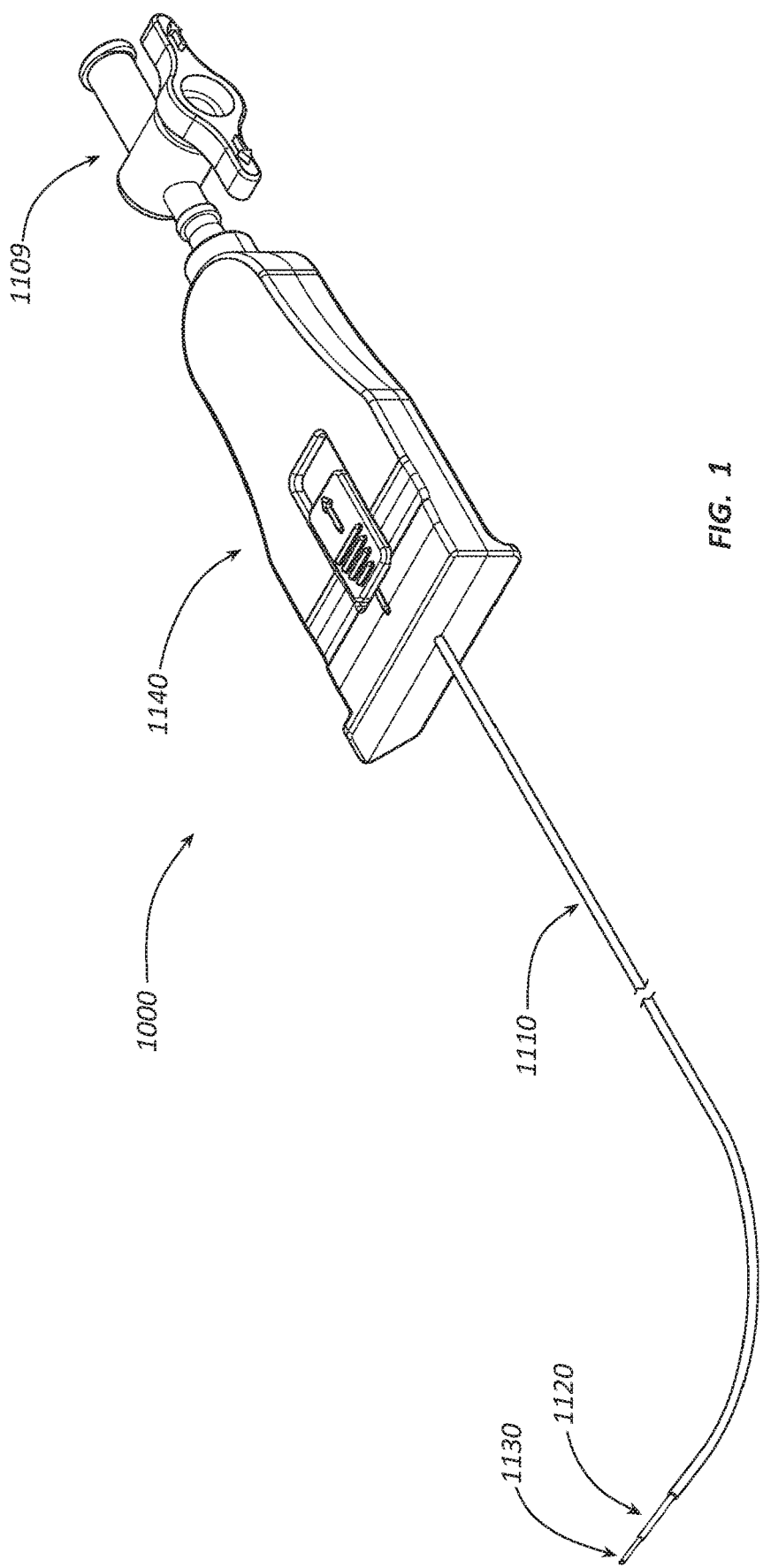
FIG. 1 is a perspective view of a telescoping needle assembly.

In certain instances, elongate needle assemblies may be utilized to provide transseptal access to either the left or right atrium to accomplish certain medical procedures, such as therapeutic and diagnostic procedures. In some instances, the telescoping needle assembly may comprise an outer cannula, a middle cannula, and an inner cannula or needle. The cannulas and needle may be telescopingly disposed such that the middle cannula is axially displaceable within the outer cannula and the needle is axially displaceable within the middle cannula. The telescoping needle assembly may also comprise a handle that is operatively coupled to the cannulas and the needle. The handle may comprise a locking member configured to releasably lock one or more of the cannulas and needle in an axial position.

In certain instances, the telescoping needle assembly may be inserted into a patient's vascular system remote from an atrial septum through a dilator and sheath assembly. A tip of the dilator may be positioned against the atrial septum. During such procedures, a sharp end of the needle can be advanced through the tip of the dilator when unlocked from the locking member of the handle such that the needle penetrates the atrial septum and provides access to the opposing atrium.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure but is merely representative of various embodiments. While the various aspects of the embodiments are presented in drawings, the drawings are not necessarily drawn to scale unless specifically indicated.

It will be appreciated that various features are sometimes grouped together in a single embodiment, figure, or description thereof for the purpose of streamlining the disclosure. Many of these features may be used alone and/or in combination with one another.

The phrase "coupled to" refers to any form of interaction between two or more entities, including mechanical, electrical, magnetic, electromagnetic, fluid, and thermal interaction. Two components may be coupled to with each other even though they are not in direct contact with each other. For example, two components may be coupled to each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use. As specifically applied to the cannulas and needle of the telescoping needle assembly, the proximal end of the cannulas and needle refer to the end nearest the handle and the distal end refers to the opposite end. Thus, if at one or more points in a procedure a physician changes the orientation of the telescoping needle assembly, as used herein, the term "proximal end" always refers to the handle end of the telescoping needle assembly (even if the distal end is temporarily closer to the physician).

FIGS. 1-40B illustrate different views of various embodiments of telescoping needle assemblies. In certain views each assembly may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

FIGS. 1-8B depict an embodiment of a telescoping needle assembly 1000. In the illustrated embodiment, the telescoping needle assembly 1000 includes a first elongate member or an outer cannula 1110, a second elongate member or a middle cannula 1120, an inner cannula or needle 1130, and a handle 1140. In other embodiments, the telescoping needle assembly 1000 may only include a subset of these components. For instance, in some embodiments the assembly may not include the middle cannula 1120. In some embodiments, a medical device, such as a stopcock 1109, syringe, medical connector, etc., may be coupled to a proximal end of the handle 1140 which may in some embodiments establish fluid communication with the needle 1130.

FIGS. 2A and 2B depict different embodiments of the outer cannula 1110. The outer cannula 1110A of FIG. 2A may resemble outer cannula 1110B of FIG. 2B in certain respects. Accordingly, like features are designated with like reference numerals, with different suffix alpha characters. For example, the embodiment depicted in FIG. 2A includes a lumen 1112A that may, in some respects, resemble the lumen 1112B of FIG. 2B. Relevant disclosure set forth above regarding similarly identified features thus may not be repeated hereafter. Moreover, specific features of the outer cannula 2A shown in FIG. 2A may not be shown or identified by a reference numeral in FIG. 2B or in the written description. However, such features may clearly be the same, or substantially the same, as features depicted in FIG. 2A and/or described with respect to outer cannula 1110A. Accordingly, the relevant descriptions of such features apply equally to the features of the outer cannula 1110B depicted in FIG. 2B. Any suitable combination of the features, and variations of the same, described with respect to the outer cannula 1110A illustrated in FIG. 2A can be employed with the outer cannula 1110B of FIG. 2B, and vice versa. Furthermore, the outer cannula 1110 as recited herein may have reference to outer cannula 1110A or outer cannula 1110B.

As illustrated in the embodiment of FIG. 2A, an outer cannula 1110A includes an outer tubular body 1111A comprising a lumen 1112A extending through the outer body 1111A from a proximal end 1114A to a distal end 1113A. The lumen 1112 is sized to slidingly receive the middle cannula 1120. A diameter of the outer body 1111 may range from 14 gauge to 21 gauge. The length of the outer body 1111 may range from about 40 cm to 110 cm, from 50 cm to 100 cm, and from 70 cm to 100 cm. The distal end 1113A may have a blunt shape and/or may be squared off relative to a longitudinal axis of the outer body 1111A. In some embodiments, the distal end 1113 may be squared off with or without a radius. In the illustrated embodiment, the outer cannula 1110A has an arcuate portion 1115A adjacent to the distal end 1113A. The angle of the arcuate portion 1115A may range from about 1 degree to 120 degrees, from 40 degrees to 120 degrees, and from 40 degrees to 90 degrees. In other embodiments, the outer cannula 1110A may be straight from the distal end 1113A to the proximal end 1114A. The outer cannula 1110A may be formed from any suitable rigid or semi-rigid medical grade material, such as stainless steel, nitinol, titanium, thermoplastics, etc.

FIG. 2B depicts an outer cannula 1110B comprising a spiral cut 1233B to enable flexibility of at least a portion of the outer cannula 1110B. The outer cannula 1110B may be straight or have an arcuate portion 1115B in a free state. In the illustrated embodiment, the spiral cut 1233B may extend along the arcuate portion 1115B and/or along a straight portion. In some embodiments, the spiral cut 1233B may be disposed distal of the arcuate portion 1115B. In other embodiments, the spiral cut 1233B may be disposed proximal of the arcuate portion 1115B. In still other embodiments, the spiral cut 1233B may extend from the proximal end 1114B to the distal end 1113B. The spiral cut 1233B may extend radially through the wall of the outer cannula 1110B. The spiral cut 1233B may also include one or more uncut sections 1234B such that the spiral cut 1233B is discontinuous. The uncut sections 1234B may inhibit lengthening and/or shortening of the outer cannula 1110B when exposed to tension and compression forces, respectively. In the illustrated embodiment, the outer cannula 1110B comprises a weld 1236B at the distal end 1113B. The weld 1236B may be configured to provide a smooth rounded cannula edge. The weld 1236B may also form an inside rim of reduced diameter that may reduce clearance between an inside diameter of the outer cannula 1110B and an outside diameter of a cannula to be disposed within the outer cannula 1110B.

Figure 3A:
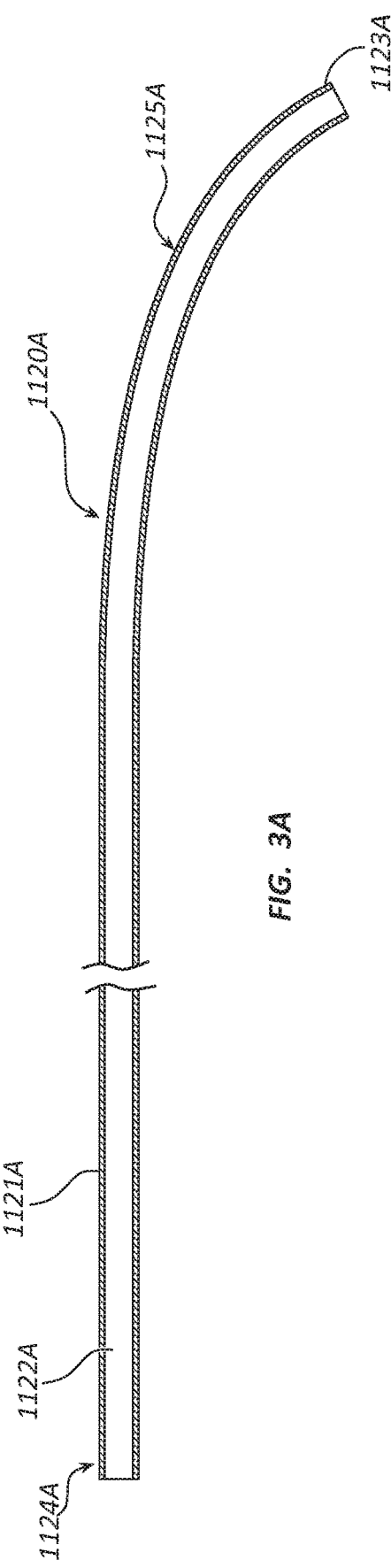
FIG. 3A is a longitudinal cross-sectional view of a middle cannula of the telescoping needle assembly of FIG. 1.
Figure 3B:
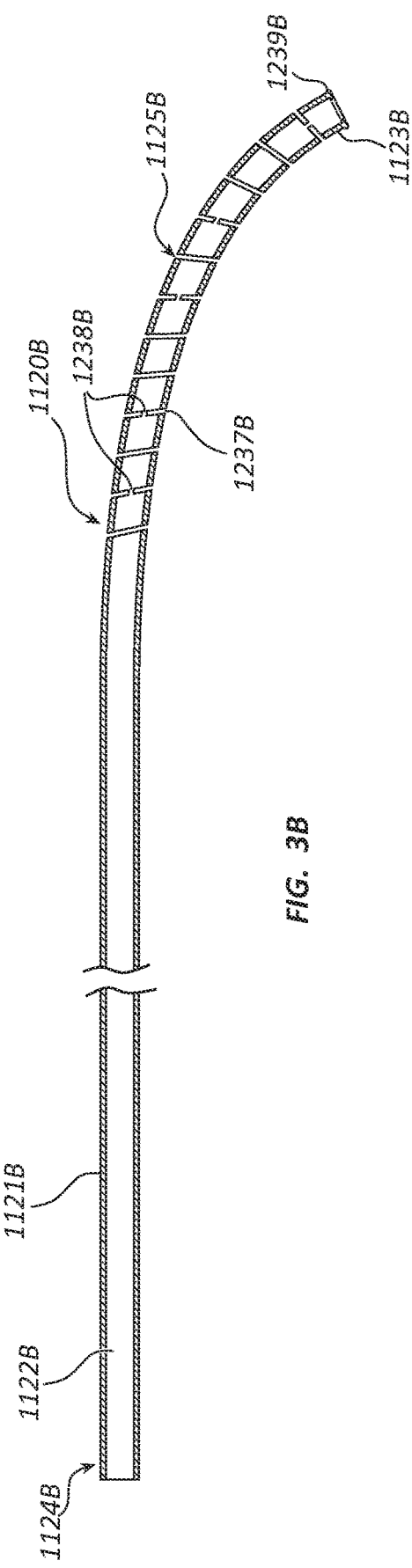
FIG. 3B is a longitudinal cross-sectional view of a middle cannula of the telescoping needle assembly of FIG. 1 comprising a spiral cut portion.

FIGS. 3A and 3B depict different embodiments of the middle cannula 1120 such that middle cannula 1120A may resemble middle cannula 1120B in certain respects. Accordingly, like features are designated with like reference numerals, with different suffix alpha characters. For example, the embodiment depicted in FIG. 3A includes a lumen 1122A that may, in some respects, resemble the lumen 1122B of FIG. 3B. Relevant disclosure set forth above regarding similarly identified features thus may not be repeated hereafter. Moreover, specific features of the middle cannula 3A shown in FIG. 3A may not be shown or identified by a reference numeral in FIG. 3B or in the written description. However, such features may clearly be the same, or substantially the same, as features depicted in FIG. 3A and/or described with respect to middle cannula 1120A. Accordingly, the relevant descriptions of such features apply equally to the features of the middle cannula 1120B depicted in FIG. 3B. Any suitable combination of the features, and variations of the same, described with respect to the middle cannula 1120A illustrated in FIG. 3A can be employed with the middle cannula 1120B of FIG. 3B, and vice versa. Furthermore, the middle cannula 1120 as recited herein may have reference to middle cannula 1120A or middle cannula 1120B.

As illustrated in the embodiment of FIG. 3A, the middle cannula 1120A comprises a middle body 1121A having a middle lumen 1122B extending through the middle body 1121A from a proximal end 1124A to a distal end 1123A. The middle lumen 1122A may be sized to slidingly receive the needle 1130. A diameter of the middle body 1121A may range from 15 gauge to 29 gauge. The length of the middle body 1121A may range from about 40 cm to 115 cm, from 60 cm to 115 cm, and from 80 cm to 115 cm. The middle body 1121A may also be sized to be slidingly received within the lumen 1112 of the outer cannula 1110. Further, in certain embodiments, the distal end 1123A has a blunt shape that is configured to prevent skiving of material from a lumen of a dilator as will be described below. In some embodiments, the distal end 1123A may be squared off with or without a radius. The distal end 1123A may be configured to extend beyond the distal end 1113 of the middle body 1121A in a ready or packaged state. The distal end 1123 may extend from the distal end 1113 a distance that ranges from about 1 mm to 20 mm, from 10 mm to 20, and from 5 mm to 15 mm. The middle body 1121A has an arcuate portion 1125A adjacent to the distal end 1123A that matches the arcuate portion 1115A of the outer body 1111A. In other embodiments, the middle body 1121A may be straight from the distal end 1123A to the proximal end 1124A. The middle body 1121A may be formed from any suitable rigid or semi-rigid medical grade material, such as stainless steel, nitinol, titanium, thermoplastics, etc.

FIG. 3B depicts a middle cannula 1120B comprising a spiral cut 1237B configured to increase the flexibility of at least a portion of the middle cannula 1120B. The middle cannula 1120B may be straight or have an arcuate portion 1125B in a free state. In the illustrated embodiment, the spiral cut 1237B may extend along the arcuate portion 1125B and/or along a straight portion. In some embodiments, the spiral cut 1237B may be disposed distal of the arcuate portion 1125B. In other embodiments, the spiral cut 1237B may be disposed proximal of the arcuate portion 1125B. In still other embodiments, the spiral cut 1237B may extend from the proximal end 1124B to the distal end 1123B. The spiral cut 1237B may extend radially through the wall of the middle cannula 1120B. The spiral cut 1237B may include one or more uncut sections 1238B such that the spiral cut 1237B is discontinuous. The uncut sections 1238B may inhibit lengthening and shortening of the middle cannula 1120B when exposed to tension and compression forces, respectively. In the illustrated embodiment, the middle cannula 1120B comprises a weld 1239B at the distal end 1123B. The weld 1239B may be configured to provide a smooth rounded cannula edge. The weld 1239B may also form an inside rim of reduced diameter that may reduce clearance between an inside diameter of the middle cannula 1120B and an outside diameter of a cannula or needle to be disposed within the middle cannula 1120B.

FIG. 4 shows the needle 1130. The needle 1130 may comprise a needle body 1131 having a lumen 1132 extending through the needle body 1131 from a proximal end 1134 to a distal end 1133. In other embodiments, the needle body 1131 may be a solid rod without a lumen. A diameter of the needle body 1131 may range from 17 gauge to 35 gauge. The length of the needle body 1131 may range from 40 cm to 120 cm, from 50 cm to 100 cm, and from 70 cm to 100 cm. The needle body 1131 may be sized to be slidingly received within the middle lumen 1122 of the middle body 1121. The needle body 1131 may have an arcuate portion 1135 adjacent to the distal end 1133 that may match the arcuate portion 1125 of the middle body 1121. In other embodiments, the needle body 1131 may be straight from the distal end 1133 to the proximal end 1134. The needle body 1131 may be formed from any suitable rigid or semi-rigid medical grade material, such as stainless steel, nitinol, titanium, thermoplastics, etc. In the illustrated embodiment, the distal end 1133 may comprise a needle tip 1139 configured to penetrate tissue.

FIGS. 4A-4F depict different embodiments of the needle tip 1139 disposed at the distal end 1133 of the needle 1130. Each of the different embodiments of the needle tip 1139 as depicted in FIGS. 4A-4F may comprise features that may resemble in certain respects features of the other embodiments. Accordingly, like features are designated with like reference numerals, with different suffix alpha characters. For example, the embodiment depicted in FIG. 4A includes a sharp point 1136A that may, in some respects, resemble any of the sharp points 1136B-1136F as depicted in FIGS. 4B-4E, respectively. Relevant disclosure set forth regarding similarly identified features thus may not be repeated thereafter. Moreover, specific features of the needle tips 1139A-1139F shown in any one of FIGS. 4A-4F may not be shown or identified by a reference numeral in the other figures or in the written description. However, such features may clearly be the same, or substantially the same. Accordingly, the relevant descriptions of such features apply equally to the features of the other needle tips depicted in FIGS. 4A-4F. Any suitable combination of the features, and variations of the same, described with respect to the needle tips 1139A-1139F illustrated in FIGS. 4A-4F can be employed with the needle 1130 and related components of FIG. 4. Furthermore, the needle tip 1139 as recited herein may have reference to any one of needle tips 1139B-1139F.

FIG. 4A shows a needle tip 1139A comprising an angled cannula edge and a sharp point 1136A. The needle tip 1139A further includes cutting facets 1137A along the angled cannula edge.

FIG. 4B shows a needle tip 1139B comprising an angled cannula edge and a sharp point 1136B. The needle tip 1139B further includes cutting facets 1137B along the angled cannula edge and a lazer weld 1231B along a heel portion of the angled cannula edge. The weld 1231B may form a rounded edge along the heel portion.

FIG. 4C shows a needle tip 1139C comprising an angled cannula edge and a sharp point 1136C. The needle tip 1139C further includes cutting facets 1137C along the angled cannula edge. The needle tip 1139C further includes a cut-away section 1232C along the heel portion such that the angled cannula edge is cut away in the proximal direction leaving a blunt edge corner along the heel portion.

FIG. 4D shows a needle tip 1139D comprising an angled cannula edge and a sharp point 1136D. The needle tip 1139D further includes cutting facets 1137D along the angled cannula edge. A tip portion including the sharp point 1136D is bent radially inward a distance 1233D such that the sharp point 1136D is disposed radially inward of an outside diameter by a distance 1233D between about 0.002 inches and 0.014 inches, 0.004 inches and 0.012 inches, 0.006 inches and 0.010 inches, or a radial distance of about 0.008 inches.

FIG. 4E shows a needle tip 1139E comprising an angled cannula edge and a sharp point 1136E. The needle tip 1139E includes cutting facets 1137E along the angled cannula edge and back-cutting facets 1235E along the angled cannula edge adjacent the sharp point 1136E such that the sharp point 1136E is formed by an intersection of the back-cutting facets 1235E and an inside lumen surface. The cutting facets 1137E and/or the back-cutting facets 1235E may be non-symmetrical such that the sharp point 1136E may be laterally offset from a longitudinal axis of the needle tip 1139E. The edge corners, i.e., the intersections of surfaces, are rounded or smoothed so as to remove sharpness of the edge corners.

FIG. 4F shows a needle tip 1139F comprising an angled cannula edge and a sharp point 1136F. The needle tip 1139F includes cutting facets 1137F along the angled cannula edge. The needle tip 1139F further includes back-cutting facets 1235F cut along the angled cannula edge adjacent the sharp point 1136C such that the sharp point 1136E is formed by an intersection of the back-cutting facets 1235F and an inside lumen surface.

Figure 5A:
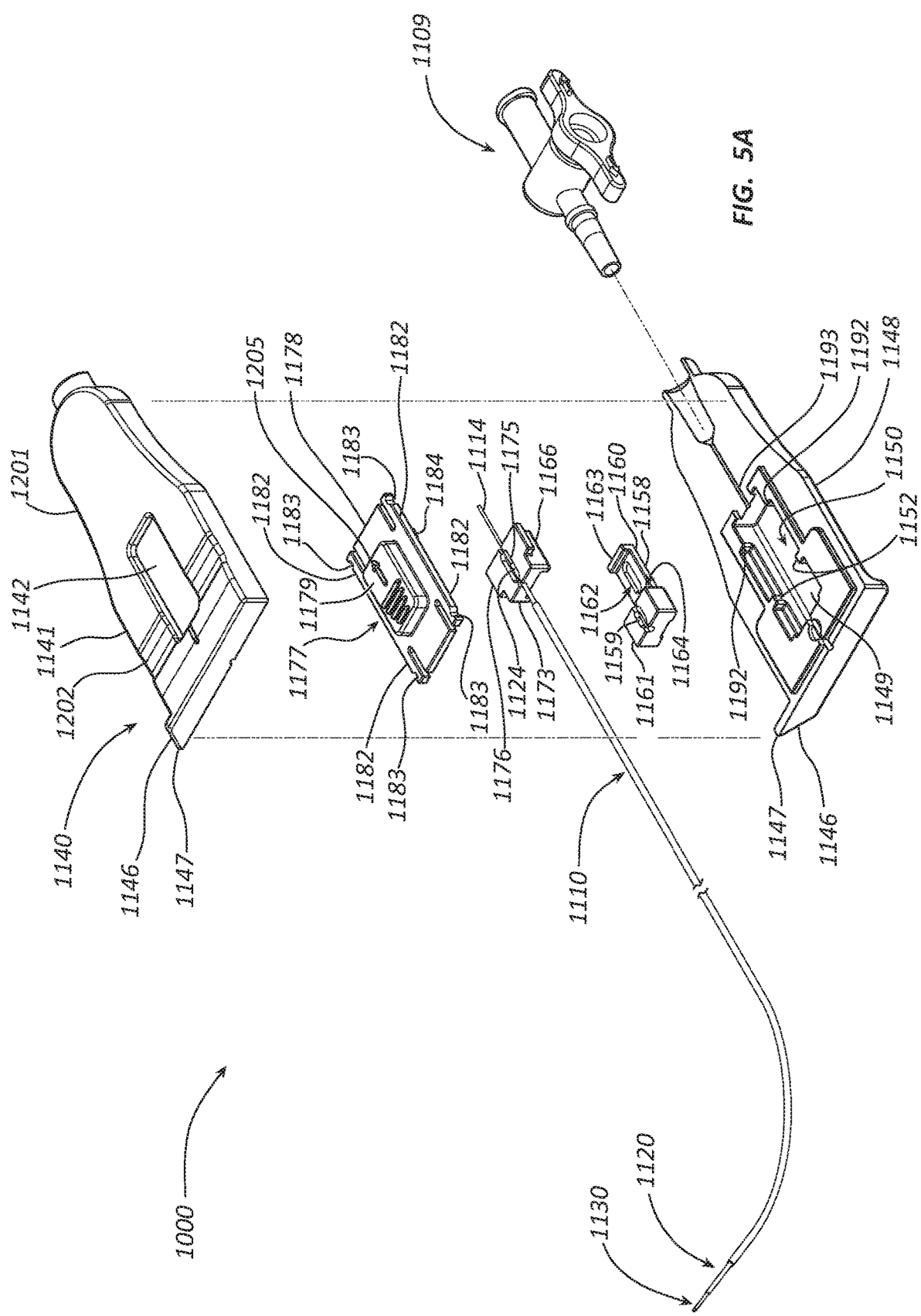
FIG. 5A is an exploded perspective top view of a handle of the telescoping needle assembly of FIG. 1.
Figure 5B:
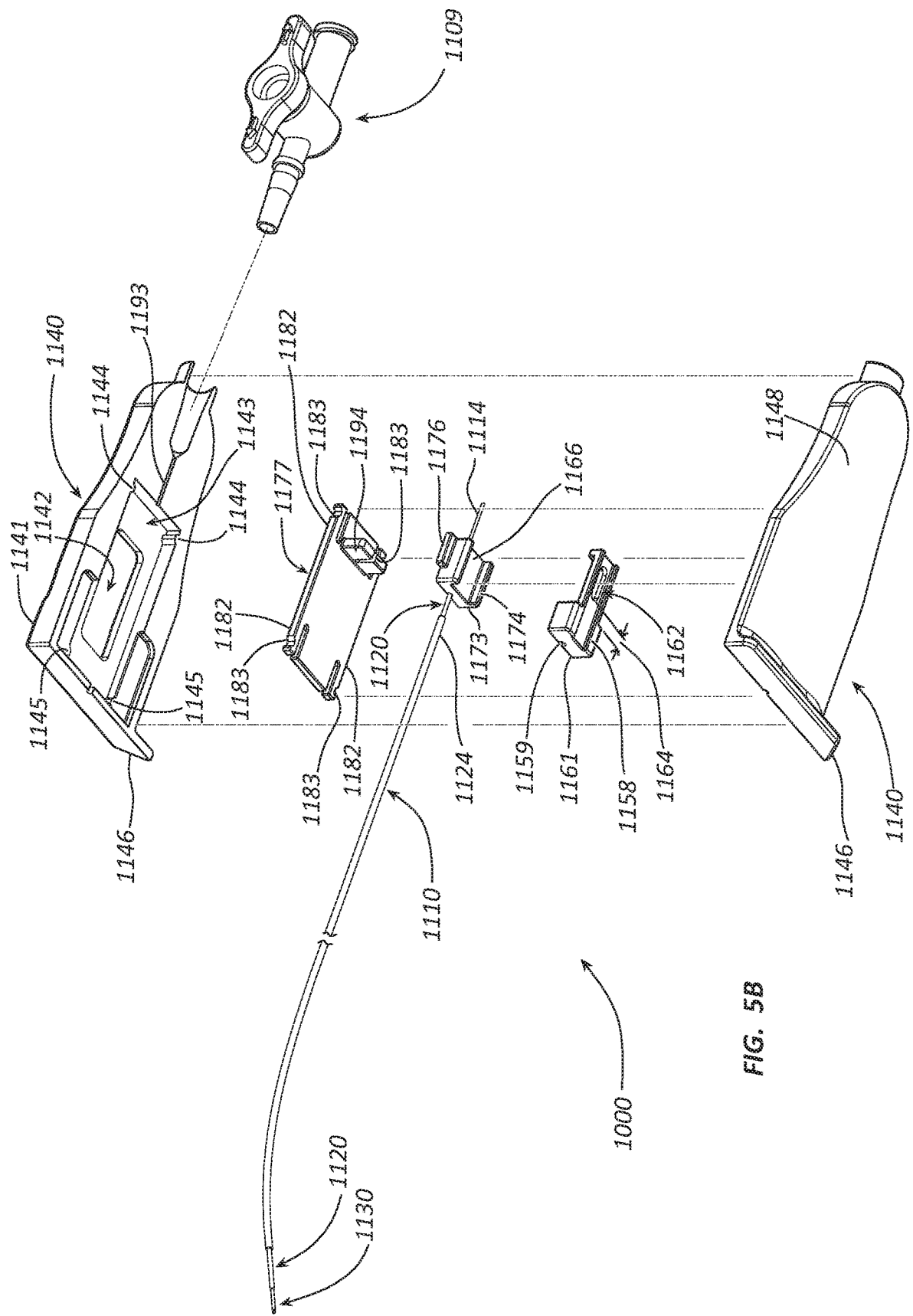
FIG. 5B is an exploded perspective bottom view of the handle of the telescoping needle assembly of FIG. 1.

FIGS. 5A and 5B illustrate exploded views of the handle 1140 of the telescoping needle assembly 1000. In the illustrated embodiment, the handle 1140 includes an upper housing 1141, a lower housing 1148, an outer cannula carriage 1158, a middle cannula carriage 1166, and a locking member 1177.

As shown in FIGS. 5A and 5B, the upper housing 1141 is configured to couple with the lower housing 1148. The upper housing 1141 and the lower housing 1148 may be coupled using any suitable technique, such as gluing, welding, snap fit, etc. The upper housing 1141 may include a proximal portion 1201 that has a smaller width than a distal portion 1202 and features an outer surface to enhance gripability. In some embodiments, the gripping features may include transverse ribs, dimples, bumps, surface texturing, grip enhancing material, etc. The upper housing 1141 may include a first portion of an orientation indicator 1146 disposed adjacent the distal portion 1202 and extending orthogonally from a side of the upper housing 1141 that is aligned with the direction of curvature of the arcuate portion 1115 of the outer cannula 1110. The orientation indicator 1146 may be tapered to a point 1147. In other embodiments, the orientation indicator 1146 may include a radiused distal end, an arrow shape, or any other configuration suitable to indicate the orientation of the arcuate portion 1115 of the outer cannula 1110. The upper housing 1141 may be formed of any suitable rigid or semi-rigid thermoplastic material, such as polycarbonate, polypropylene, polyethylene, polyvinylchloride, etc.

In the illustrated embodiment, the upper housing 1141 includes an elongate opening 1142, a recess 1143 disposed in a bottom surface, proximal detents 1144, and distal detents 1145 disposed on lateral sides of the recess 1143. The elongate opening 1142 is oriented with a longitudinal axis of the upper housing 1141 and is configured to slidingly receive a button 1179 of the locking member 1177. The recess 1143 is elongated and configured to slidingly receive a body 1178 of the locking member 1177. The proximal detents 1144 and the distal detents 1145 are disposed at proximal and distal portions of the recess 1143, respectively, and are configured to couple with cantilever arms 1182 of the locking member 1177 as will be described below.

With continued reference to FIGS. 5A and 5B, the lower housing 1148 is configured to couple with the upper housing 1141. The lower housing 1148 is generally shaped to match the shape of the upper housing 1141 and may include features on an outer surface to facilitate gripping. In some embodiments, the gripping features may include transverse ribs, dimples, bumps, surface texturing, grip enhancing material, etc. The lower housing 1148 includes a second portion of the orientation indicator 1146 disposed adjacent the distal portion and extending orthogonally from a side of the lower housing 1148 that is aligned with the direction of curvature of the arcuate portion 1115 of the outer cannula 1110. The orientation indicator 1146 is tapered to the point 1147. In other embodiments, the orientation indicator 1146 may include a radiused distal end, an arrow shape, or any other configuration suitable to indicate the orientation of the arcuate portion 1115 of the outer cannula 110. The lower housing 1148 may be formed of any suitable rigid or semi-rigid thermoplastic material, such as polycarbonate, polypropylene, polyethylene, polyvinylchloride, etc.

The lower housing 1148 includes an elongate cavity 1149. The cavity 1149 is oriented with a longitudinal axis of the lower housing 1148 and is configured to slidingly receive the outer cannula carriage 1158 and the middle cannula carriage 1166. The cavity 1149 is configured with a wide upper portion and a narrow lower portion. A pair of shelves 1150 are disposed on lateral sides of the cavity 1149 and divide the upper portion from the lower portion. The shelves 1150 include inwardly extending distal stops 1152 and proximal stops 1192.

The outer cannula carriage 1158 includes a proximal portion 1160 and a distal portion 1161. The outer cannula carriage 1158 is configured to be slidingly disposed within the cavity 1149 between the shelves 1150. The distal portion 1161 comprises a slot 1159 extending longitudinally through an upper surface. The slot 1159 is sized to receive the proximal end 1114 of the outer cannula 1110. The outer cannula 1110 may be fixedly coupled to the outer cannula carriage 1158 using any suitable technique, such as gluing, welding, insert molding, etc. The proximal portion 1160 includes a vertical stop 1163. A recess 1162 is disposed between the proximal portion 1160 and the vertical stop 1163. The recess 1162 is configured to slidingly receive the middle cannula carriage 1166. The outer cannula carriage 1158 may be formed of any suitable rigid or semi-rigid thermoplastic material, such as polycarbonate, polypropylene, polyethylene, polyvinylchloride, etc.

The middle cannula carriage 1166 includes a body 1173. The middle cannula carriage 1166 is configured to be slidingly disposed within the cavity 1149 and within the recess 1162 of the outer cannula carriage 1158 such that the middle cannula carriage 1166 is disposed between the proximal portion 1160 and the vertical stop 1163. A gap 1164 is defined between the middle cannula carriage 1166 and the distal portion 1161. The body 1173 comprises a slot 1175 extending longitudinally through an upper surface. The slot 1175 is sized to receive the proximal end 1124 of the middle cannula 1120. The middle cannula 1120 may be fixedly coupled to the middle cannula carriage 1166 using any suitable technique, such as gluing, welding, insert molding, etc. The body 1173 includes rails 1174 extending from a lower surface. The rails 1174 are configured to straddle a portion of the distal portion 1161 of the outer cannula carriage 1158 and to slidingly couple with a bottom surface of the cavity 1149. Laterally extending wings 1176 extend from the body 1173 and are disposed over the shelves 1150 between the distal stops 1152 and the proximal stops 1192.

The locking member 1177 includes the body 1178, an upward projection or button 1179, and a downward projection 1184. The body 1178 is configured to be slidingly received within the recess 1143 of the upper housing 1141 and to slidingly couple with an upper surface of the lower housing 1148. The body 1178 includes the cantilever arms 1182 extending proximally and distally from a central portion and disposed on lateral portions of the body 1178. Each cantilever arm 1182 includes a notch 1183 disposed adjacent a distal end of the cantilever arm 1182. The notches 1183 are configured to engage with the proximal detents 1144 or the distal detents 1145 of the upper housing 1141 such that the locking member 1177 is restricted from longitudinal displacement. The button 1179 extends vertically upward from the body 1178 and is configured to be received within the elongate opening 1142 of the upper housing 1141. The button 1179 is configured to be engaged by a finger of a clinician to displace the locking member 1177 proximally or distally. The button 1179 may include features to facilitate displacement of the locking member 1177. The features may include transverse ribs, bumps, dimples, textured surface, slip resistant material, etc. The button 1179 may include an indicium 1205, such as an arrow shape, to indicate the direction the locking member 1177 may be displaced to unlock the handle 1140. The downward projection 1184 extends from a bottom surface of the body 1178 and is configured to be received within the cavity 1149 of the lower housing 1148. The downward projection 1184 includes a slot or passage 1194 sized to slidingly receive the needle 1130.

The upper housing 1141 and the lower housing 1148 include a channel 1193 extending through the proximal portion 1201 of the housings 1141, 1148. A distal portion of the channel 1193 opens into the cavity 1149 and is sized to receive the proximal end 1134 of the needle 1130. The proximal end 1134 may be fixedly coupled within the channel 1193 using any suitable technique, such as gluing, welding, insert molding, etc. A proximal portion of the channel 1193 may be configured to couple to a medical device, such as the stopcock 1109, syringe, medical connector, etc.

In some embodiments, the upper housing 1141 and the lower housing 1148 may include a visual and/or an audible indicator of a locked state and an unlocked state of the locking member 1177. For example, when the locking member 1177 is transitioned from the locked state to the unlocked state, an audible signal may be generated by the distally extending cantilever arms 1182 as the notches 1183 decouple from the distal detents 1145. In other embodiments, the housings 1141, 1148 may include a window through which a portion of the locking member 1177 may be visualized. The visualized portion may be colored red when the locking member 1177 is in the locked state and colored green when the locking member 1177 is in the unlocked state.

In use, the telescoping needle assembly 1000 may be used for medical procedures requiring remotely crossing a vessel wall, membrane, or septum, such as an atrial septum, to gain access to a remote vessel or chamber. In some instances, the telescoping needle assembly 1000 may be used to remotely cross the atrial septum from the right atrium to the left atrium in order to conduct diagnostic and therapeutic procedures, such as left heart pressure and other functional measurements, cardiac mapping, ablation, paten foramen ovale (PFO) closure, left atrial appendage occlusion or closure, etc.

Figure 6A:
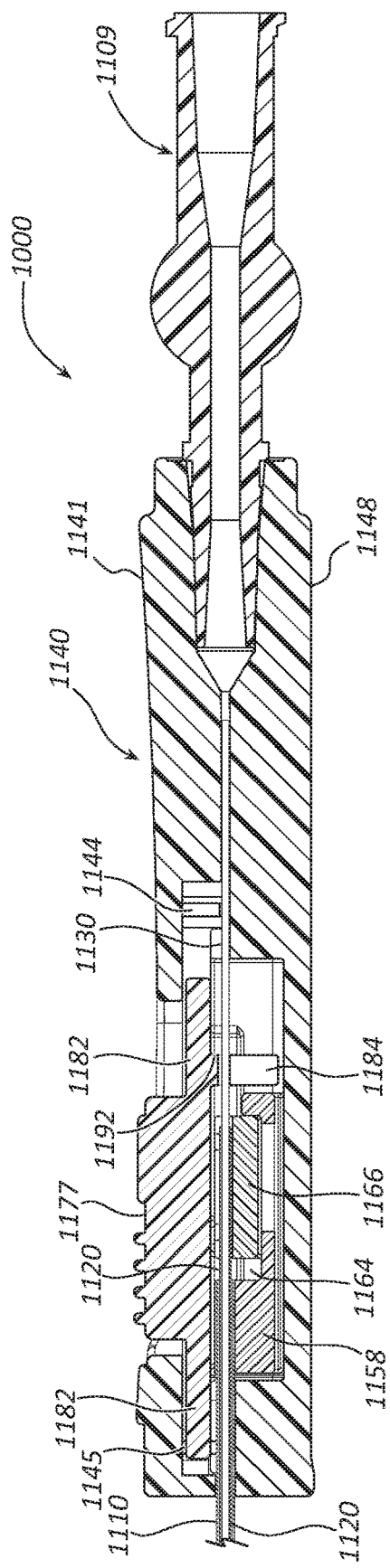
FIG. 6A is a longitudinal cross-sectional view of a proximal portion of the telescoping needle assembly of FIG. 1 in a locked state.
Figure 6B:
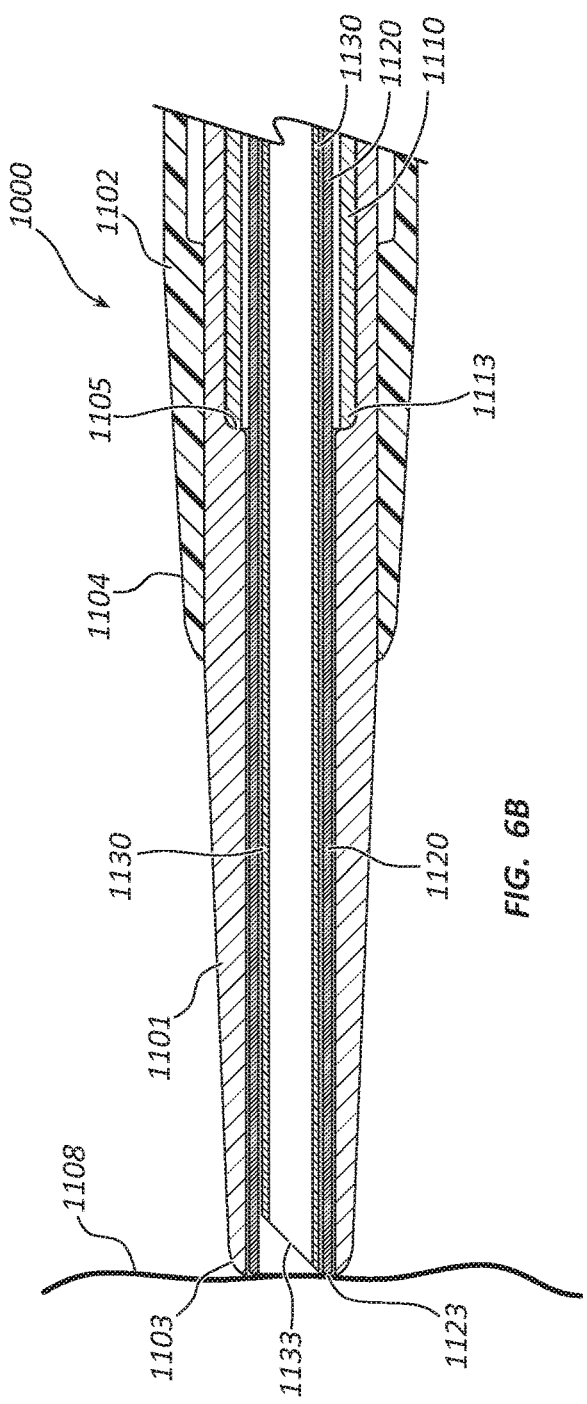
FIG. 6B is a longitudinal cross-sectional view of a distal portion of the telescoping needle assembly of FIG. 1 in a cannula loaded state.

FIG. 6A illustrates a configuration of the handle 1140 and FIG. 6B illustrates the configuration of a distal end portion of the telescoping needle assembly 1000 in a loaded state. Referring to FIG. 6B, the dilator 1101 may be disposed within a lumen of a sheath 1102 such that a distal end 1103 of the dilator 1101 extends beyond a distal end 1104 of the sheath 1102. The dilator 1101 and the sheath 1102 may be inserted from a peripheral site, such as the groin, into the central vasculature or heart of the patient and positioned within the central vasculature or heart such that the distal end 1103 of the dilator 1101 is positioned against a vessel wall, membrane, or septum, such as an atrial septum 1108. The telescoping needle assembly 1000 is oriented such that the orientation indicator 1146 of the handle 1140 is directed toward a curvature of the dilator 1101 resulting in the curvature of the arcuate portion 1115 of the outer cannula 1110 aligning with the curvature of the dilator 1101.

FIG. 6B shows the distal end 1133 of the needle 1130 disposed within the middle cannula 1120 such that the distal end 1133 does not extend beyond the distal end 1123 of the middle cannula 1120. The middle cannula 1120 is configured to shield the sharp distal end 1133 and prevent skiving of a wall of the lumen of the dilator 1101 during passage of the telescoping needle assembly 1000 through the curved portion of the dilator 1101. In certain instances, skived material from the dilator 1101 may be introduced into the patient's vasculature if the sharp distal end 1133 of the needle 1130 is exposed. The skived material may be a foreign body within the patient's body and result in unwanted morbidities, such as embolization, cysts, etc.

With continued reference to FIG. 6B, the telescoping needle assembly 1000 is loaded into the dilator 1101 until the distal end 1113 of the outer cannula 1110 abuts an internal shoulder 1105 adjacent the distal end 1103 of the dilator 1101. When abutting the internal shoulder 1105, the telescoping needle assembly 1000 is restricted from further advancement. A diameter of the lumen of the dilator 1101 distal to the internal shoulder 1105 is smaller than an outer diameter of the outer cannula 1110. The distal end 1123 of the middle cannula 1120 and the distal end 1133 of the needle 1130 extend beyond the distal end 1113 of the outer cannula 1110 and are positioned adjacent the distal end 1103 of the dilator 1101 but do not extend out of the dilator 1101.

FIG. 6A shows the locking member 1177 of the handle 1140 is in a locked state such that the notches 1183 of the distally extending cantilever arms 1182 are engaged with the distal detents 1145 of the upper housing 1141. In the locked state the button 1179 is positioned distally and the downward projection 1184 abuts against the vertical stop 1163 such that the outer cannula carriage 1158 and the middle cannula carriage 1166 are prevented from longitudinal movement.

FIGS. 7A and 7B illustrate the telescoping needle assembly 1000 in a needle extending state. FIG. 7A shows the locking member 1177 displaced proximally to an unlocked state. In the unlocked state, the button 1179 is positioned proximally. The distally extending cantilever arms 1182 are decoupled from the distal detents 1145. In some embodiments, the proximally extending cantilever arms 1182 may be coupled to the proximal detents 1144 such that the locking member 1177 is held in the unlocked state. The downward projection 1184 is displaced proximally away from contact with the outer cannula carriage 1158 such that the outer cannula carriage 1158 and the middle cannula carriage 1166 are not restricted from longitudinal movement. The clinician may grip the handle 1140 with one hand and grip a proximal portion of the dilator 1101 and the sheath 1102 with another hand. The handle 1140 may be displaced distally by the clinician. The upper housing 1141, the lower housing 1148, the locking member 1177, and the needle 1130 may be displaced distally relative to the dilator 1101 and the sheath 1102 to the needle extending state. The distal end 1133 of the needle 1130 is telescoped or extended beyond the distal end 1123 of the middle cannula 1120 to penetrate the atrial septum 1108. The distal end 1133 may extend beyond the distal end 1123 a distance ranging from 1 mm to 15 mm, from 5 mm to 15 mm, and from 5 mm to 10 mm. The outer cannula carriage 1158 and the middle cannula carriage 1166 may be configured to remain stationary relative to the dilator 1101 and the sheath 1102 because the distal end 1113 of the outer cannula 1110 abuts against the internal shoulder 1105 of the dilator 1101. The handle 1140 is displaced distally until the wings 1176 (not shown) of the middle cannula carriage 1166 contact the proximal stop 1192 such that the distal end 1133 of the needle 1130 extends beyond the distal end 1103 of the dilator 1101 and beyond the distal end 1123 of the outer cannula 1110. The relative position of the middle cannula 1120 to the outer cannula 1110 remains the same and as such, the gap 1164 remains between the middle cannula carriage 1166 and the distal portion 1161 of the outer cannula carriage 1158.

FIGS. 8A and 8B show the telescoping needle assembly 1000 in a middle cannula extending state and a needle extending state. The clinician may further displace the handle 1140 distally relative to the dilator 1101 and the sheath 1102. The distal end 1123 of the middle cannula 1120 is extending beyond the distal end 1103 of the dilator 1101 by the continued distal displacement of the handle 1140 by the clinician. The proximal stop 1192 is configured to engage with the wings 1176 and displace the middle cannula carriage 1166 distally while the outer cannula carriage 1158 remains stationary. Distal displacement of the middle cannula carriage 1166 results in closing of the gap 1164 and distal displacement of the middle cannula 1120 such that the distal end 1123 extends from the distal end 1103 of the dilator 1101 and at least partially through the atrial septum 1108. The middle cannula 1120 may extend from the dilator 1101 a distance ranging from about 1 mm to 15 mm, from 5 mm to 15 mm, and from 5 mm to 10 mm. The distal end 1123 and the needle 1130 extending from the dilator 1101 may provide guidance for the dilator 1101 and the sheath 1102 when they are advanced over the outer cannula 1110, the middle cannula 1120, and the needle 1130 through the atrial septum 1108. In some instances, following introduction of the dilator 1101 and the sheath 1102 into the left atrium, the dilator 1101 may be removed from the sheath 1102 and the sheath 1102 used for introduction of medical devices or instruments.

FIGS. 9-13B depict an embodiment of a telescoping needle assembly 1000' that resembles the telescoping needle assembly 1000 described above in certain respects. Accordingly, like features are designated with like reference numerals, with the "'" (prime) symbol added as a suffix. For example, the embodiment depicted in FIG. 9 includes a handle 1140' that may, in some respects, resemble the handle 1140 of FIG. 1. Relevant disclosure set forth above regarding similarly identified features thus may not be repeated hereafter. Moreover, specific features of the telescoping needle assembly 1000 and related components shown in FIGS. 1-8B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the telescoping needle assembly 1000' and related components depicted in FIGS. 9-13B. Any suitable combination of the features, and variations of the same, described with respect to the telescoping needle assembly 1000 and related components illustrated in FIGS. 1-8B can be employed with the telescoping needle assembly 1000' and related components of FIGS. 9-13B, and vice versa.

Figure 9:
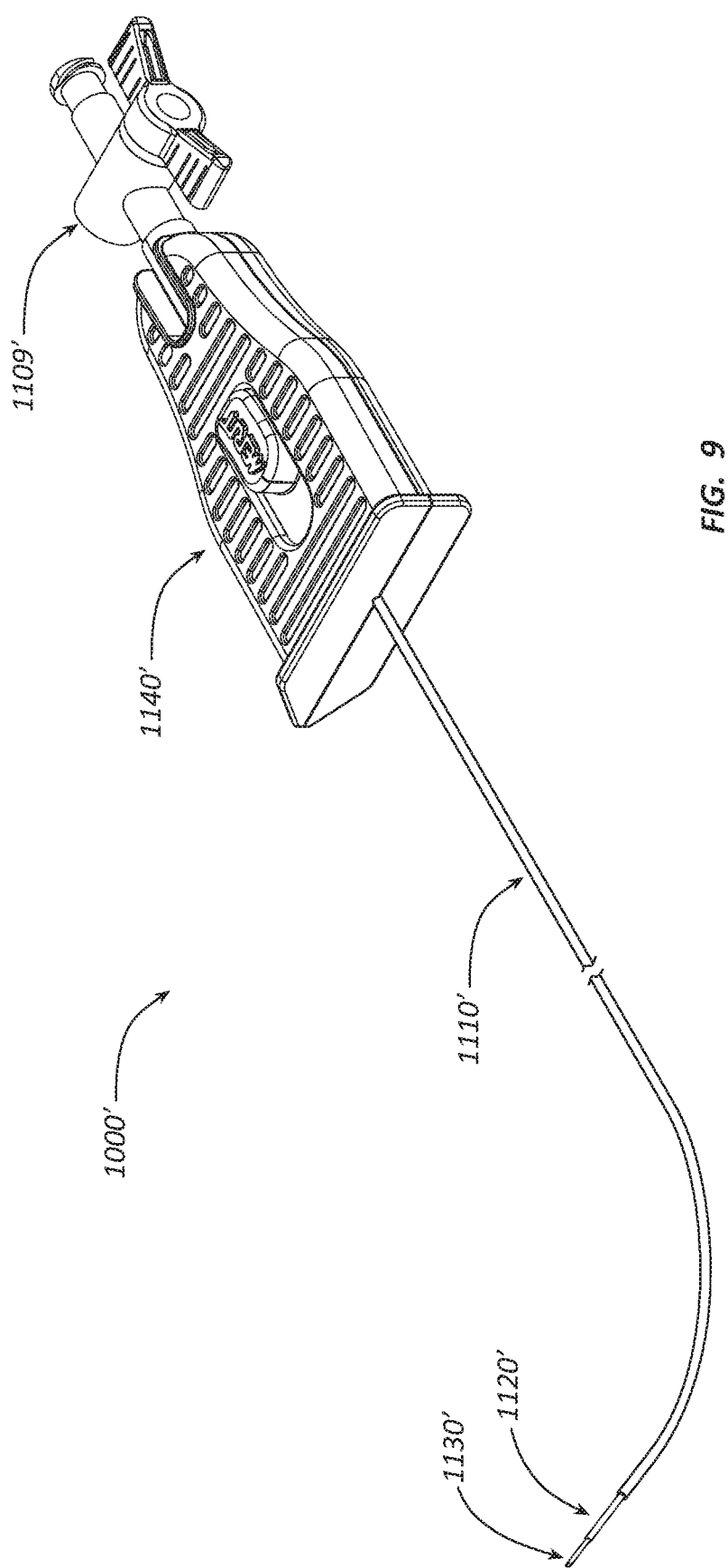
FIG. 9 is a perspective view of a telescoping needle assembly according to a second embodiment.

FIG. 9 depicts an embodiment of a telescoping needle assembly 1000'. In the illustrated embodiment, the telescoping needle assembly 1000' includes an outer cannula 1110', a middle cannula 1120', a needle 1130', and a handle 1140'. The needle assembly 1000' may also comprise a stopcock 1109'.

Figure 10A:
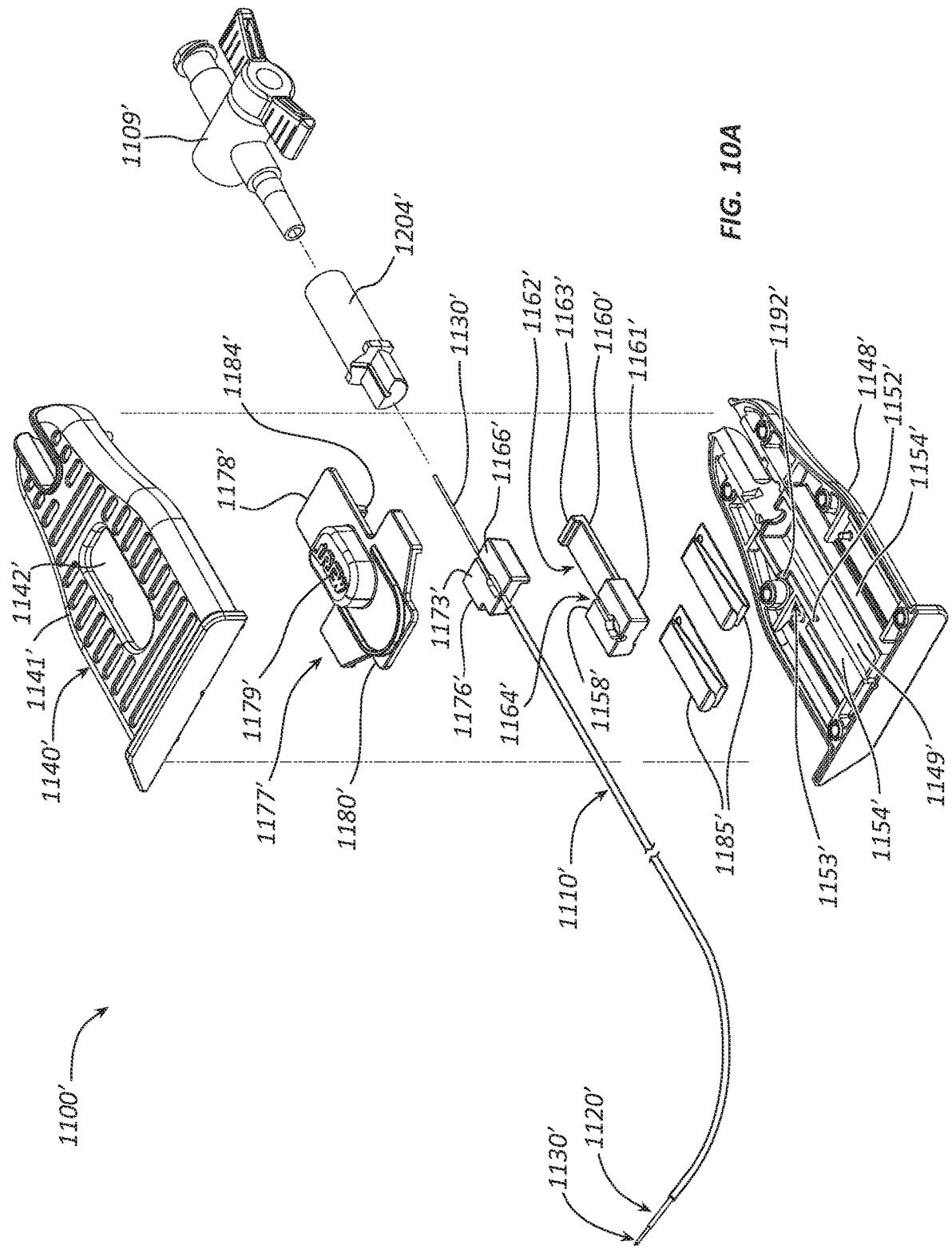
FIG. 10A is an exploded perspective top view of a handle of the telescoping needle assembly of FIG. 9.
Figure 10B:
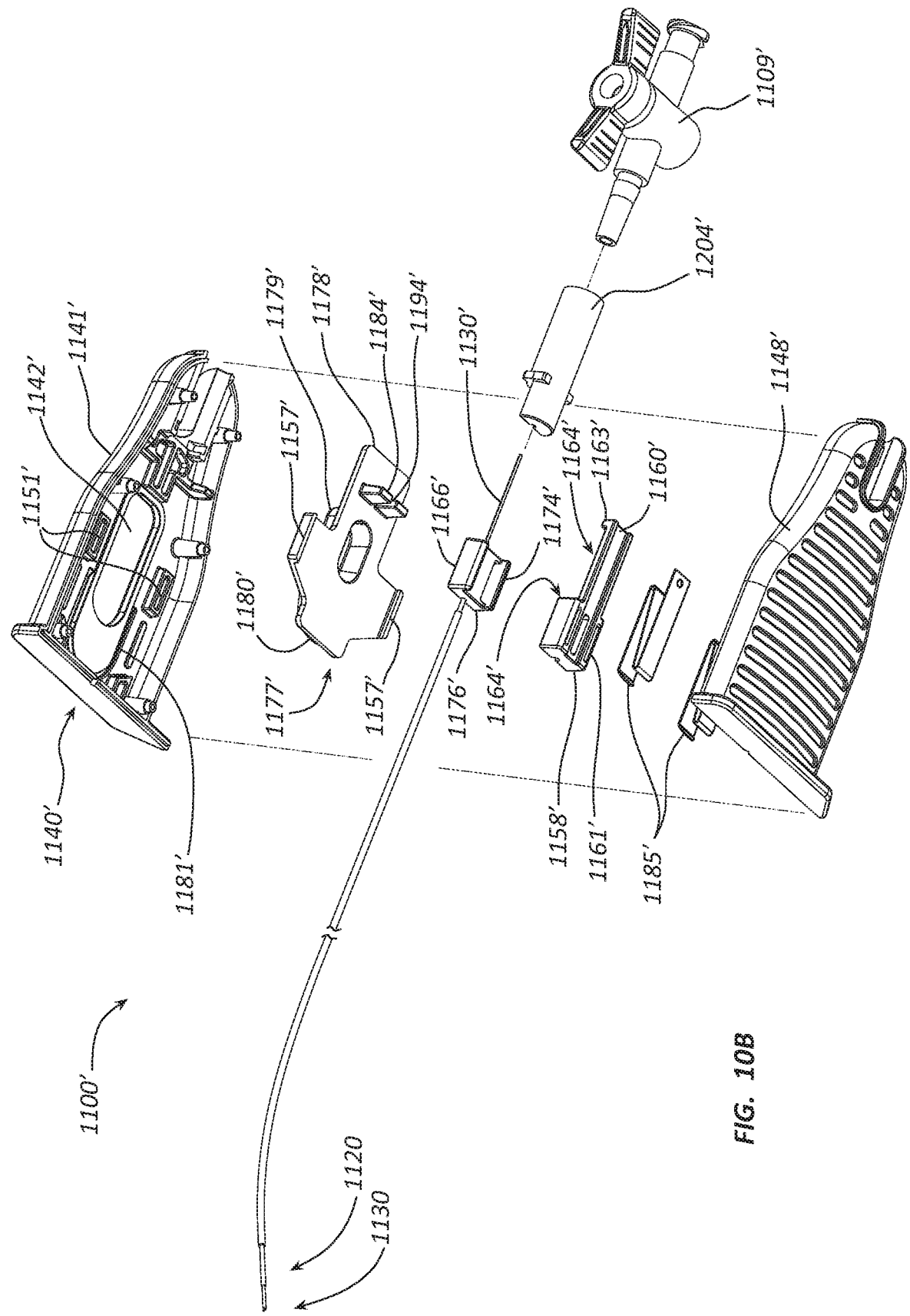
FIG. 10B is an exploded perspective bottom view of the handle of the telescoping needle assembly of FIG. 9.

FIGS. 10A and 10B illustrate exploded views of the handle 1140' of the telescoping needle assembly 1000'. In the illustrated embodiment, the handle 1140' includes an upper housing 1141', a lower housing 1148', an outer cannula carriage 1158', a middle cannula carriage 1166', and a locking member 1177'. As shown in FIGS. 10A and 10B, the upper housing 1141' is configured to couple with the lower housing 1148'. In the illustrated embodiment, the upper housing 1141' includes an elongate opening 1142'. The elongate opening 1142' is oriented with a longitudinal axis of the upper housing 1141' and is configured to slidingly receive a button 1179' of the locking member 1177'. The lower housing 1148' includes an elongate cavity 1149'. The cavity 1149' is oriented with a longitudinal axis of the lower housing 1148' and is configured to slidingly receive the outer cannula carriage 1158' and the middle cannula carriage 1166' between lateral side walls 1154' of the cavity 1149'. A notch 1153' formed in one lateral side wall 1154' defines a distal stop 1152' and a proximal stop 1192'.

The outer cannula carriage 1158' includes a distal portion 1161' and a proximal portion 1160'. The outer cannula carriage 1158' is configured to be slidingly disposed within the cavity 1149' between lateral side walls 1154'. The outer cannula 1110' may be fixedly coupled to the outer cannula carriage 1158'. The proximal portion 1160' includes a vertical stop 1163'. A recess 1162' is disposed between the distal portion 1161' and the vertical stop 1163'. The recess 1162 is configured to slidingly receive the middle cannula carriage 1166'.

The middle cannula carriage 1166' includes a body 1173'. The middle cannula carriage 1166' is configured to be slidingly disposed within the cavity 1149' and within the recess 1162' of the outer cannula carriage 1158' such that the middle cannula carriage 1166' is disposed between the distal portion 1161' and the vertical stop 1163'. A gap 1164' is defined between the middle cannula carriage 1166' and the distal portion 1161'. The middle cannula 1120' may be fixedly coupled to the middle cannula carriage 1166'. The body 1173' includes rails 1174' extending from a lower surface. The rails 1174' are configured to straddle a portion of the proximal portion 1160' of the outer cannula carriage 1158' and to slidingly couple with a bottom surface of the cavity 1149'. A laterally extending wing 1176' extends from the body 1173' and is disposed in the notch 1153' between the distal stop 1152' and the proximal stop 1192' such that the distal stop 1152' and the proximal stop 1192' limit longitudinal displacement of the middle cannula carriage 1166'.

The locking member 1177' includes the body 1178', an upward projection or button 1179', and a downward projection 1184'. The body 1178' is configured to slidingly engage the upper housing 1141'. The button 1179' extends vertically upward from the body 1178' and is configured to be received within the elongate opening 1142' of the upper housing 1141'. The button 1179' is configured to be engaged by a finger of a clinician to displace the locking member 1177' proximally or distally. The downward projection 1184' extends from a bottom surface of the body 1178' and is configured to be received within the cavity 1149' of the lower housing 1148'. The downward projection 1184' includes a slot or passage 1194' sized to slidingly receive the needle 1130'.

The handle 1140' may comprise one or more biasing members 1155' disposed between the lower housing 1148' and the locking member 1177' such that the one or more biasing members 1155' exerts an upward force to the locking member 1177'. In other words, the biasing members 1155 urge the locking member 1177' toward the upper housing 1141'. The upper housing 1141', lower housing 1148', locking member 1177', and one or more biasing members 1155' may be configured to provide for downward displacement of the locking member 1177' away from the upper housing 1141' in response to a downward force manually applied to the button 1179'. The one or more biasing members 1155' may be constructed as a leaf spring and may comprise a surface configured to slidably engage the locking member 1177'.

The locking member 1177' may comprise a raised rib 1180' extending upward from the body 1178' so as to engage (be received within) a correspondingly shaped rib recess 1181' in the upper housing 1141' in response to the upward force of the one or more biasing members 1155'. The raised rib 1180' and the rib recess 1181' may be positioned and configured to inhibit or prevent proximal displacement of the locking member 1177' away from a distal most position (the locked state) when the raised rib 1180' and the rib recess 1181' are engaged. In other words, the locking member 1177' is prevented from proximal displacement away from the locked state and toward the unlocked state unless the upward force of the one or more biasing members 1155' is overcome by a downward manual force applied to the button 1179', and the locking member 1177' is displaced downward resulting in disengagement of the raised rib 1180' from the rib recess 1181'.

The locking member 1177' may also comprise laterally extending wings 1157', and the upper housing 1141' may comprise downward protrusions 1151'. The downward protrusions 1151' may be positioned and configured to engage the laterally extending wings 1157' and inhibit or prevent proximal displacement of the locking member 1177' away from the locked state. The locking member 1177' is prevented from proximal displacement away from the locked state and toward the unlocked state unless the upward force of the one or more biasing members 1155' is overcome by a downward manual force applied to the button 1179', and the locking member 1177' is displaced downward resulting in disengagement of the laterally extending wings 1157' from the downward protrusions 1151'.

The needle 1130' may extend proximally through the handle 1140' and couple to a needle hub 1204'. A proximal end 1134' of the needle 1130' may be attached to the needle hub 1204' using any suitable technique, such as gluing, welding, insert molding, etc., such that, in some embodiments, the lumen 1132' of the needle 1130' is in fluid communication with a lumen extending through the needle hub 1204'. The needle hub 1204' may be disposed at least partially within and coupled to the handle 1140'. The needle hub 1204' may include a connector portion for coupling to a medical device, such as a stopcock 1109', syringe, medical connector, etc. to provide for fluid communication between the medical device and the lumen 1132'.

FIG. 11A illustrates a configuration of the handle 1140' and FIG. 11B illustrates the configuration of a distal end portion of the telescoping needle assembly 1000' in a loaded state. Referring to FIG. 11B, the dilator 1101' may be disposed within a lumen of a sheath 1102' such that a distal end 1103' of the dilator 1101' extends beyond a distal end 1104' of the sheath 1102'. FIG. 11B shows the distal end 1133' of the needle 1130' disposed within the middle cannula 1120' such that the distal end 1133' does not extend beyond the distal end 1123' of the middle cannula 1120'.

FIG. 11A shows the locking member 1177' of the handle 1140' in a locked state such that the raised rib 1180' is engaged with the rib recess 1181'. In the locked state, the button 1179' is positioned distally and the downward projection 1184' abuts against the vertical stop 1163' such that the outer cannula carriage 1158' and the middle cannula carriage 1166' are prevented from longitudinal movement.

Figure 12A:
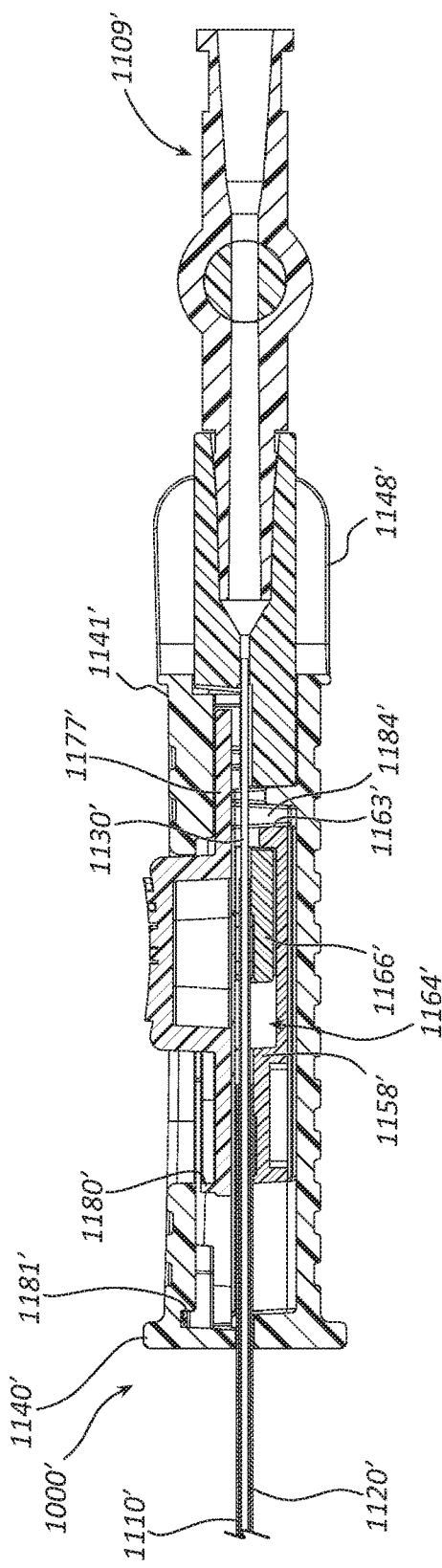
FIG. 12A is a longitudinal cross-sectional view of a proximal portion of the telescoping needle assembly of FIG. 9 in an unlocked state.
Figure 12B:
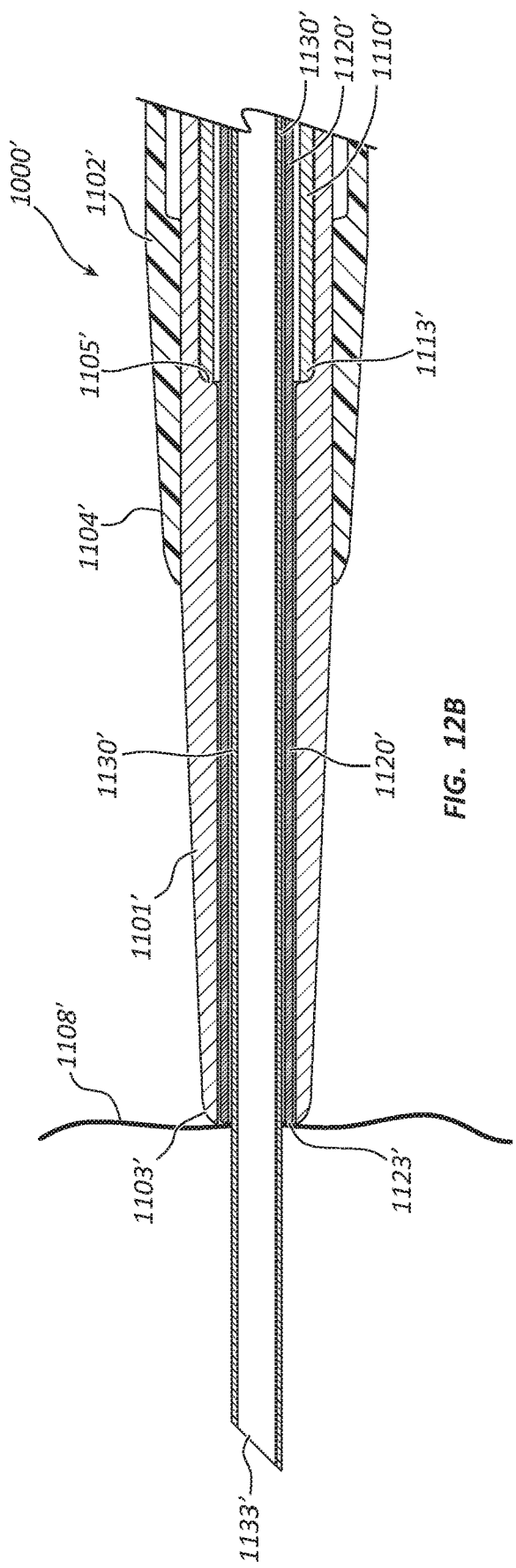
FIG. 12B is a longitudinal cross-sectional view of a distal portion of the telescoping needle assembly of FIG. 9 in a needle extending state.

FIGS. 12A and 12B illustrate the telescoping needle assembly 1000' in a needle extending state. FIG. 12A shows the locking member 1177' displaced proximally to an unlocked state. The raised rib 1180' is disengaged from the rib recess 1181'. The downward projection 1184' is displaced proximally such that the outer cannula carriage 1158' and the middle cannula carriage 1166' are not restricted from longitudinal movement. FIG. 12A also shows the middle cannula carriage 1166' proximally disposed to the relative position shown in FIG. 12B resulting in extension of the needle 1130' beyond the distal end 1123' of the middle cannula 1120'. FIG. 12A also shows the middle cannula carriage 1166' in the same position relative to the outer cannula carriage 1158' as shown in FIG. 11A. The gap 1164' remains between the middle cannula carriage 1166' and the distal portion 1161' of the outer cannula carriage 1158'.

Figure 13A:
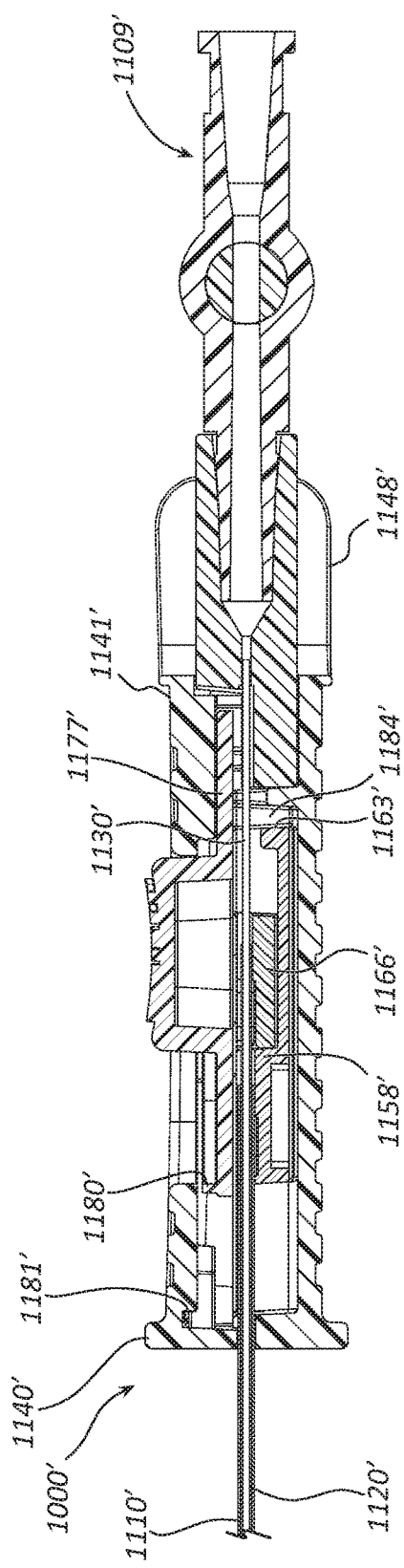
FIG. 13A is a longitudinal cross-sectional view of a proximal portion of the telescoping needle assembly of FIG. 9 in a middle cannula extending state.
Figure 13B:
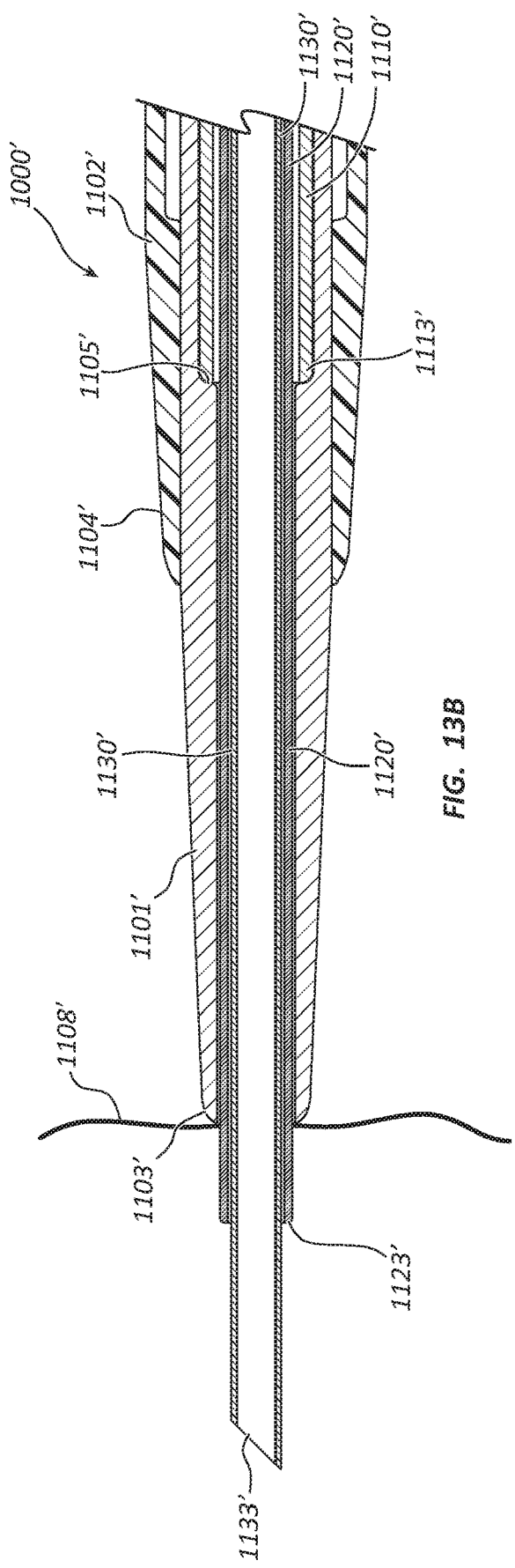
FIG. 13B is a longitudinal cross-sectional view of a distal portion of the telescoping needle assembly of FIG. 9 in a middle cannula extending state.

FIGS. 13A and 13B show the telescoping needle assembly 1000' in a middle cannula extending state and a needle extending state. The distal end 1133' of the needle 1130' is telescoped or extended beyond the distal end 1123' of the middle cannula 1120' to penetrate the atrial septum 1108'. The handle 1140' is further distally displaced and the outer cannula carriage 1158' remains stationary relative to the dilator 1101' and the sheath 1102' because the distal end 1113' of the outer cannula 1110' abuts against the internal shoulder 1105' of the dilator 1101'. The gap 1164' is reduced or eliminated between the middle cannula carriage 1166' and the distal portion 1161' of the outer cannula carriage 1158'.

In the illustrated needle extending state, the distal end 1123' of the middle cannula 1120' is extending beyond the distal end 1103' of the dilator 1101' by the continued distal displacement of the handle 1140' by the clinician. The wing 1176' (not shown) is in contact with the proximal stop 1192' (not shown) preventing further distal displacement of the needle 1130' relative to the middle cannula 1120' while the middle cannula 1120' is further distally displaced relative to outer cannula 1110' causing the gap 1164' between the middle cannula carriage 1166' and the distal portion 1161' of the outer cannula carriage 1158' to be eliminated. Distal displacement of the middle cannula carriage 1166' results in distal displacement of the middle cannula 1120' such that the distal end 1123' extends from the distal end 1103 of the dilator 1101 and at least partially through the atrial septum 1108.

FIGS. 14-18B depict an embodiment of a telescoping needle assembly 2000 that resembles the telescoping needle assembly 1000 described above in certain respects. Accordingly, like features are designated with like reference numerals, with the leading digit incremented to "2." For example, the embodiment depicted in FIG. 14 includes a handle 2140 that may, in some respects, resemble the handle 1140 of FIG. 1. Relevant disclosure set forth above regarding similarly identified features thus may not be repeated hereafter. Moreover, specific features of the telescoping needle assembly 1000 and related components shown in FIGS. 1-8B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the telescoping needle assembly 2000 and related components depicted in FIGS. 14-18B. Any suitable combination of the features, and variations of the same, described with respect to the telescoping needle assembly 1000 and related components illustrated in FIGS. 1-8B can be employed with the telescoping needle assembly 2000 and related components of FIGS. 14-18B, and vice versa. This pattern of disclosure applies equally to further embodiments depicted in subsequent figures and described hereafter, wherein the leading digits may be further incremented.

Figure 14:
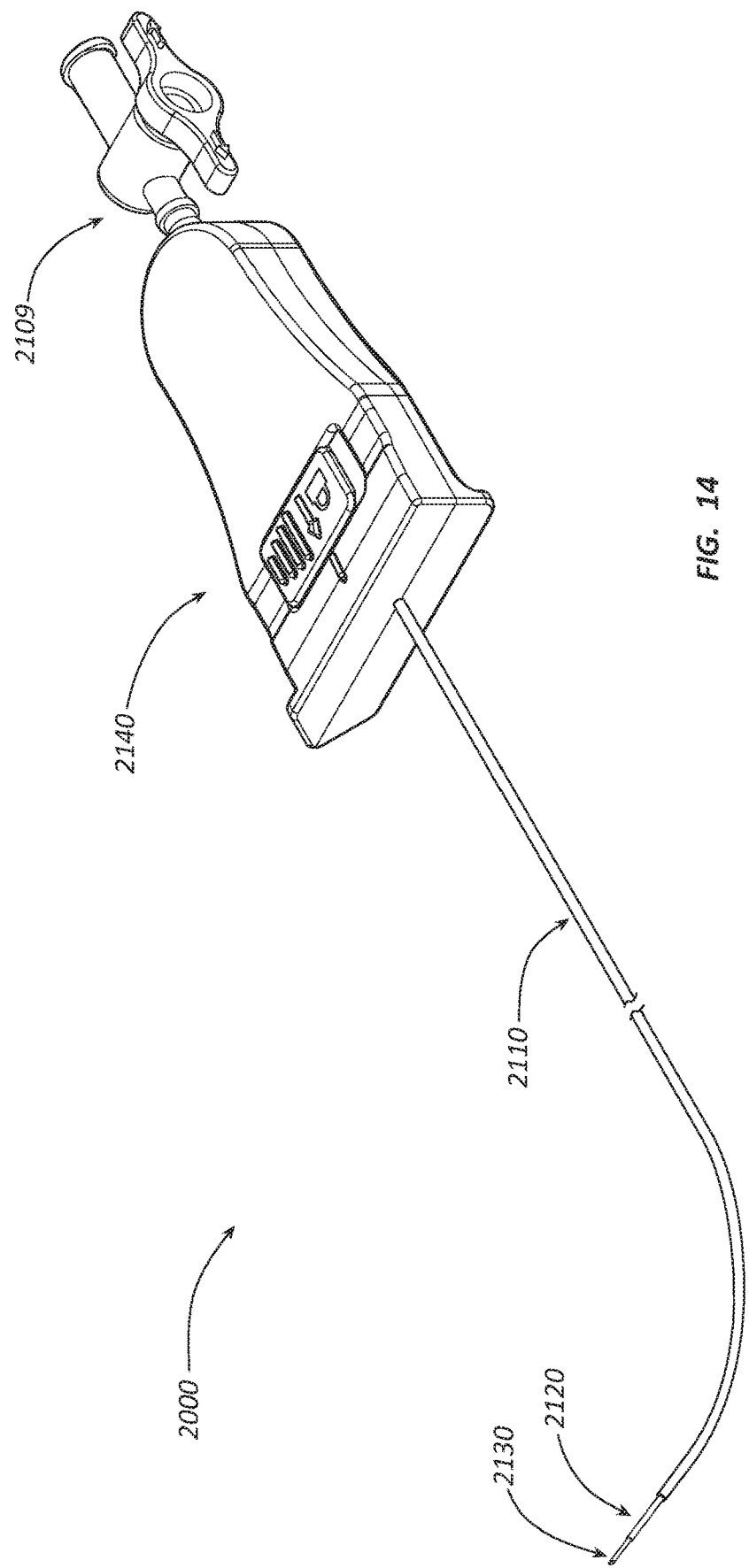
FIG. 14 is a perspective view of a telescoping needle assembly according to a third embodiment.

FIGS. 14-18B depict an embodiment of the telescoping needle assembly 2000. As shown in the embodiment of FIG. 14, the telescoping needle assembly 2000 includes an outer cannula 2110, a middle cannula 2120, a needle 2130, and a handle 2140.

Figure 15A:
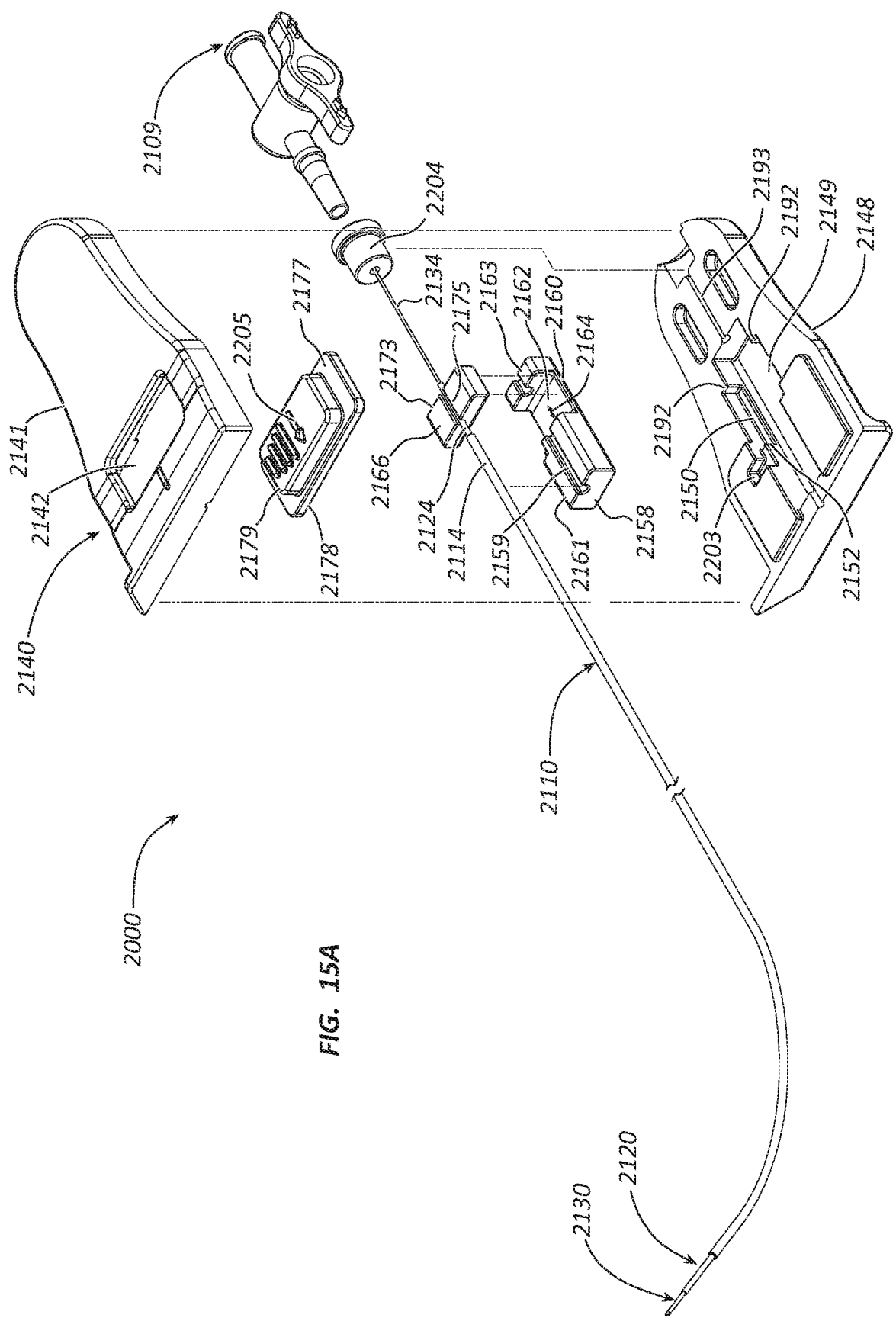
FIG. 15A is an exploded perspective top view of a handle of the telescoping needle assembly of FIG. 14.
Figure 15B:
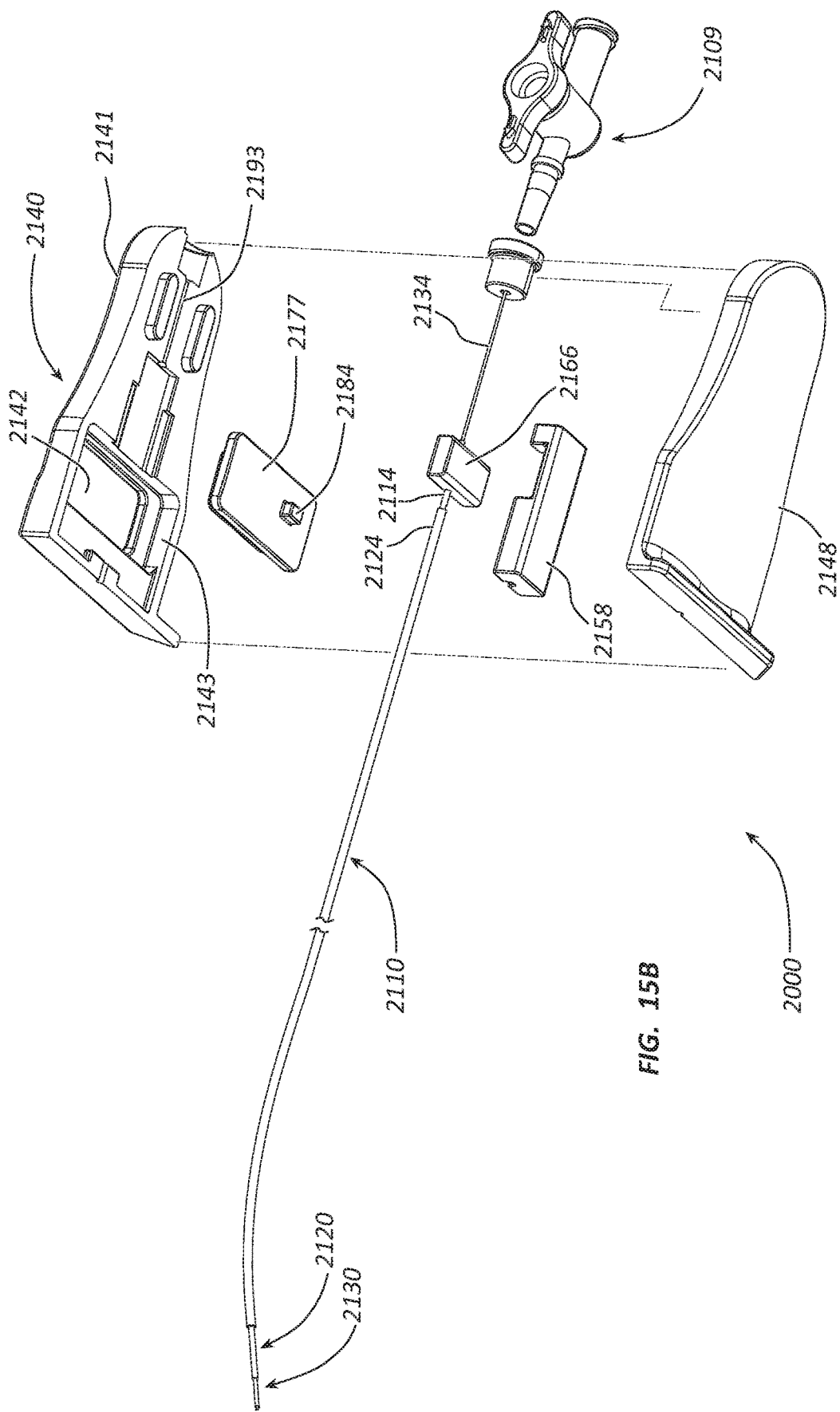
FIG. 15B is an exploded perspective bottom view of the handle of the telescoping needle assembly of FIG. 14.

FIGS. 15A and 15B illustrate exploded perspective views of the handle 2140. As illustrated in the embodiment of FIGS. 15A and 15B, the handle 2140 includes an upper housing 2141, an outer cannula carriage 2158, a middle cannula carriage 2166, and a locking member 2177.

The upper housing 2141 may be configured to couple with a lower housing 2148. The upper housing 2141 includes an elongate opening 2142 and a recess 2143 disposed on a bottom surface. The elongate opening 2142 may be oriented transverse to a longitudinal axis of the upper housing 2141 and may be configured to slidingly receive a button 2179 of the locking member 2177. The recess 2143 may be elongated and configured to slidingly receive a portion of the locking member 2177.

With continued reference to the embodiment illustrated in FIGS. 15A and 15B, the lower housing 2148 may be configured to couple with the upper housing 2141. The lower housing 2148 includes an elongate cavity 2149. The cavity 2149 is oriented with a longitudinal axis of the lower housing 2148 and is configured to slidingly receive the outer cannula carriage 2158 and the middle cannula carriage 2166. The cavity 2149 may be configured with a wide upper portion and a narrow lower portion. A pair of shelves 2150 may be disposed on lateral sides of the cavity 2149 and divide the upper portion from the lower portion. The shelves 2150 include inwardly extending distal stops 2152 and proximal stops 2192. Extending orthogonally and laterally from one side of a distal end of the upper portion of the cavity 2149 is a slot 2203 that may be configured to slidingly receive a downward projection 2184 of the locking member 2177.

The outer cannula carriage 2158 includes a proximal portion 2160 and a distal portion 2161. The outer cannula carriage 2158 may be configured to be slidingly disposed within the cavity 2149. The distal portion 2161 comprises a channel 2159 extending longitudinally through an upper surface. The channel 2159 may be sized to receive a proximal end 2114 of the outer cannula 2110. The proximal end 2114 may be fixedly coupled to the outer cannula carriage 2158 using any suitable technique, such as gluing, welding, insert molding, etc. The proximal portion 2160 includes a vertical stop 2163. A recess 2162 is disposed between the distal portion 2161 and the vertical stop 2163. The recess 2162 may be configured to slidingly receive the middle cannula carriage 2166. The outer cannula carriage 2158 may be formed of any suitable rigid or semi-rigid thermoplastic material, such as polycarbonate, polypropylene, polyethylene, polyvinylchloride, etc.

The middle cannula carriage 2166 includes a body 2173. The middle cannula carriage 2166 may be configured to be slidingly disposed within the cavity 2149 and within the recess 2162 of the outer cannula carriage 2158 such that the middle cannula carriage 2166 is disposed between the distal portion 2161 and the vertical stop 2163. A gap 2164 may be defined between the distal portion 2161 of the outer cannula carriage 2158 and the middle cannula carriage 2166. The body 2173 comprises a channel 2175 extending longitudinally through an upper surface. The channel 2175 may be sized to receive a proximal end 2124 of the middle cannula 2120. The proximal end 2124 may be fixedly coupled to the middle cannula carriage 2166 using any suitable technique, such as gluing, welding, insert molding, etc. Laterally extending portions or wings 2176 extend from the body 2173 and are disposed over the shelves 2150.

The needle 2130 may extend through a channel 2193 disposed in the handle 2140. A proximal end 2134 of the needle 2130 may be coupled to a needle hub 2204. The needle hub 2204 may be disposed at least partially within the handle 2140 and include a connector portion for coupling to a medical device, such as a stopcock 2109, syringe, medical connector, etc. In other embodiments, the proximal end 2134 of the needle 2130 may be fixedly coupled to the channel 2193 using any suitable technique, such as gluing, welding, insert molding, etc.

The locking member 2177 includes a body 2178, the upward projection or button 2179, and the downward projection 2184. The body 2178 may be configured to be slidingly received within the recess 2143 of the upper housing 2141 and to slidingly couple with an upper surface of the lower housing 2148. The button 2179 extends vertically upward from the body 2178 and may be configured to be received within the elongate opening 2142 of the upper housing 2141. The button 2179 may be configured to be engaged by a finger of a clinician to displace the locking member 2177 transversely from a locked state to an unlocked state. The button 2179 may include gripping features to facilitate displacement by the finger of the clinician. The features may include ribs, bumps, dimples, textured surface, slip resistant material, etc. In some embodiments, the button 2179 may include an indicium 2205, such as an arrow or any other suitable indicium, to indicate whether the handle 2140 is in the locked or unlocked state. The downward projection 2184 extends from a bottom surface of the body 2178 and may be configured to be displaceably received within the slot 2203 of the lower housing 2148.

Figure 16A:
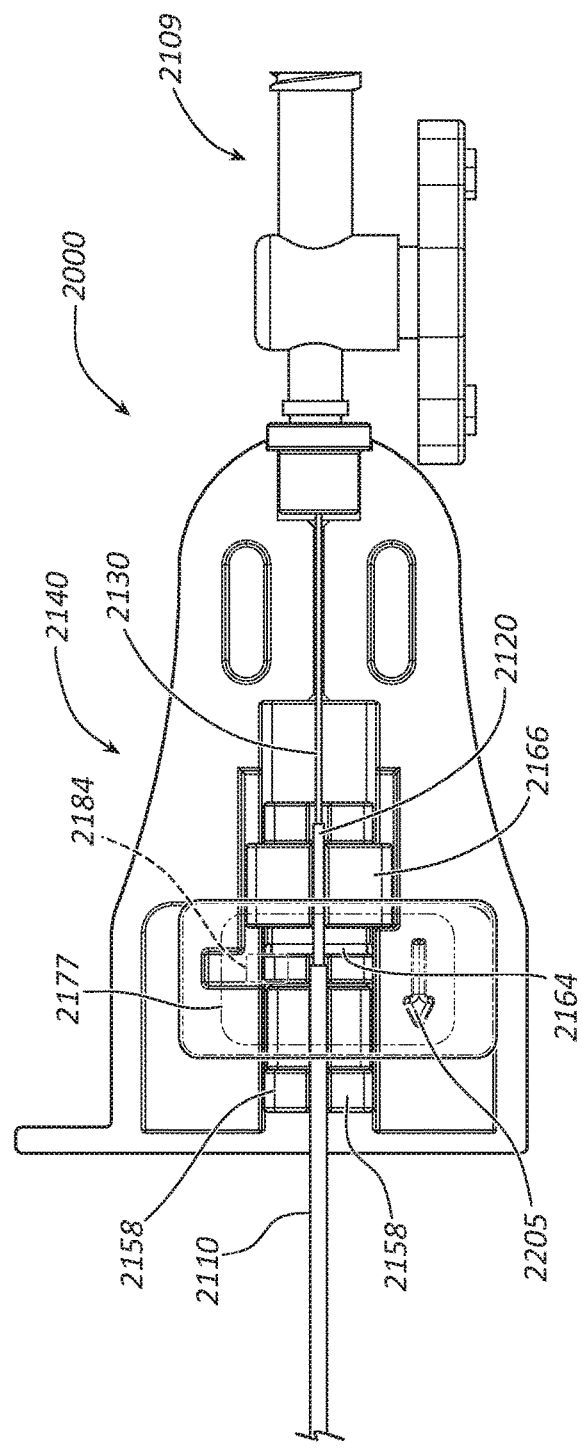
FIG. 16A is a longitudinal cross-sectional view of a proximal portion of the telescoping needle assembly of FIG. 14 in a locked state.
Figure 16B:
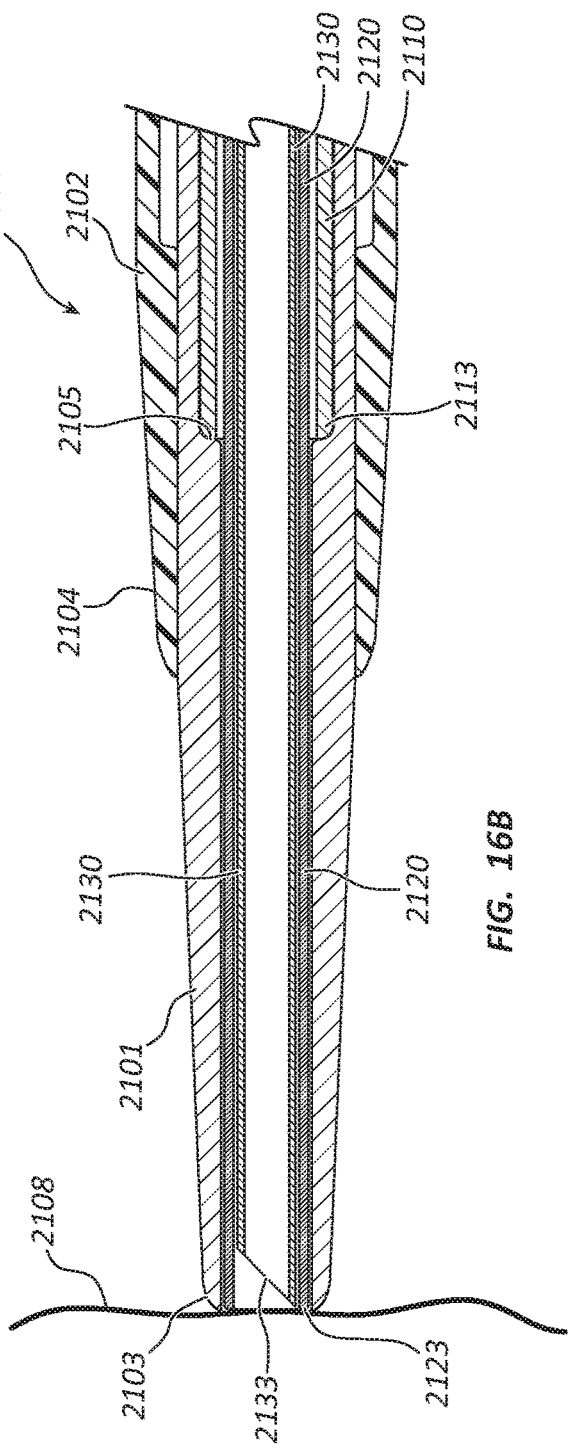
FIG. 16B is a longitudinal cross-sectional view of a distal portion of the telescoping needle assembly of FIG. 14 in a cannula loaded state.

In use, FIG. 16A illustrates a configuration of the handle 2140 in the locked state and FIG. 16B illustrates the configuration of a distal end portion of the telescoping needle assembly 2000 in a loaded state. FIG. 16B shows the telescoping needle assembly 2000 loaded into a dilator 2101 until a distal end 2113 of the outer cannula 2110 abuts an internal shoulder 2105 adjacent the distal end 2103 of the dilator 2101. When abutting the internal shoulder 2105, the telescoping needle assembly 2000 may be restricted from further advancement. A diameter of the lumen of the dilator 2101 distal to the internal shoulder 2105 is smaller than an outer diameter of the outer cannula 2110. A distal end 2123 of the middle cannula 2120 and a distal end 2133 of the needle 2130 extend beyond the distal end 2113 and may be positioned adjacent the distal end 2103 of the dilator 2101 but do not extend out of the dilator 2101 in a loaded state.

As shown in FIG. 16A, the locking member 2177 of the handle 2140 is in a locked state. In the locked state, the button 2179 may be positioned such that the indicium 2205 is not aligned with a longitudinal axis of the handle 2140. The downward projection 2184 may abut against the outer cannula carriage 2158 to prevent longitudinal displacement.

FIG. 17A illustrates a configuration of the handle 2140 in the unlocked state, and FIG. 17B illustrates the configuration of a distal end portion of the telescoping needle assembly 2000 in a needle extending state. The button 2179 of the locking member 2177 may be displaced laterally by the clinician such that the indicium 2205 aligns with the longitudinal axis of the handle 2140. The downward projection 2184 may be displaced laterally into the slot 2203 such that the outer cannula carriage 2158 is not blocked from longitudinal movement.

FIG. 17B shows the distal end 2133 of the needle 2130 may be displaced distally to penetrate an atrial septum 2108 when the clinician grips the handle 2140 with one hand and grips a proximal portion of the dilator 2101 and a sheath 2102 with the other hand. The upper housing 2141, the lower housing 2148, the locking member 2177, and the needle 2130 may be displaced distally relative to the dilator 2101 and the sheath 2102. The distal end 2133 of the needle 2130 may extend beyond the distal end 2123 of the middle cannula 2120 to penetrate the atrial septum 2108. The outer cannula carriage 2158 and the middle cannula carriage 2166 may be configured to remain stationary relative to the dilator 2101 and the sheath 2102 because the distal end 2113 of the outer cannula 2110 abuts against the internal shoulder 2105 of the dilator 2101, the outer cannula 2110 may be fixedly coupled to the outer cannula carriage 2158, and the middle cannula 2120 may be fixedly coupled to the middle cannula carriage 2166. The handle 2140 may be displaced distally until the wings 2176 of the middle cannula carriage 2166 contact the proximal stops 2192. The gap 2164 may remain between the middle cannula carriage 2166 and the distal portion 2161 of the outer cannula carriage 2158.

Figure 18A:
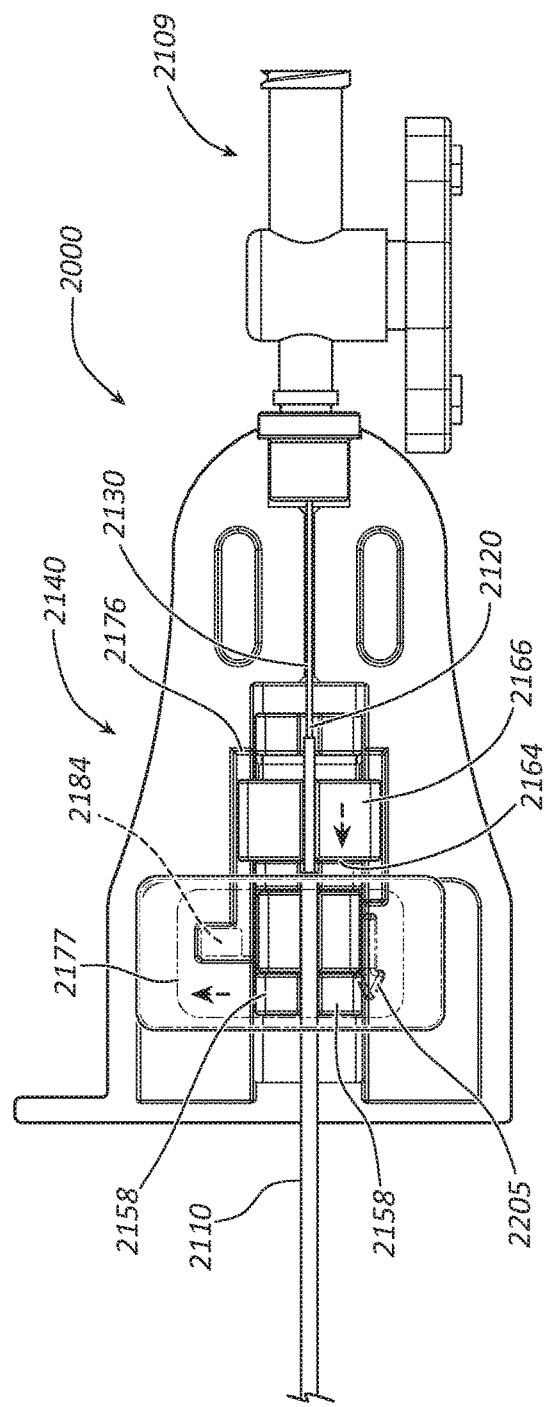
FIG. 18A is a longitudinal cross-sectional view of a proximal portion of the telescoping needle assembly of FIG. 14 in a middle cannula extending state.
Figure 18B:
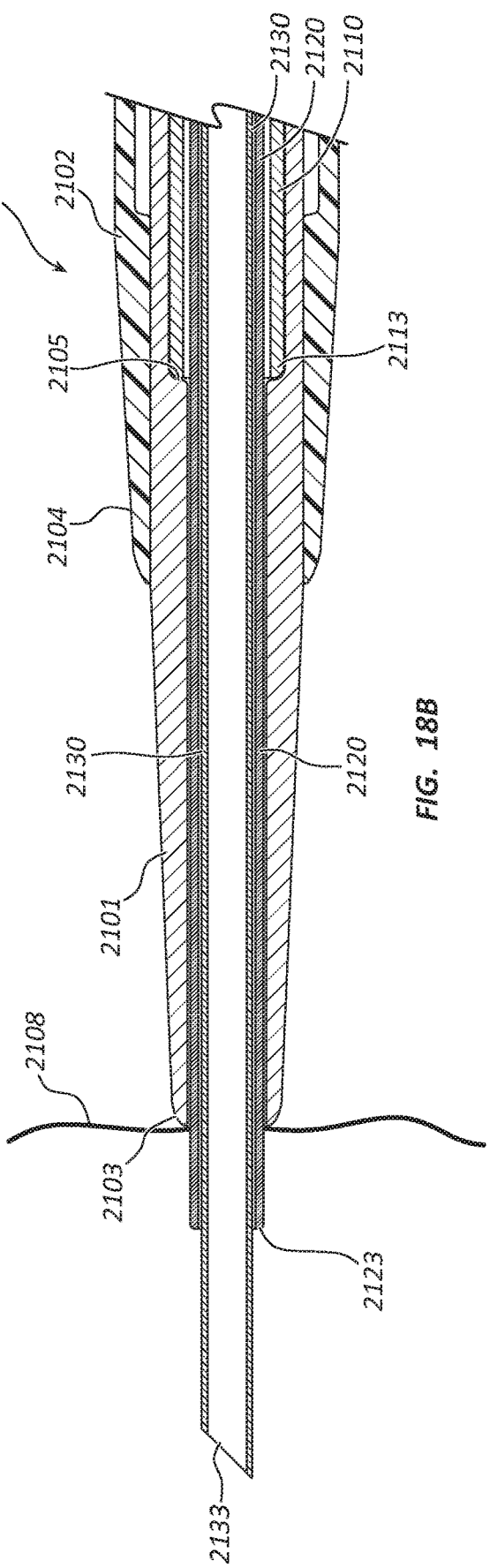
FIG. 18B is a longitudinal cross-sectional view of a distal portion of the telescoping needle assembly of FIG. 14 in a middle cannula extending state.

FIGS. 18A and 18B show the telescoping needle assembly 2000 in a middle cannula extending state. The distal end 2123 of the middle cannula 2120 may extend beyond the distal end 2103 of the dilator 2101 by continued distal displacement of the handle 2140. The proximal stop 2192 may be configured to engage with the wings 2176 and displace the middle cannula carriage 2166 distally while the outer cannula carriage 2158 remains stationary. Distal displacement of the middle cannula carriage 2166 may result in closing of the gap 2164 and distal displacement of the middle cannula 2120 such that the distal end 2123 may extend at least partially through the atrial septum 2108.

FIGS. 19-23B depict an embodiment of a telescoping needle assembly 2000' that resembles the telescoping needle assembly 2000 described above in certain respects. Accordingly, like features are designated with like reference numerals, with the "'" (prime) symbol added as a suffix. For example, the embodiment depicted in FIG. 19 includes a handle 2140' that may, in some respects, resemble the handle 2140 of FIG. 14. Relevant disclosure set forth above regarding similarly identified features thus may not be repeated hereafter. Moreover, specific features of the telescoping needle assembly 2000 and related components shown in FIGS. 19-23B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the telescoping needle assembly 2000' and related components depicted in FIGS. 19-23B. Any suitable combination of the features, and variations of the same, described with respect to the telescoping needle assembly 2000 and related components illustrated in FIGS. 14-18B can be employed with the telescoping needle assembly 2000' and related components of FIGS. 19-23B, and vice versa.

Figure 19:
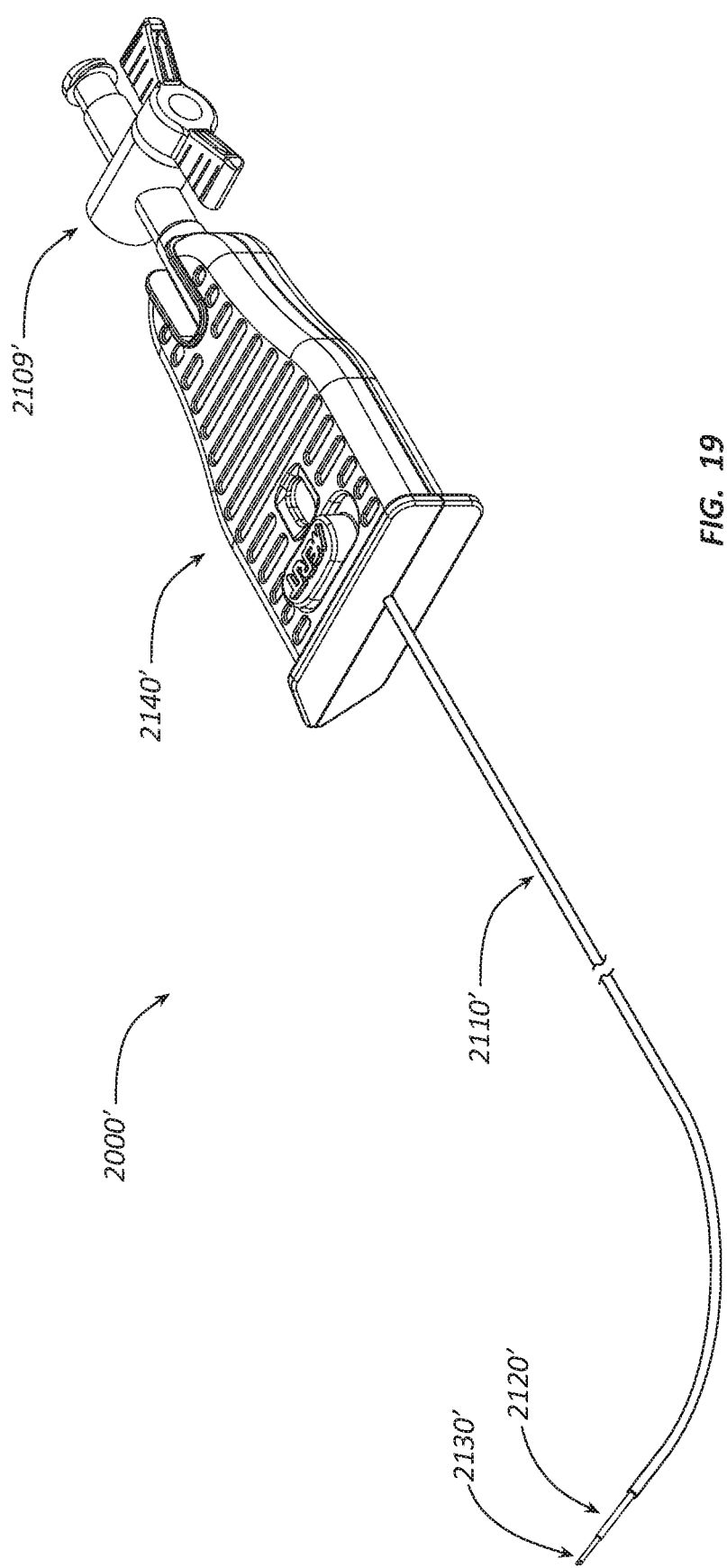
FIG. 19 is a perspective view of a telescoping needle assembly according to a fourth embodiment.

FIGS. 19-23B depict an embodiment of the telescoping needle assembly 2000'. As shown in the embodiment of FIG. 19, the telescoping needle assembly 2000' includes an outer cannula or first elongate member 2110', a middle cannula or second elongate member 2120', an inner cannula or needle 2130', and a handle 2140'.

Figure 20A:
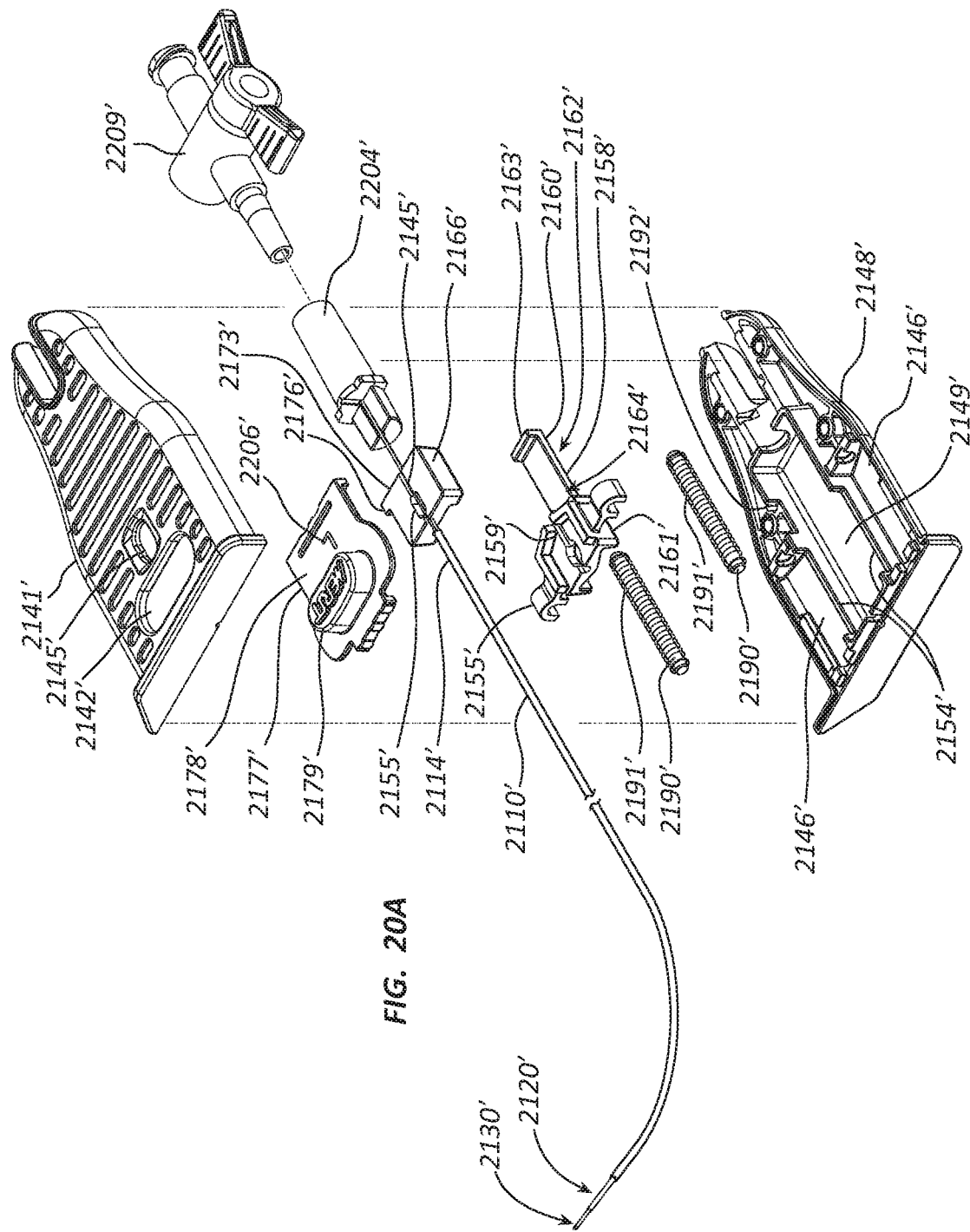
FIG. 20A is an exploded perspective top view of a handle of the telescoping needle assembly of FIG. 19.
Figure 20B:
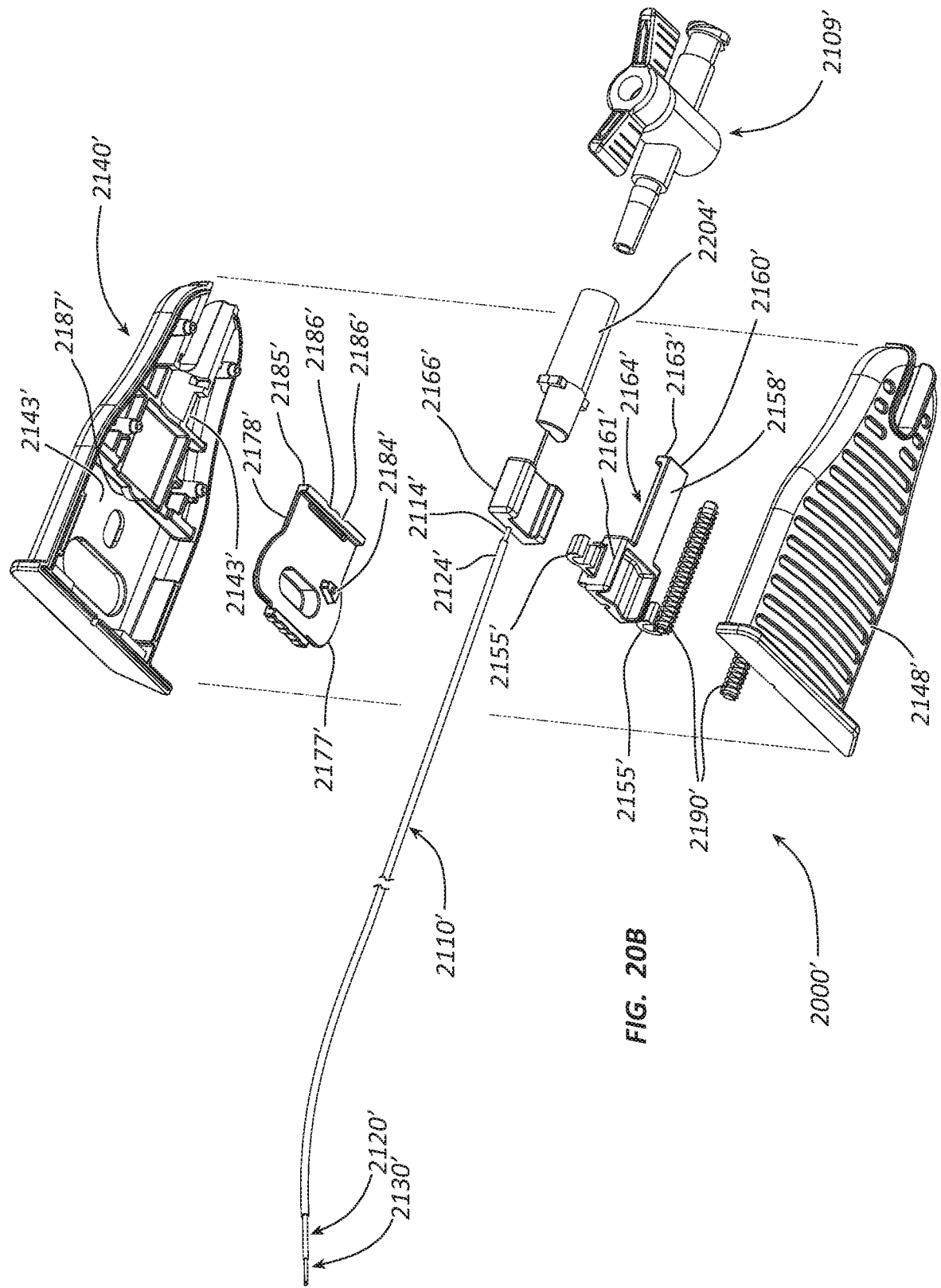
FIG. 20B is an exploded perspective bottom view of the handle of the telescoping needle assembly of FIG. 19.

FIGS. 20A and 20B illustrate exploded perspective views of the handle 2140'. As illustrated in the embodiment of FIGS. 20A and 20B, the handle 2140' includes an upper housing 2141', an outer cannula carriage 2158', a middle cannula carriage 2166', and a locking member 2177'.

The upper housing 2141' may be configured to couple with a lower housing 2148'. The upper housing 2141' includes an elongate opening 2142' and a recess 2143' disposed on a bottom surface. The elongate opening 2142' may be oriented transverse to a longitudinal axis of the upper housing 2141' and may be configured to slidingly receive a button 2179' of the locking member 2177'. The recess 2143' may be elongated and configured to slidingly receive a portion of the locking member 2177'.

The upper housing 2141' may comprise a window 2145' to provide for visibility of indicia 2206' disposed on the locking member 2177'. The indicia 2206' may indicate the status of the locking member 2177', i.e., locked vs. unlocked.

With continued reference to the embodiment illustrated in FIGS. 20A and 20B, the lower housing 2148' may be configured to couple with the upper housing 2141'. The lower housing 2148' includes an elongate cavity 2149'. The cavity 2149' is oriented with a longitudinal axis of the lower housing 2148' and is configured to slidingly receive the outer cannula carriage 2158' and the middle cannula carriage 2166'. A pair of opposing walls 2154' may be disposed on lateral sides of the cavity 2149'. A notch 2153' may be formed in one wall 2154' defining a distal stop 2152' and a proximal stop 2192'.

A pair of rods 2190' may be disposed within lateral pockets 2146' of the lower housing 2148'. The lateral pockets 2146' may comprise end portions configured to engage the ends of the rods 2190' so that the rods 2190' are constrained in a parallel orientation. Coil springs 2191' may be disposed on the rods 2190' as further described below.

The outer cannula carriage 2158' includes a distal portion 2161' and a proximal portion 2160'. The outer cannula carriage 2158' may be configured to be slidingly disposed within the cavity 2149'. The distal portion 2161' comprises a channel 2159' extending longitudinally through an upper surface. The channel 2159' may be sized to receive a proximal end 2114' of the outer cannula 2110'. The proximal end 2114' may be fixedly coupled to the outer cannula carriage 2158' using any suitable technique, such as gluing, welding, insert molding, etc. The proximal portion 2160' includes a vertical stop 2163'. A recess 2162' is disposed between the distal portion 2161' and the vertical stop 2163'. The recess 2162' may be configured to slidingly receive the middle cannula carriage 2166'.

The outer cannula carriage 2158' may comprise lateral extensions 2155' configured to slidingly engage the rods 2190'. As such, the rods 2190' may constrain lateral displacement of the outer cannula carriage 2158' while allowing longitudinal displacement. The coil springs 2191' may be disposed between the lateral extensions 2155' and proximal end portions of the lateral pockets 2146' such that the coil springs 2191' exert a distal force on the lateral extensions 2155' urging the outer cannula carriage 2158' in the distal direction.

The middle cannula carriage 2166' includes a body 2173'. The middle cannula carriage 2166' may be configured to be slidingly disposed within the cavity 2149' and within the recess 2162' of the outer cannula carriage 2158' such that the middle cannula carriage 2166' is disposed between the proximal portion 2160' and the vertical stop 2163'. A gap 2164' may be defined between the distal portion 2161' of the outer cannula carriage 2158' and the middle cannula carriage 2166'. The body 2173' comprises a channel 2175' extending longitudinally through an upper surface. The channel 2175' may be sized to receive a proximal end 2124' of the middle cannula 2120'. The proximal end 2124' may be fixedly coupled to the middle cannula carriage 2166' using any suitable technique, such as gluing, welding, insert molding, etc. A laterally extending wing 2176' extends from the body 2173' and is disposed within the notch 2153'.

A proximal end 2134' of the needle 2130' may be coupled to a needle hub 2204'. The needle hub 2204' may be disposed at least partially within the handle 2140' and include a connector portion for coupling to a medical device, such as a stopcock 2109', syringe, medical connector, etc.

The locking member 2177' includes a body 2178', a button 2179', and a downward projection 2184'. The body 2178' may be configured to be slidingly received within the recess 2143' of the upper housing 2141'. The button 2179' extends vertically upward from the body 2178' and may be configured to be received within the elongate opening 2142' of the upper housing 2141'. The button 2179' may be configured to be engaged by a finger of a clinician to displace the locking member 2177' transversely from a locked state (one end of the elongate opening 2142') to an unlocked state (the other end of the elongate opening 2142'). The downward projection 2184' extends from a bottom surface of the body 2178' and is configured to engage the outer cannula carriage 2158' thereby preventing longitudinal displacement of the outer cannula carriage 2158' when the locking member 2177' is in the locked state.

Displacement of the button 2179' away from the locked state and the unlocked state may be partially inhibited by detents as described below. The locking member 2177' may comprise a proximal wall 2185' extending downward from the bottom surface of the body 2178'. A gap between a central portion of the proximal wall 2185' and the body 2178' may provide for flexibility of the central portion of the proximal wall 2185'. The proximal wall 2185' may comprise a pair of recesses 2186' disposed on a proximal surface. The recesses 2186' may be configured to engage a corresponding protrusion 2187' disposed on the bottom surface of the upper housing 2141'. When the locking member 2177' is in the locked state, the protrusion 2187' may be disposed within one recess 2186' and when the locking member 2177' is in the unlocked state, the protrusion 2187' may be disposed within the other recess 2186'. During transition from the locked state to the unlocked state, the central portion of the proximal wall 2185' may flex distally so as to allow the protrusion 2187' to be displaced from the one recess 2186' to the other recess 2186'.

In use, FIG. 21A illustrates a configuration of the handle 2140' in the locked state and FIG. 21B illustrates the configuration of a distal end portion of the telescoping needle assembly 2000' in a loaded state. FIG. 21B shows the telescoping needle assembly 2000' is loaded into a dilator 2101' until a distal end 2113' of the outer cannula 2110' abuts an internal shoulder 2105' adjacent the distal end 2103' of the dilator 2101'. When abutting the internal shoulder 2105', the telescoping needle assembly 2000' may be restricted from further advancement. A diameter of the lumen of the dilator 2101' distal to the internal shoulder 2105' is smaller than an outer diameter of the outer cannula 2110'. A distal end 2123' of the middle cannula 2120' and a distal end 2133' of the needle 2130' extend beyond the distal end 2113' and may be positioned adjacent the distal end 2103' of the dilator 2101' but do not extend out of the dilator 2101' in a loaded state. As shown in FIG. 21A, the locking member 2177' of the handle 2140' is in a locked state. In the locked state, the button 2179' may be positioned laterally to one end of the elongate opening 2142'. The downward projection 2184' may abut against the outer cannula carriage 2158' to prevent longitudinal displacement in the proximal direction.

Figure 22A:
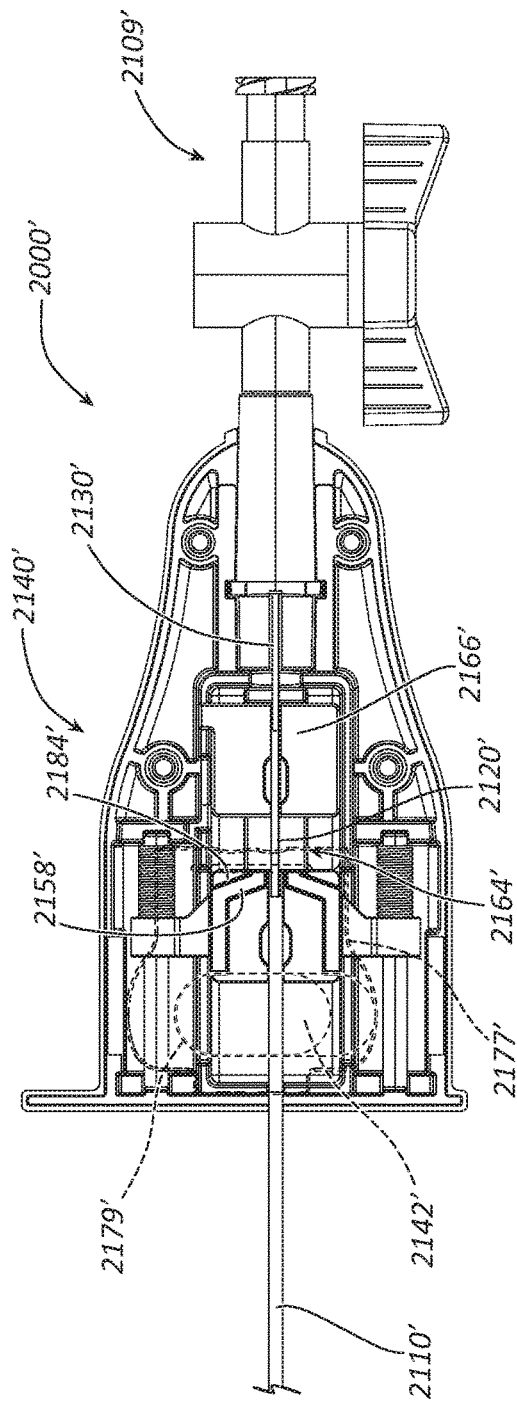
FIG. 22A is a longitudinal cross-sectional view of a proximal portion of the telescoping needle assembly of FIG. 19 in an unlocked state.
Figure 22B:
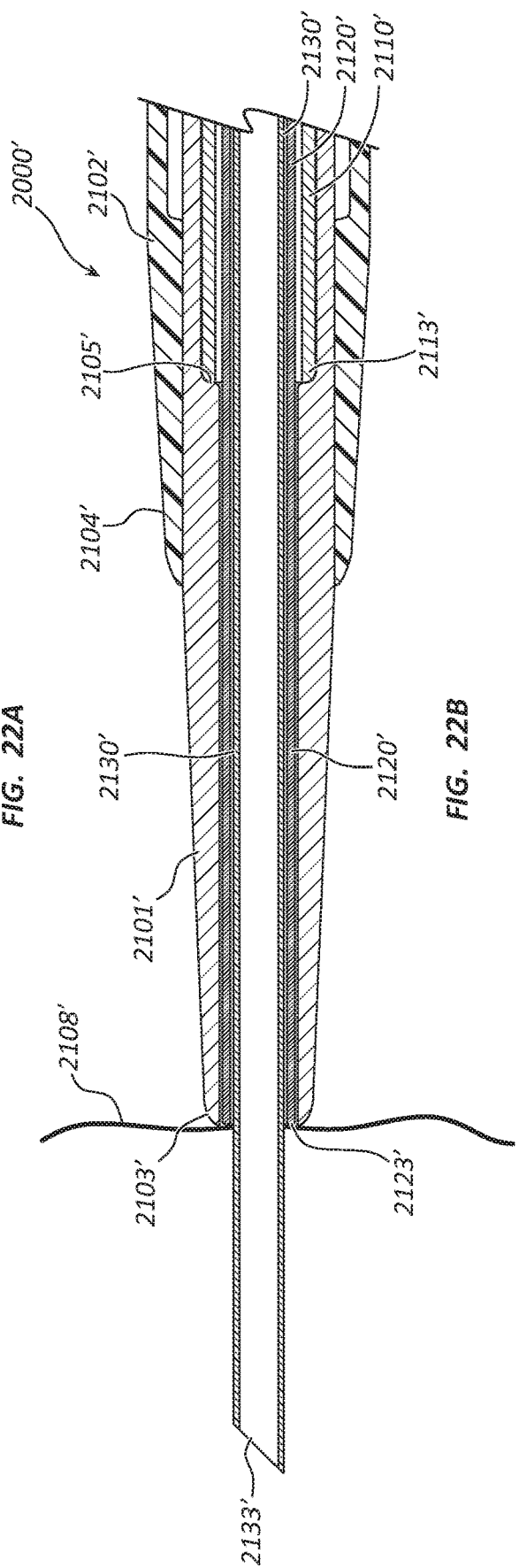
FIG. 22B is a longitudinal cross-sectional view of a distal portion of the telescoping needle assembly of FIG. 19 in a needle extending state.

FIG. 22A illustrates a configuration of the handle 2140' in the unlocked state, and FIG. 22B illustrates the configuration of a distal end portion of the telescoping needle assembly 2000 in a needle extending state. The button 2179' of the locking member 2177' may be displaced laterally by the clinician to the other end of the elongate opening 2142'. The downward projection 2184' is thereby displaced away from the outer cannula carriage 2158' such that the outer cannula carriage 2158' is not blocked from longitudinal movement in the proximal direction.

FIG. 22B shows the distal end 2133' of the needle 2130' may be displaced distally to penetrate an atrial septum 2108' when the clinician grips the handle 2140' with one hand and grips a proximal portion of the dilator 2101' and a sheath 2102' with the other hand. The upper housing 2141' (not shown), the lower housing 2148', the locking member 2177', and the needle 2130' may be displaced distally relative to the dilator 2101' and the sheath 2102' causing the outer cannula carriage 2158' and the middle cannula carriage 2166' to displace proximally relative to the handle 2140' in opposition to the force of the coil springs 2191'. The distal end 2133' of the needle 2130' may extend beyond the distal end 2123' of the middle cannula 2120' to penetrate the atrial septum 2108'. The outer cannula carriage 2158' and the middle cannula carriage 2166' may be configured to remain stationary relative to the dilator 2101' and the sheath 2102' because the distal end 2113' of the outer cannula 2110' abuts against the internal shoulder 2105' of the dilator 2101', the outer cannula 2110' may be fixedly coupled to the outer cannula carriage 2158', and the middle cannula 2120' may be fixedly coupled to the middle cannula carriage 2166'. The handle 2140' may be displaced distally until the wing 2176' of the middle cannula carriage 2166' contacts the proximal stop 2192'. The gap 2164' may remain between the middle cannula carriage 2166' and the distal portion 2161' of the outer cannula carriage 2158'.

FIGS. 23A and 23B show the telescoping needle assembly 2000' in a middle cannula extending state. In this state, the distal end 2123' of the middle cannula 2120' is extending beyond the distal end 2103' of the dilator 2101' by continued distal displacement of the handle 2140'. The proximal stop 2192' may be configured to engage with the wing 2176' and displace the middle cannula carriage 2166' distally while the outer cannula carriage 2158' remains stationary. Distal displacement of the middle cannula carriage 2166' may result in closing of the gap 2164' and distal displacement of the middle cannula 2120' such that the distal end 2123' may extend at least partially through the atrial septum 2108'.

FIGS. 24-28B depict an embodiment of a telescoping needle assembly 2000" that resembles the telescoping needle assembly 2000' described above in certain respects. Accordingly, like features are designated with like reference numerals, with the "''" (double prime) symbol added as a suffix. For example, the embodiment depicted in FIG. 24 includes a handle 2140" that may, in some respects, resemble the handle 2140' of FIG. 19. Relevant disclosure set forth above regarding similarly identified features thus may not be repeated hereafter. Moreover, specific features of the telescoping needle assembly 2000' and related components shown in FIGS. 19-23B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the telescoping needle assembly 2000" and related components depicted in FIGS. 24-28B. Any suitable combination of the features, and variations of the same, described with respect to the telescoping needle assembly 2000' and related components illustrated in FIGS. 19-23B can be employed with the telescoping needle assembly 2000" and related components of FIGS. 24-28B, and vice versa.

Figure 24:
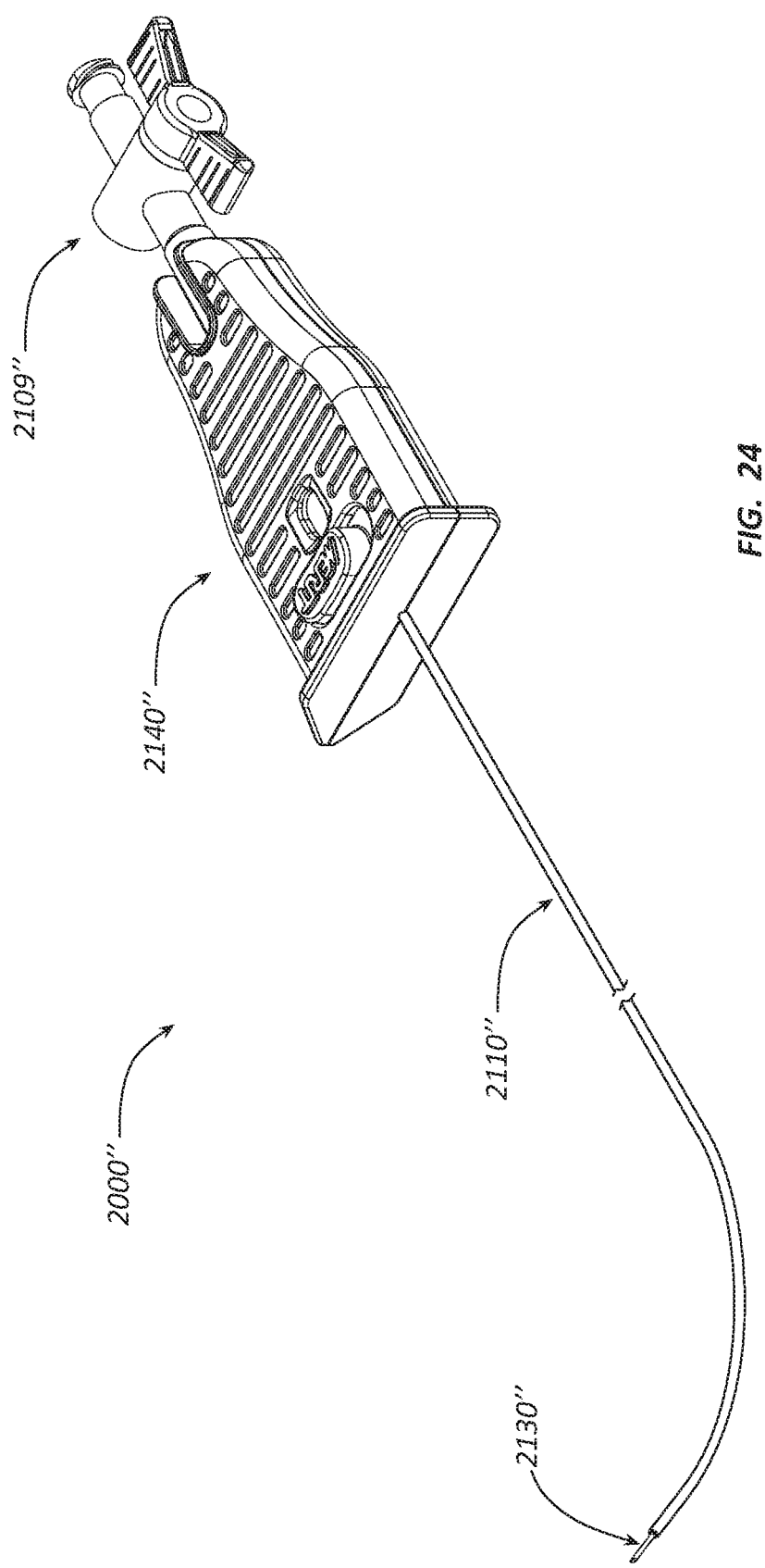
FIG. 24 is a perspective view of a telescoping needle assembly according to a fifth embodiment.

FIGS. 24-28B depict an embodiment of the telescoping needle assembly 2000. As shown in the embodiment of FIG. 24, the telescoping needle assembly 2000" includes an outer cannula 2110", a needle 2130", and a handle 2140".

Figure 25B:
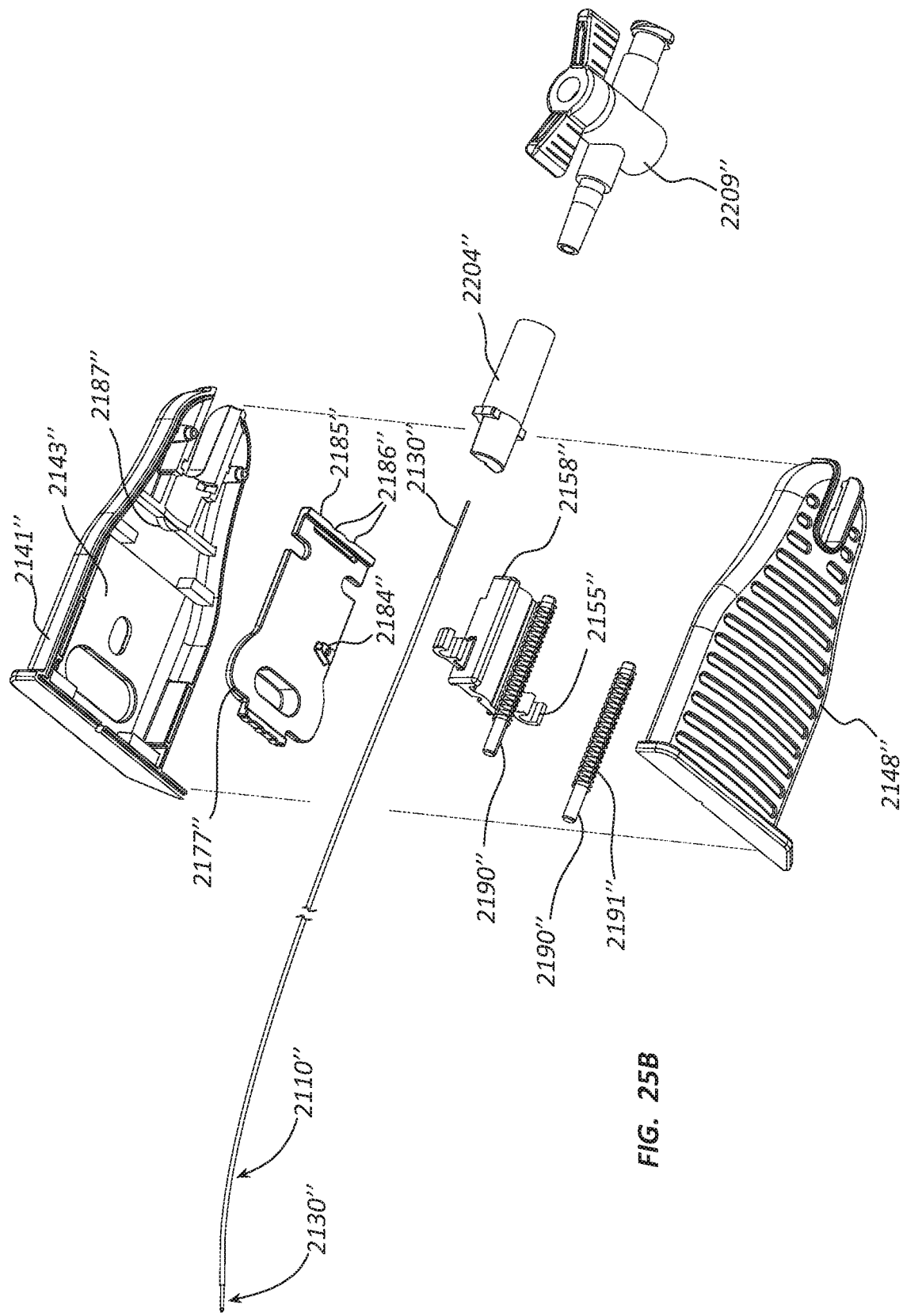
FIG. 25B is an exploded perspective bottom view of the handle of the telescoping needle assembly of FIG. 24.

FIGS. 25A and 25B illustrate exploded perspective views of the handle 2140. As illustrated in the embodiment of FIGS. 25A and 25B, the handle 2140" includes an upper housing 2141", an outer cannula carriage 2158", and a locking member 2177".

The upper housing 2141" may be configured to couple with a lower housing 2148". The upper housing 2141" includes an elongate opening 2142" and a recess 2143" disposed on a bottom surface. The elongate opening 2142" may be oriented transverse to a longitudinal axis of the upper housing 2141" and may be configured to slidingly receive a button 2179" of the locking member 2177". The recess 2143" may be elongated and configured to slidingly receive a portion of the locking member 2177".

With continued reference to the embodiment illustrated in FIGS. 20A and 20B, the lower housing 2148" may be configured to couple with the upper housing 2141". The lower housing 2148" includes an elongate cavity 2149". The cavity 2149" is oriented with a longitudinal axis of the lower housing 2148" and is configured to slidingly receive the outer cannula carriage 2158". The cavity 2149" defines a distal stop 2152" and a proximal stop 2192".

A pair of rods 2190" may be disposed within lateral pockets 2146" of the lower housing 2148". The lateral pockets 2146" may comprise end portions configured to engage the ends of the rods 2190" so that the rods 2190" are constrained in a parallel orientation. The coil springs 2191" may be disposed on the rods 2190" as further described below.

The outer cannula carriage 2158" includes a distal portion 2161" and a proximal portion 2160". The outer cannula carriage 2158" may be configured to be slidingly disposed within the cavity 2149". The proximal end 2114" may be fixedly coupled to the outer cannula carriage 2158" using any suitable technique, such as gluing, welding, insert molding, etc.

The outer cannula carriage 2158" may comprise lateral extensions 2155" configured to slidingly engage the rods 2190". As such, the rods 2190" may constrain lateral displacement of the outer cannula carriage 2158" while allowing longitudinal displacement. The coil springs 2191" may be disposed between the lateral extensions 2155" and proximal end portions of the lateral pockets 2146' such that the coil springs 2191" exert a distal force on the lateral extensions 2155" urging the outer cannula carriage 2158" in the distal direction.

A proximal end 2134" of the needle 2130" may be coupled to a needle hub 2204". The needle hub 2204" may be disposed at least partially within the handle 2140" and include a connector portion for coupling to a medical device, such as a stopcock 2109", syringe, medical connector, etc.

The locking member 2177" includes a body 2178", the upward projection or button 2179", and the downward projection 2184". The body 2178" may be configured to be slidingly received within the recess 2143" of the upper housing 2141". The button 2179" extends vertically upward from the body 2178" and may be configured to be received within the elongate opening 2142" of the upper housing 2141". The button 2179" may be configured to be engaged by a finger of a clinician to displace the locking member 2177" transversely from a locked state (one end of the elongate opening 2142") to an unlocked state (the other end of the elongate opening 2142"). The downward projection 2184" extends from a bottom surface of the body 2178" and is configured to engage the outer cannula carriage 2158" and thereby prevent longitudinal displacement of the outer cannula carriage 2158" when the button 2179" is in the locked state.

Displacement of the button 2179" between the locked state and the unlocked state may be partially inhibited by detents as described below. The locking member 2177" may comprise a proximal wall 2185" extending downward from the bottom surface of the body 2178". A gap between a central portion of the proximal wall 2185" and the body 2178" may provide for flexibility of the central portion. The proximal wall 2185" may comprise a pair of recesses 2186" disposed along a proximal surface of the proximal wall 2185". The recesses 2186" may be configured to engage a corresponding protrusion 2187" disposed on the bottom surface of the upper housing 2141". When the locking member 2177" is in the locked state, the protrusion 2187" may be disposed within one recess 2186" and when the locking member 2177" is in the unlocked state, the protrusion 2187" may be disposed within the other recess 2186". During transition from the locked state to the unlocked state, the central portion of the proximal wall 2185" may flex distally so as to allow the protrusion 2187" to be displaced from the one recess 2186" to the other recess 2186".

In use, FIG. 26A illustrates a configuration of the handle 2140" in the locked state and FIG. 26B illustrates the configuration of a distal end portion of the telescoping needle assembly 2000" in a loaded state. FIG. 26B shows the telescoping needle assembly 2000" loaded into a dilator 2101" until a distal end 2113" of the outer cannula 2110" abuts an internal shoulder 2105" adjacent the distal end 2103" of the dilator 2101". When abutting the internal shoulder 2105", the telescoping needle assembly 2000" may be restricted from further advancement. A diameter of the lumen of the dilator 2101" distal to the internal shoulder 2105" is smaller than an outer diameter of the outer cannula 2110". A distal end 2133" of the needle 2130" is disposed proximal of the distal end 2113" of the outer cannula 2110". As shown in FIG. 26A, the locking member 2177" of the handle 2140" is in a locked state such that the downward projection 2184" abuts against the outer cannula carriage 2158" to prevent longitudinal displacement of the outer cannula carriage 2158" in the proximal direction.

FIG. 27A illustrates a configuration of the handle 2140" in the unlocked state, and FIG. 27B illustrates the configuration of a distal end portion of the telescoping needle assembly 2000 in a needle extending state. The button 2179" of the locking member 2177" is displaced laterally away from the locked state to the unlocked state. Accordingly, the downward projection 2184" is displaced away from the outer cannula carriage 2158" such that the outer cannula carriage 2158" is not blocked from longitudinal movement in the proximal direction.

FIG. 27B shows the distal end 2133" of the needle 2130" displaced distally to extend beyond the distal end 2113" of the outer cannula 2110" and further to extend beyond the distal end 2103 of the dilator 2101. The upper housing 2141", the lower housing 2148", the locking member 2177", and the needle 2130" may be displaced distally relative to the dilator 2101" and the sheath 2102" causing the outer cannula carriage 2158" to displace proximally relative to the handle 2140" in opposition to the force applied by the coil springs 2191" and causing the distal end 2133" of the needle 2130" to extend. The outer cannula carriage 2158" may be configured to remain stationary relative to the dilator 2101" and the sheath 2102" because the distal end 2113" of the outer cannula 2110" abuts against the internal shoulder 2105" of the dilator 2101" and the outer cannula 2110" is fixedly coupled to the outer cannula carriage 2158". The handle 2140" may be displaced distally until the outer cannula carriage 2158" contacts the proximal stop 2192".

Figure 28:
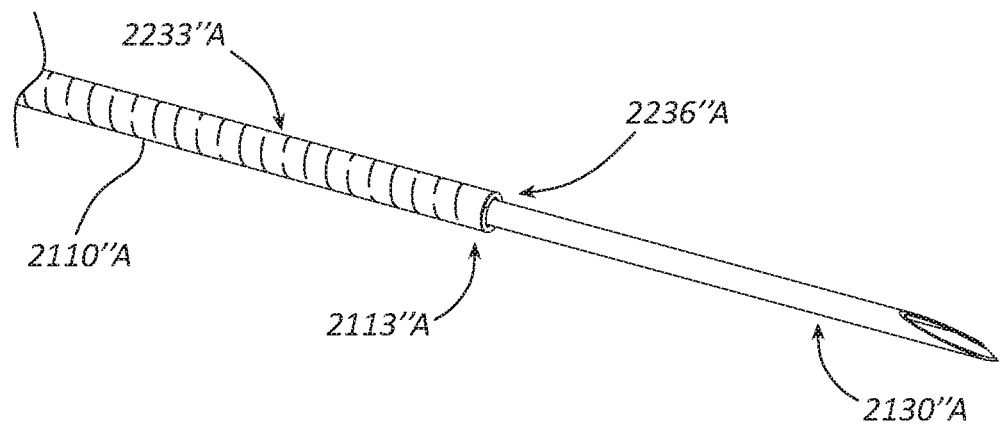
FIG. 28 is a perspective view of a first alternative embodiment of the outer cannula and the needle of FIG. 24."
Figure 29:
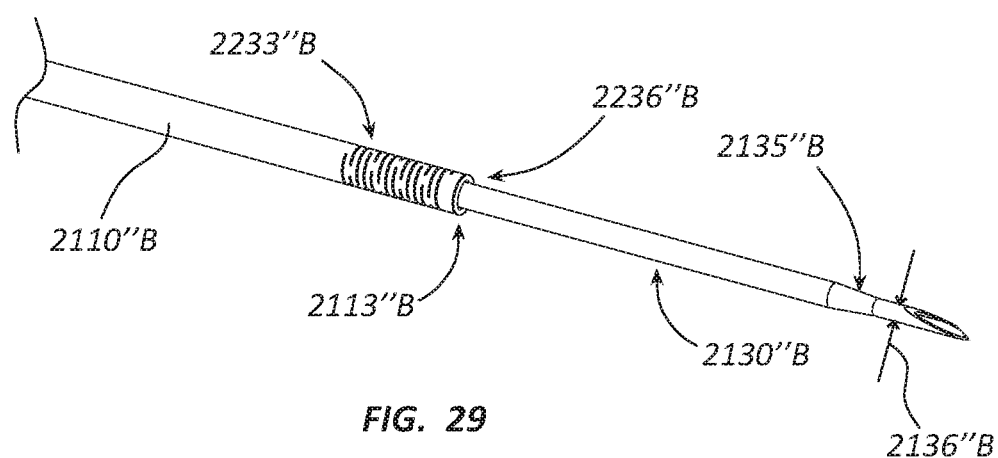
FIG. 29 is a perspective view of a second alternative embodiment of the outer cannula and the needle of FIG. 24."
Figure 30:
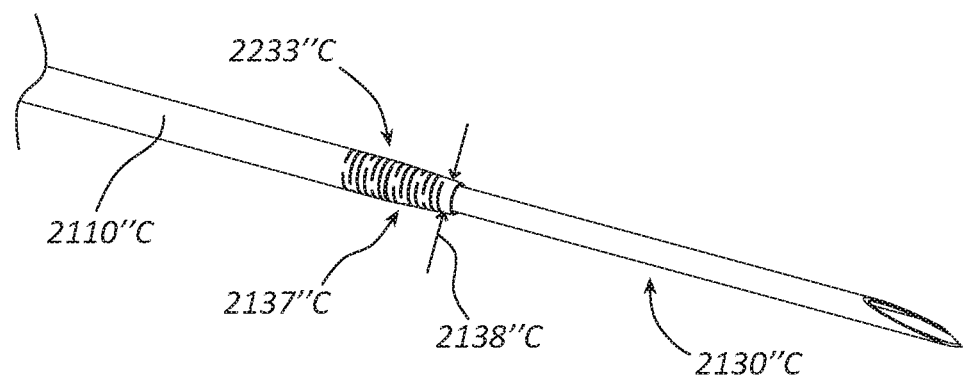
FIG. 30 is a perspective view of a third alternative embodiment of the outer cannula and the needle of FIG. 24."

FIGS. 28-31 depict different embodiments of the outer cannula 2110" and the needle 2130". Each of the different embodiments of the cannula 2110" and the needle 2130" as depicted in FIGS. 28-31 may comprise features that may resemble in certain respects features of the other embodiments. Accordingly, like features are designated with like reference numerals, with different suffix alpha characters. For example, the outer cannula 2110"A depicted in FIG. 28 may, in some respects, resemble the outer cannulae 2110"B and 2110"C as depicted in FIGS. 29 and 30, respectively. Relevant disclosure set forth regarding similarly identified features thus may not be repeated thereafter. Moreover, specific features of the outer cannulae 2110"A-2110"C and the needles 2130"A-2130"C shown in any one of FIGS. 28-31 may not be shown or identified by a reference numeral in the other figures or in the written description. However, such features may clearly be the same, or substantially the same. Accordingly, the relevant descriptions of such features apply equally to the features of the other outer cannulae and needles depicted in each of the FIGS. 28-31. Any suitable combination of the features, and variations of the same, described with respect to the outer cannulae 2110"A-2110"C and the needles 2130"A-2130"C shown in FIGS. 28-31 can be employed with the outer cannula 2110" and the needle 2130" of the telescoping needle assembly 2000" and related components of FIGS. 24-27B. Furthermore, the outer cannula 2110" and the needle 2130" as recited herein may have reference to any one of the outer cannulae 2110"A-2110"C and the needles 2130"A-2130"C, respectively.

FIG. 28 shows an outer cannula 2110"A and needle 2130"A. The needle 2130"A may have an outside diameter that may closely match an inside diameter of the outer cannula 2110"A such that the needle 2130"A is slideably displaceable within the outer cannula 2110"A. The outer cannula 2110"A may comprise a weld 2236"A at the distal end 2113"A that may form an inside rim of reduced diameter that may reduce clearance between an inside diameter of the outer cannula 2110"A and an outside diameter of the needle 2130"A. The outer cannula 2110"A may further comprise a spiral cut 2233"A. In some embodiments the spiral cut 2233"A may extend substantially along the entire length of the outer cannula 2110"A. In other embodiments, the spiral cut 2233"A may extend along a partial length of the outer cannula 2110"A. In some embodiments, the spiral cut 2233"A may be disposed adjacent the distal end 2113"A.

FIG. 29 shows an outer cannula 2110"B and needle 2130"B. The needle 2130"B may have an outside diameter that may closely match an inside diameter of the outer cannula 2110"B such that the needle 2130"B is slideably displaceable within the outer cannula 2110"B. The outer cannula 2110"B may comprise a weld 2236"B that may form an inside rim of reduced diameter that may reduce clearance between an inside diameter of the outer cannula 2110"B and an outside diameter of the needle 2130"B. The outer cannula 2110"B may further comprise a spiral cut 2233"A disposed adjacent the distal end 2113"B. The needle 2130"B may comprise a taper 2135"B establishing a reduced diameter 2136"B of the needle 2130"B at distal end 2133"B.

FIG. 30 shows an outer cannula 2110"C and needle 2130"C. The needle 2130"C may have an outside diameter that is less an inside diameter of the outer cannula 2110"C such that the needle 2130"C is displaceable within the outer cannula 2110"C. The outer cannula 2110"C may comprise a taper 2137"C establishing a reduced diameter 2138"C of the outer cannula 2110"C that may reduce clearance between an inside diameter of the outer cannula 2110"C adjacent the distal end 2113"C and an outside diameter of the needle 2130"C. The outer cannula 2110"C may further comprise a spiral cut 2233"A disposed adjacent the distal end 2113"C that may at least partially overlap the taper 2137"C.

FIGS. 31-35B depict an embodiment of a telescoping needle assembly 3000. In the illustrated embodiment of FIG. 31, the telescoping needle assembly 3000 includes an outer cannula or first elongate member 3110, a middle cannula or second elongate member 3120, an inner cannula or needle 3130, and a handle 3140.

Figure 32A:
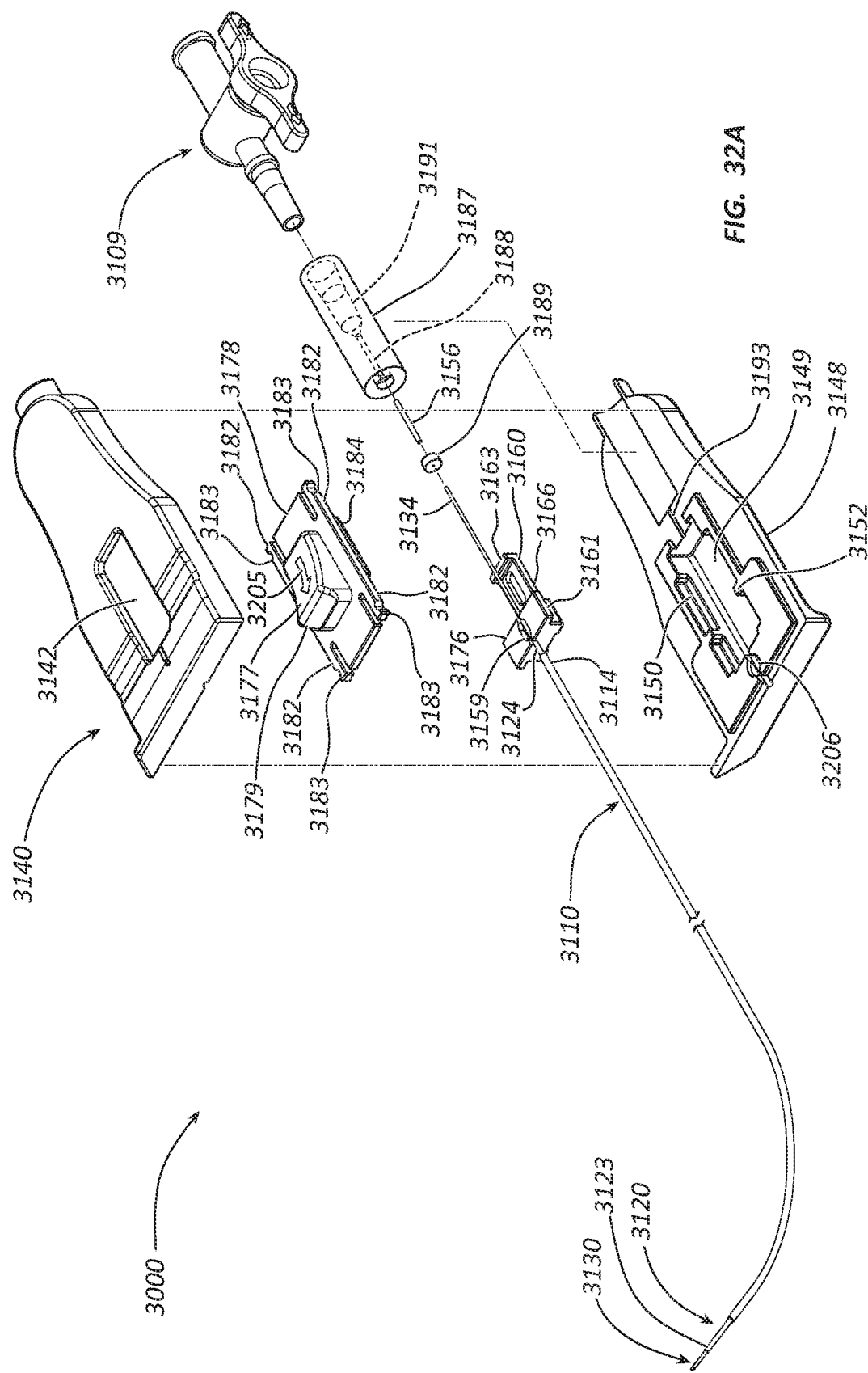
FIG. 32A is an exploded perspective top view of a handle of the telescoping needle assembly of FIG. 31.
Figure 32B:
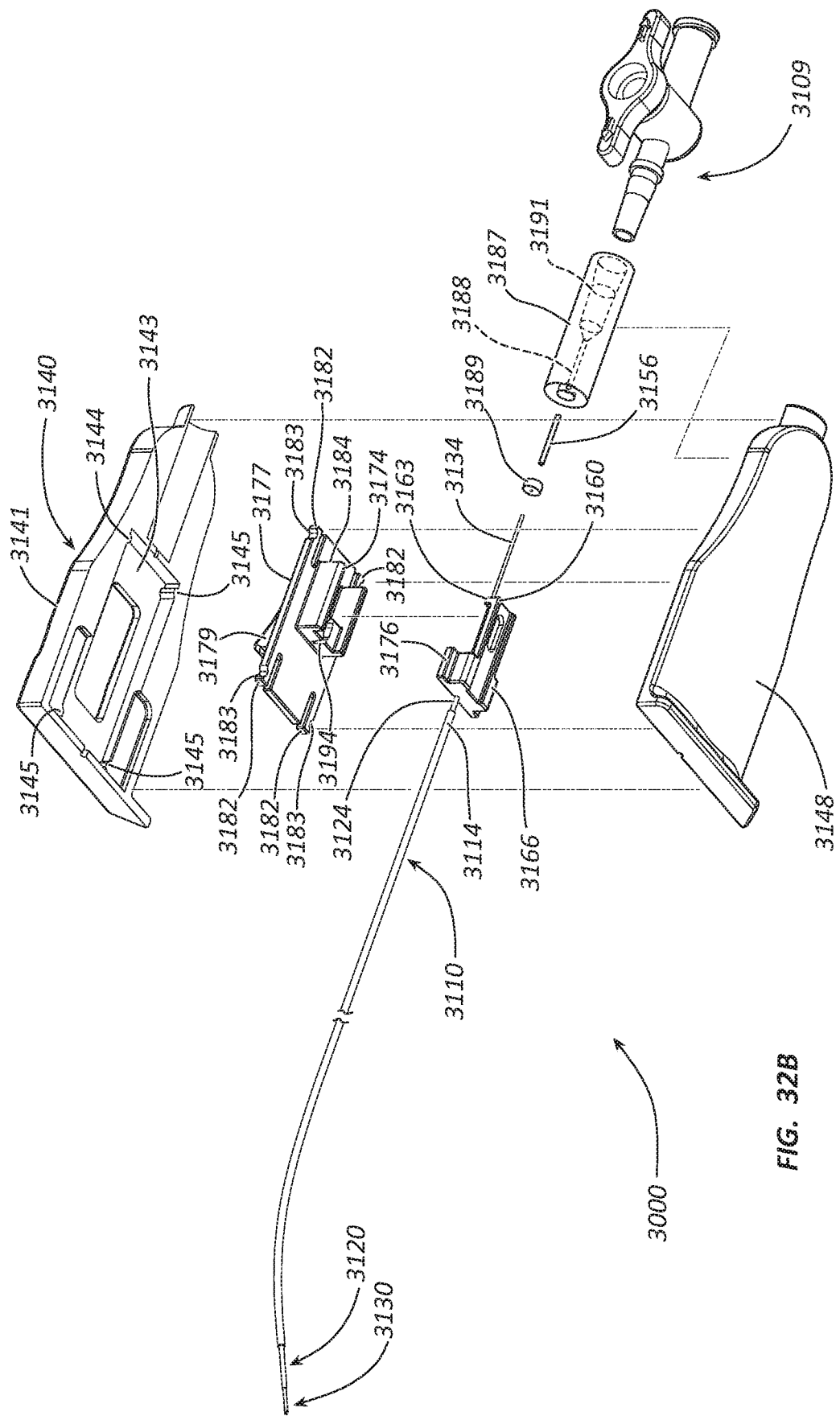
FIG. 32B is an exploded perspective bottom view of the handle of the telescoping needle assembly of FIG. 31.

FIGS. 32A and 32B illustrate an exploded perspective view of the handle 3140 of the telescoping needle assembly 3000. In the illustrated embodiment, the handle 3140 includes an upper housing 3141, a middle cannula carriage 3166, an insert 3187, and a locking member 3177.

As shown in FIGS. 32A and 32B, the upper housing 3141 may be configured to couple with a lower housing 3148. The upper housing 3141 includes an elongate opening 3142, a recess 3143 disposed on a bottom surface, and proximal detents 3144 and distal detents 3145 disposed within the recess 3143. The elongate opening 3142 is oriented with a longitudinal axis of the upper housing 3141 and may be configured to slidingly receive a button 3179 of the locking member 3177. The recess 3143 may be elongated and configured to slidingly receive a body 3178 of the locking member 3177. The proximal detents 3144 and the distal detents 3145 are disposed at proximal and distal portions of the recess 3143, respectively, and may be configured to couple with notches 3183 of the locking member 3177 as will be described below.

The lower housing 3148 may be configured to couple with the upper housing 3141. The lower housing 3148 includes an elongate cavity 3149. The cavity 3149 is oriented with a longitudinal axis of the lower housing 3148 and may be configured to slidingly receive the middle cannula carriage 3166. The cavity 3149 may be configured with a wide upper portion and a narrow lower portion. A pair of shelves 3150 may be disposed on lateral sides of the cavity 3149 and divide the upper portion from the lower portion. The shelves 3150 are divided longitudinally by inwardly extending stops 3152.

The upper housing 3141 and the lower housing 3148 include a distal channel 3206 that may be sized to receive a proximal end 3114 of the outer cannula 3110. The proximal end 3114 may be fixedly coupled to the upper housing 3141 and the lower housing 3148 within the channel 3206 using any suitable technique, such as gluing, welding, insert molding, etc.

The upper housing 3141 and the lower housing 3148 include a proximal channel 3193 extending through the proximal portions of the housings 3141, 3148. A distal portion of the channel 3193 opens into the cavity 3149 and may be sized to slidingly receive a proximal end 3134 of the needle 3130. A guide cannula 3156 may be disposed within the channel distal to a disk valve 3189 and configured to slidingly receive the proximal end 3134. A proximal portion of the channel 3193 may be sized to receive the insert 3187. The insert 3187 may include a distal cavity 3188 in fluid communication with the channel 3193 and configured to receive the disk valve 3189. The disk valve 3189 may be configured to slidingly receive and seal around the proximal end 3134 of the needle 3130. The insert 3187 may include a connector portion 3191 in fluid communication with the channel 3193. In some embodiments, the connector portion 3191 may be configured to couple to a medical device, such as a stopcock 3109, a syringe, an IV tubing connector, etc.

The middle cannula carriage 3166 includes a proximal portion 3160 and a distal portion 3161. The middle cannula carriage 3166 may be configured to be slidingly disposed within the cavity 3149 between the shelves 3150. The distal portion 3161 comprises a channel 3159 extending longitudinally through an upper surface. The channel 3159 may be sized to receive a proximal end 3124 of the middle cannula 3120. The middle cannula 3120 may be fixedly coupled to the middle cannula carriage 3166 within the channel 3159 using any suitable technique, such as gluing, welding, insert molding, etc. The distal portion 3161 may include lateral extensions or wings 3176 configured to slidingly couple with a distal portion of the shelves 3150. The distal portion 3161 includes a vertical stop 3163.

The locking member 3177 includes the body 3178, the upward projection or button 3179, and a downward projection 3184. The body 3178 may be planar and configured to be slidingly received within the recess 3143 of the upper housing 3141 and to slidingly couple with an upper surface of the lower housing 3148. The body 3178 includes cantilever arms 3182 extending proximally and distally from a central portion and disposed on lateral portions of the body 3178. Each cantilever arm 3182 includes a notch 3183 disposed adjacent a distal end. The notches 3183 may be configured to engage with the proximal detents 3144 or the distal detents 3145 of the upper housing 3141 such that the locking member 3177 may be locked or restricted from longitudinal displacement.

The button 3179 extends vertically upward from the body 3178 and may be configured to be displaceably received within the elongate opening 3142 of the upper housing 3141. The button 3179 may be configured to be engaged by a finger of a clinician to displace the locking member 3177 proximally and/or distally. The button 3179 may include any suitable shape to facilitate displacement of the locking member 3177 by the finger of the clinician. As shown in FIGS. 32A and 32B, the shape of the button 3179 is tapered from a distal portion to a proximal portion. In other embodiments, the button 3179 may be planar. The button 3179 may include an indicium 3205, such as an arrow, to indicate the direction the locking member 3177 should be displaced to extend the needle 3130 from a distal end 3123 of the middle cannula 3120.

The downward projection 3184 extends from a bottom surface of the body 3178 and may be configured to be slidingly received within the cavity 3149 of the lower housing 3148. The downward projection 3184 may include rails 3174 configured to straddle the distal portion 3160 of the middle cannula carriage 3166. The downward projection 3184 includes a channel or passage 3194 that may be sized to receive a portion of the needle 3130. The needle 3130 may be fixedly coupled to the channel 3194 using any suitable technique, such as gluing, welding, insert molding, etc. The downward projection 3184 may be configured to abut the vertical stop 3163 of the middle cannula carriage 3166 when the locking member 3177 is displaced distally.

Figures 33A, 33B:
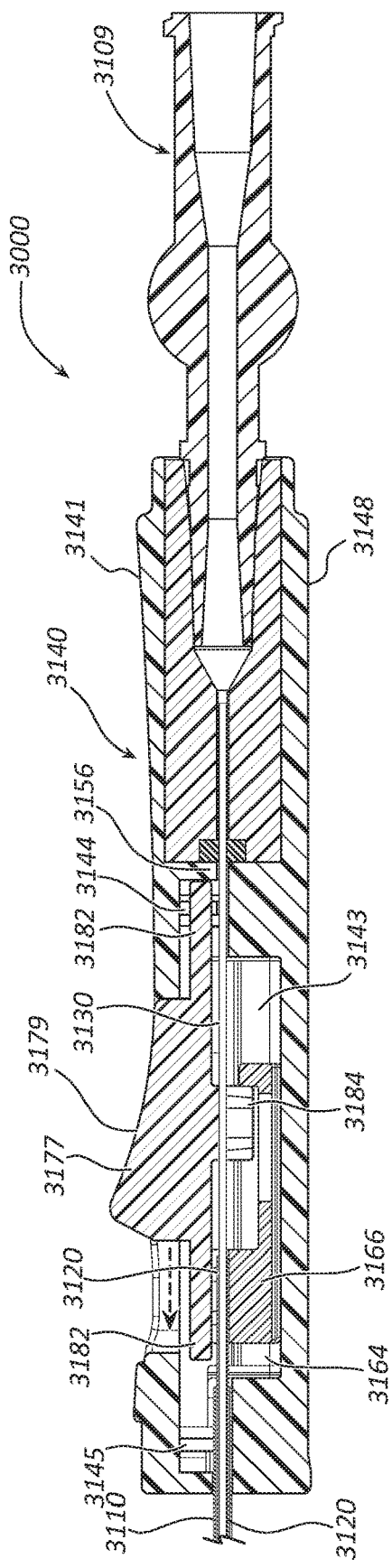
FIG. 33A is a longitudinal cross-sectional view of a proximal portion of the telescoping needle assembly of FIG. 31 in a locked state.
FIG. 33B is a longitudinal cross-sectional view of a distal portion of the telescoping needle assembly of FIG. 31 in a cannula loaded state.

In use, FIG. 33A illustrates the configuration of the handle 3140 in a locked state and FIG. 33B illustrates a distal end portion of the telescoping needle assembly 3000 in a loaded state. With reference to FIG. 33B, the telescoping needle assembly 3000 may be loaded into a dilator 3101 until a distal end 3113 of the outer cannula 3110 abuts an internal shoulder 3105 disposed adjacent a distal end 3103 of the dilator 3101. When abutting the internal shoulder 3105, the telescoping needle assembly 3000 may be restricted from further advancement. The distal end 3123 of the middle cannula 3120 and a distal end 3133 of the needle 3130 may extend beyond the distal end 3113 and may be positioned adjacent the distal end 3103 of the dilator 3101 but do not extend out of the dilator 3101.

Referring to FIG. 33A, the locking member 3177 of the handle 3140 is in a locked state for loading the telescoping needle assembly 3000 into the dilator 3101. The notches 3183 (not shown) of the proximally extending cantilever arms 3182 may be engaged with the proximal detents 3144 of the upper housing 3141. The button 3179 may be positioned proximally and the downward projection 3184 may be positioned adjacent a proximal portion of the recess 3143. The middle cannula carriage 3166 may be disposed away from a distal end of the recess 3143 such that the gap 3164 may be defined between the middle cannula carriage 3166 and the distal end of the recess 3143.

Figure 34A:
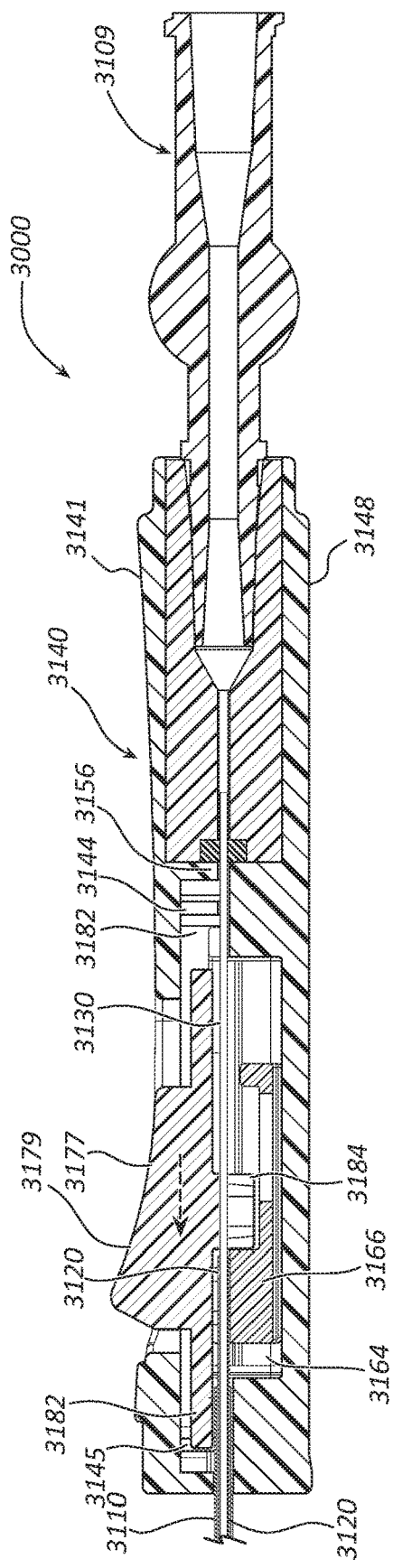
FIG. 34A is a longitudinal cross-sectional view of a proximal portion of the telescoping needle assembly of FIG. 31 in an unlocked state.
Figure 34B:
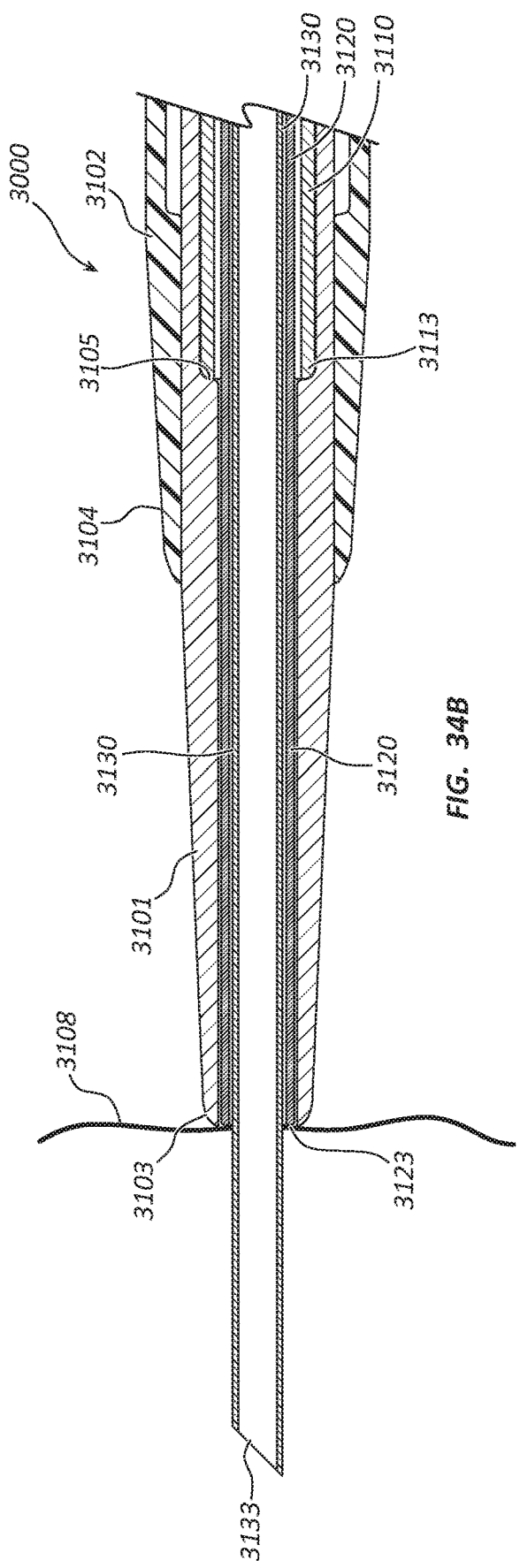
FIG. 34B is a longitudinal cross-sectional view of a distal portion of the telescoping needle assembly of FIG. 31 in a needle extending state.

FIGS. 34A and 34B illustrate the distal portion of the telescoping needle assembly 3000 in a needle extending state. FIG. 34A shows the locking member 3177 is displaced partially distally to an unlocked state. The button 3179 may be positioned distally within the elongate opening 3142. The notches 3183 of the proximally extending cantilever arms 3182 may be decoupled from the proximal detents 3144. The downward projection 3184 may be displaced distally and may abut the distal portion 3161 of the middle cannula carriage 3166.

FIG. 34B shows the needle 3130 may be displaced distally relative to the handle 3140, the outer cannula 3110, the middle cannula 3120, and the dilator 3101 by the locking member 3177 to penetrate an atrial septum 3108. The distal end 3133 of the needle 3130 may extend beyond the distal end 3123 of the middle cannula 3120 and penetrate the atrial septum 3108. The distal end 3133 may extend beyond the distal end 3123 a distance ranging from about 1 mm to 15 mm, from 5 mm to 15 mm, and from 5 mm to 10 mm. The middle cannula carriage 3166 and the middle cannula 3120 may be configured to remain stationary relative to the dilator 3101 and a sheath 3102 as partial distal displacement of the locking member 3177 is stopped upon contact of the downward projection 3184 with the distal portion 3161 of the middle cannula carriage 3166.

Figure 35A:
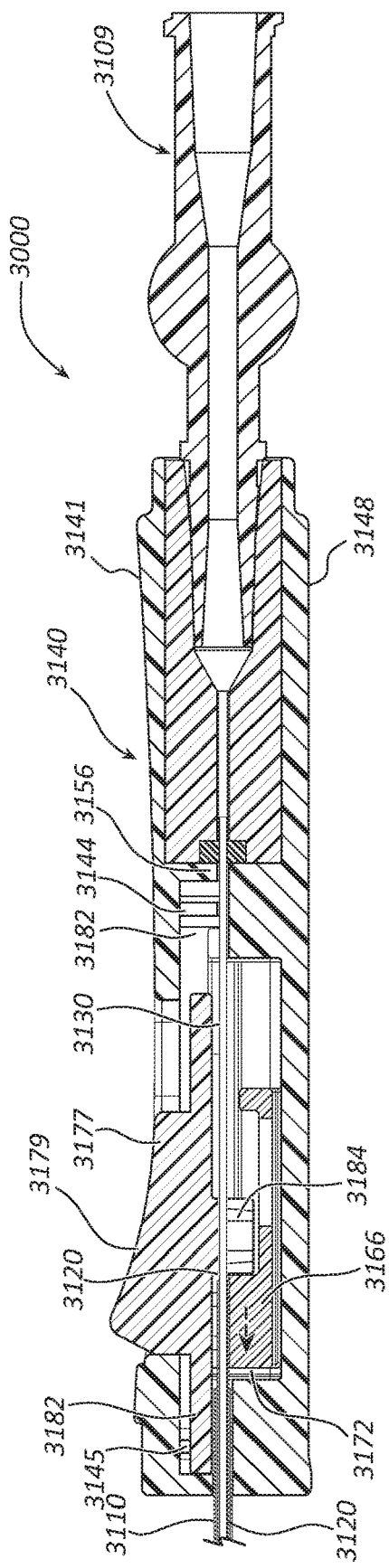
FIG. 35A is a longitudinal cross-sectional view of a proximal portion of the telescoping needle assembly of FIG. 31 in a middle cannula extending state.
Figure 35B:
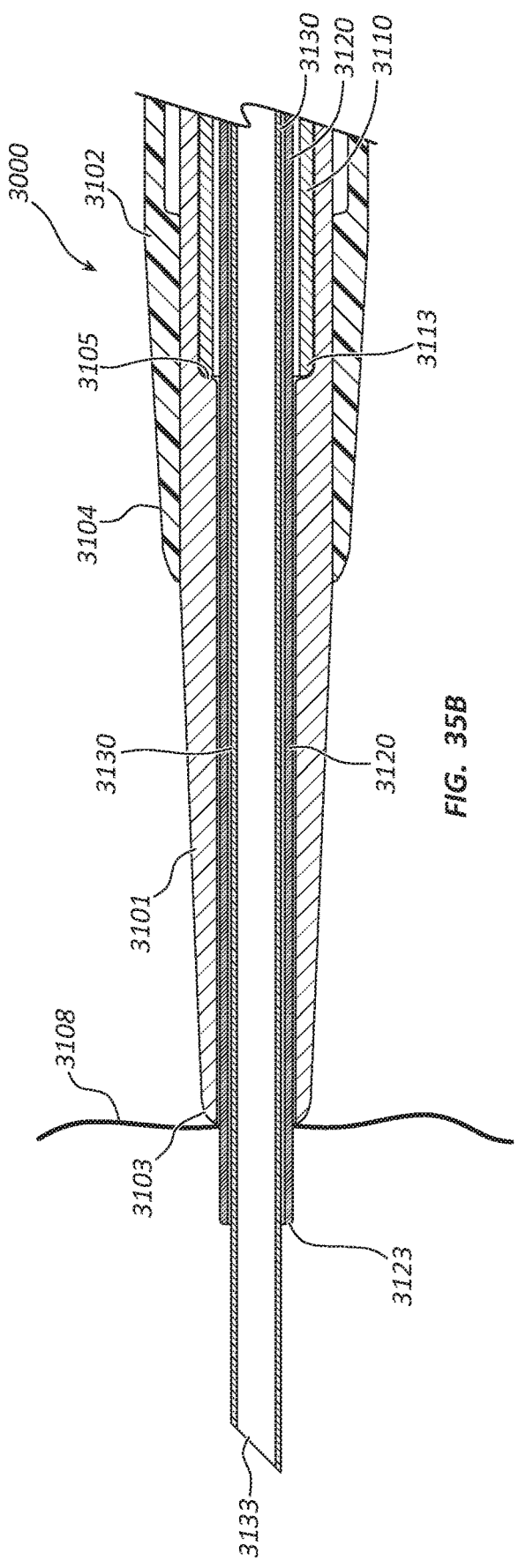
FIG. 35B is a longitudinal cross-sectional view of a distal portion of the telescoping needle assembly of FIG. 31 in a middle cannula extending state.
Figure 36:
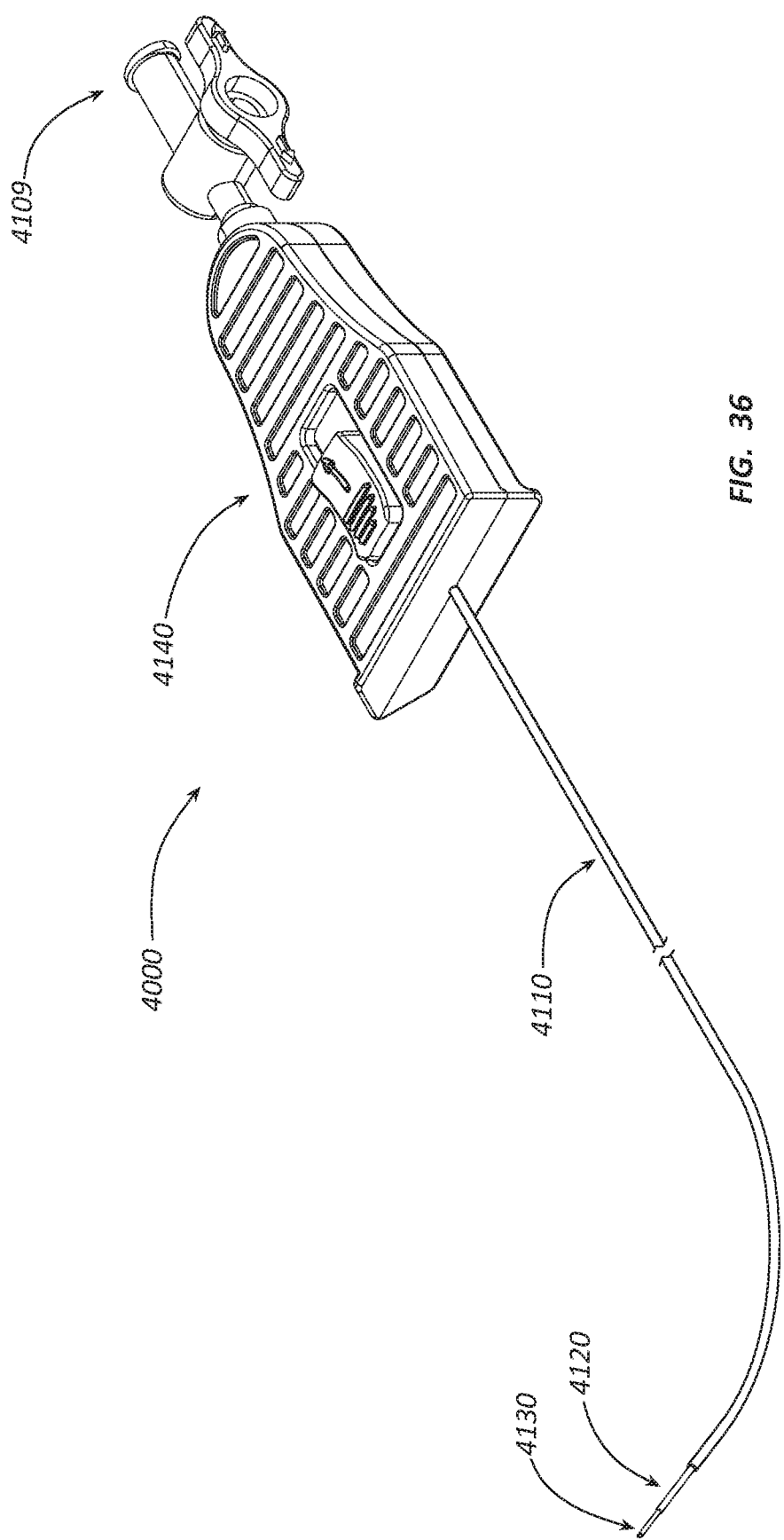
FIG. 36 is a perspective view of a telescoping needle assembly according to a seventh embodiment.

FIGS. 35A and 35B illustrate the distal portion of the telescoping needle assembly 3000 in a middle cannula extending state. FIG. 35A shows the locking member 3177 is displaced fully distally in the unlocked state and the button 3179 positioned distally within the elongate opening 3142. The notches 3183 of the distally extending cantilever arms 3182 may be coupled with the distal detents 3145 such that the locking member 3177 may be restricted from proximal displacement. The downward projection 3184 is displaced distally thereby distally displacing the middle cannula carriage 3166 such that the gap 3164 is closed and the wings 3176 abut a distal end of the shelves 3150. Distal displacement of the middle cannula carriage 3166 results in distal displacement of the middle cannula 3120 such that the distal end 3123 may extend at least partially through the atrial septum 3108. FIG. 35B shows the distal end 3123 of the middle cannula 3120 extending beyond the distal end 3103 of the dilator 3101.

FIGS. 36-40B depict an embodiment of a telescoping needle assembly 4000. In the illustrated embodiment, the telescoping needle assembly 4000 includes an outer cannula 4110, a middle cannula 4120, a needle 4130, and a handle 4140. In other embodiments, the telescoping needle assembly 4000 may only include a subset of these components. For instance, in some embodiments the assembly may not include the middle cannula 4120. In some embodiments, a medical device, such as a stopcock 4109, syringe, medical connector, etc., may be coupled to a proximal end of the handle 4140.

Figure 37A:
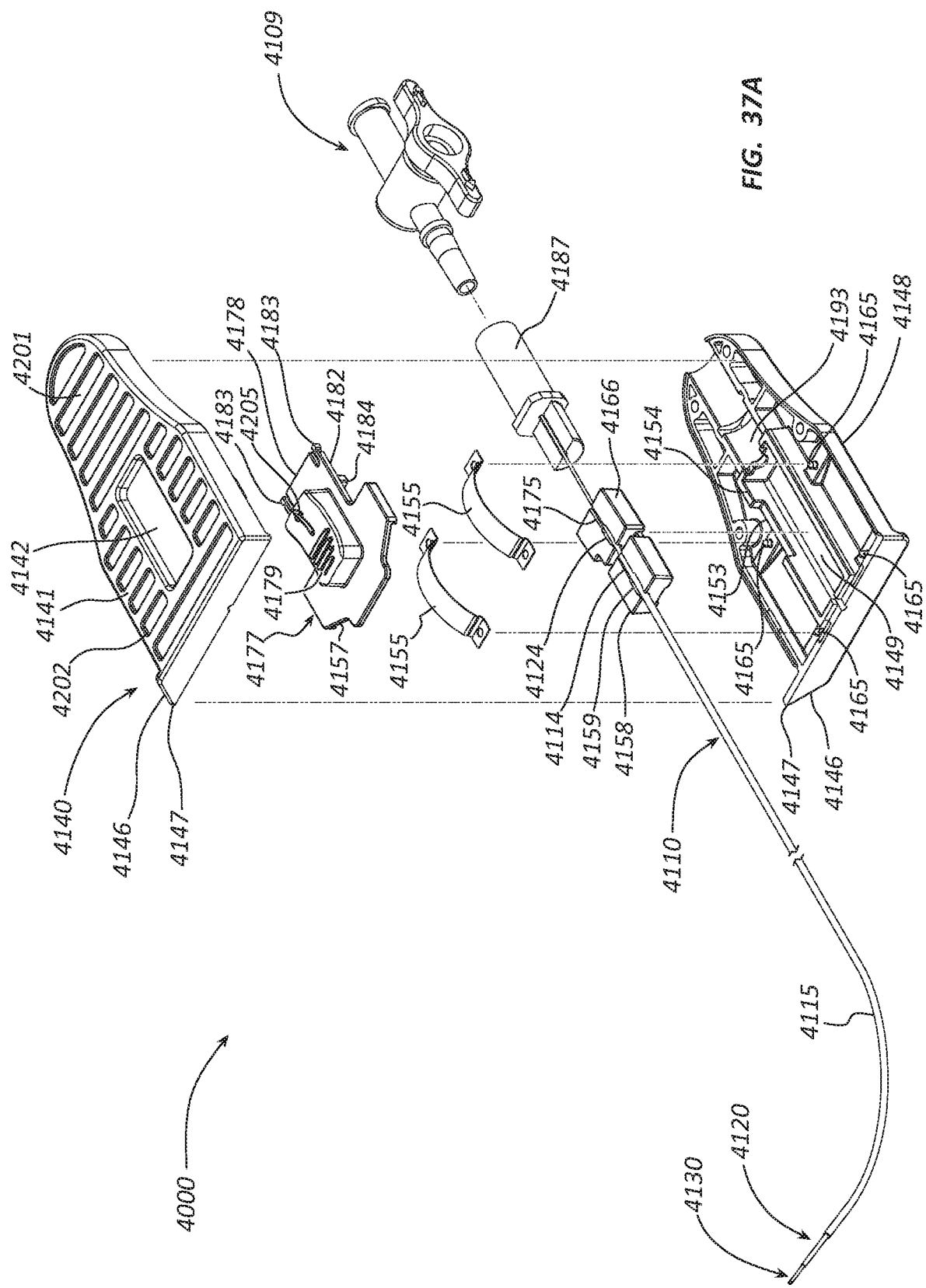
FIG. 37A is an exploded perspective top view of a handle of the telescoping needle assembly of FIG. 36.
Figure 37B:
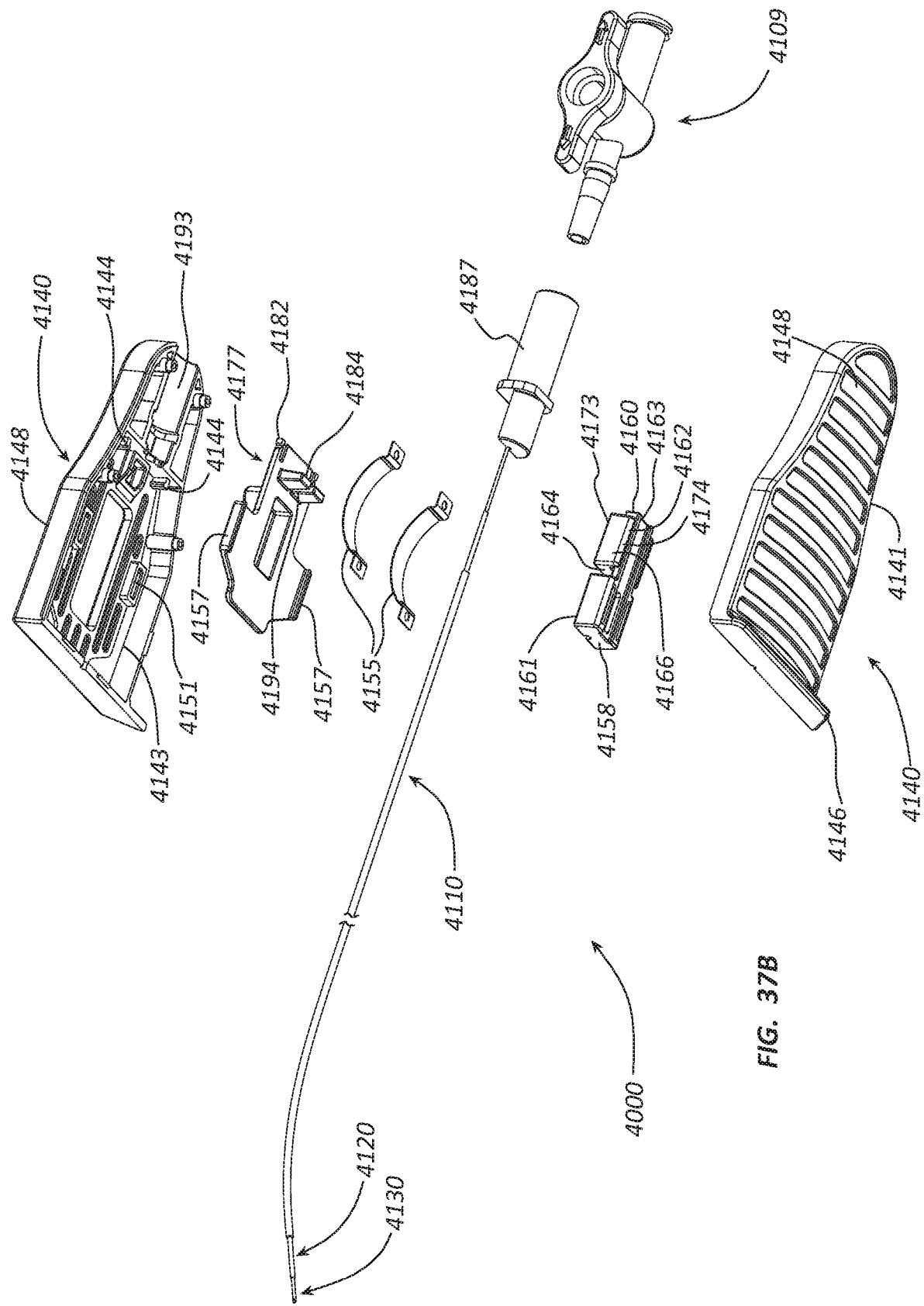
FIG. 37B is an exploded perspective bottom view of the handle of the telescoping needle assembly of FIG. 36.

FIGS. 37A and 37B illustrate exploded views of the handle 4140 of the telescoping needle assembly 4000. In the illustrated embodiment, the handle 4140 includes an upper housing 4141, a lower housing 4148, an outer cannula carriage 4158, a middle cannula carriage 4166, a needle hub 4240, and a locking member 4177.

As shown in FIGS. 37A and 37B, the upper housing 4141 is configured to couple with the lower housing 4148. The upper housing 4141 and the lower housing 4148 may be coupled using any suitable technique, such as gluing, welding, snap fit, etc. The upper housing 4141 may include a proximal portion 4201 that has a smaller width than a distal portion 4202 and features an outer surface to enhance gripability. In some embodiments, the gripping features may include transverse ribs, dimples, bumps, surface texturing, grip enhancing material, etc. The upper housing 4141 may include a first portion of an orientation indicator 4146 disposed adjacent the distal portion 4202 and extending orthogonally from a side of the upper housing 4141 that is aligned with the direction of curvature of an arcuate portion 4115 of the outer cannula 4110. The orientation indicator 4146 may be tapered to a point 4147. In other embodiments, the orientation indicator 4146 may include a radiused distal end, an arrow shape, or any other configuration suitable to indicate the orientation of the arcuate portion 4115 of the outer cannula 4110. The upper housing 4141 may be formed of any suitable rigid or semi-rigid thermoplastic material, such as polycarbonate, polypropylene, polyethylene, polyvinylchloride, etc.

In the illustrated embodiment, the upper housing 4141 includes an elongate opening 4142, a recess 4143 disposed in a bottom surface, proximal detents 4144, and stops 4151. The elongate opening 4142 is oriented with a longitudinal axis of the upper housing 4141 and is configured to slidingly receive a button 4179 of the locking member 4177. The recess 4143 is elongated and configured to slidingly receive a body 4178 of the locking member 4177. The proximal detents 4144 are disposed at a proximal portion of the recess 1143 and are configured to couple with cantilever arms 4182 of the locking member 4177 as will be described below. The stops 4151 extend downward into the recess 4143 and are disposed lateral to the opening 4142.

With continued reference to FIGS. 37A and 37B, in the illustrated embodiment, the lower housing 4148 is configured to couple with the upper housing 4141. The lower housing 4148 may be generally shaped to match the shape of the upper housing 4141 and may include features on an outer surface to facilitate gripping. In some embodiments, the gripping features may include transverse ribs, dimples, bumps, surface texturing, grip enhancing material, etc. The lower housing 4148 may include a second portion of the orientation indicator 4146 disposed adjacent the distal portion and extending orthogonally from a side of the lower housing 4148 that is aligned with the direction of curvature of the arcuate portion 4115 of the outer cannula 4110. As shown in the illustrated embodiment, the orientation indicator 4146 may be tapered to the point 4147. In other embodiments, the orientation indicator 4146 may include a radiused distal end, an arrow shape, or any other configuration suitable to indicate the orientation of the arcuate portion 4115 of the outer cannula 4110. The lower housing 1148 may be formed of any suitable rigid or semi-rigid thermoplastic material, such as polycarbonate, polypropylene, polyethylene, polyvinylchloride, etc.

In the illustrated embodiment, the lower housing 4148 includes an elongate cavity 4149. The cavity 4149 is oriented with a longitudinal axis of the lower housing 4148 and is configured to slidingly receive the outer cannula carriage 4158 and the middle cannula carriage 4166 between lateral walls 4154. A lateral wall 4154 of the cavity 4149 includes a notch 4153 configured to receive a portion of the locking member 4177 as will be described below.

The outer cannula carriage 4158 of the illustrated embodiment includes a distal portion 4161 and a proximal portion 4160. The outer cannula carriage 1158 may be configured to be slidingly disposed within the cavity 4149 between the lateral walls 4154. The distal portion 4161 comprises a slot 4159 extending longitudinally through an upper surface. The slot 4159 is sized to receive a proximal end 4114 of the outer cannula 4110. The outer cannula 4110 may be fixedly coupled to the outer cannula carriage 4158 using any suitable technique, such as gluing, welding, insert molding, etc. The proximal portion 4160 may include a vertical stop 4163. A recess 4162 may be disposed between the distal portion 4161 and the vertical stop 4163. The recess 4162 is configured to slidingly receive the middle cannula carriage 4166. The outer cannula carriage 4158 may be formed of any suitable rigid or semi-rigid thermoplastic material, such as polycarbonate, polypropylene, polyethylene, polyvinylchloride, etc.

The middle cannula carriage 4166 includes a body 4173 in the depicted embodiment. The middle cannula carriage 4166 may be configured to be slidingly disposed within the cavity 4149 and within the recess 4162 of the outer cannula carriage 4158 such that the middle cannula carriage 4166 is disposed between the distal portion 4161 and the vertical stop 4163. A gap 4164 is defined between the middle cannula carriage 4166 and the distal portion 4161. The body 4173 may comprise a slot 4175 extending longitudinally through an upper surface. The slot 4175 is sized to receive a proximal end 4124 of the middle cannula 4120. The middle cannula 4120 may be fixedly coupled to the middle cannula carriage 1166 using any suitable technique, such as gluing, welding, insert molding, etc. The body 4173 includes rails 4174 extending from a lower surface. The rails 4174 are configured to straddle a portion of the distal portion 4161 of the outer cannula carriage 4158 and to slidingly couple with a bottom surface of the cavity 4149. An upper portion of the body 4173 extends laterally and is configured to be slidingly received within the notch 4153 of the lateral wall 4154 of the cavity 4149.

The locking member 4177 includes the body 4178, the upward projection or button 4179, laterally extending wings 4157, and a downward projection 4184. The body 4178 is configured to be slidingly received within the recess 4143 of the upper housing 4141. The body 4178 also includes the cantilever arms 4182 extending proximally from a central portion and disposed on lateral portions of the body 4178. Each cantilever arm 4182 includes a notch 4183 disposed adjacent a distal end of the cantilever arm 4182. The notches 4183 are configured to engage with the proximal detents 4144 of the upper housing 4141 such that the locking member 4177 is restricted from longitudinal distal displacement.

The button 4179 extends vertically upward from the body 4178 and is configured to be received within the elongate opening 4142 of the upper housing 4141. The button 4179 is configured to be engaged by a finger of a clinician to displace the locking member 4177 proximally or distally. The button 4179 may include features to facilitate displacement of the locking member 4177. The features may include transverse ribs, bumps, dimples, textured surface, slip resistant material, etc. The button 4179 may include an indicium 4205, such as an arrow shape, to indicate the direction the locking member 4177 may be displaced to unlock the handle 4140.

The downward projection 4184 extends from a bottom surface of the body 4178 and is configured to be received within the cavity 4149 of the lower housing 1148. The downward projection 4184 includes a slot or passage 4194 sized to slidingly receive the needle 4130.

In the illustrated embodiment, the upper housing 4141 and the lower housing 4148 include a channel 4193 extending through the proximal portion 4201 of the housings 4141, 4148. A distal portion of the channel 4193 opens into the cavity 4149 and is sized to receive the needle hub 4240. The needle hub 4240 may comprise a bore extending longitudinally through the insert 4187. A proximal end 4134 of the needle 4130 may be fixedly coupled within a distal portion of the bore using any suitable technique, such as gluing, welding, insert molding, etc. A proximal portion of the bore may be configured to couple to a medical device, such as the stopcock 4109, syringe, medical connector, etc.

As shown in the illustrated figures, a pair of leaf springs 4155 may be disposed lateral to the cavity 4149. The leaf springs 4155 may be coupled to the lower housing 4148 using the studs 4165 or any other suitable technique, such as welding, gluing, over molding, etc. In certain embodiments, the leaf springs 4155 may slidingly engage a bottom surface of the wings 4157. The leaf springs 4155 may be formed from any suitable resilient material, such as steel, aluminum, thermal plastics, etc. The leaf springs 4155 are bowed upward such that they exert an upward force to the bottom surface of the wings 4157 of the locking member 4177. In other embodiments, the leaf springs 4155 may be configured as any suitable type of resilient member, such as a compression spring, an elastomeric block, etc.

In use, FIG. 38A illustrates a configuration of the handle 4140 in a locked state and FIG. 38B illustrates a distal end portion of the telescoping needle assembly 4000 in a loaded state. Referring to FIG. 38B, the dilator 4101 may be disposed within a lumen of a sheath 4102 such that a distal end 4103 of the dilator 4101 extends beyond a distal end 4104 of the sheath 4102. The dilator 4101 and the sheath 4102 may be inserted from a peripheral site, such as the groin, into the central vasculature or heart of the patient and positioned within the central vasculature or heart such that the distal end 4103 of the dilator 4101 is positioned against a vessel wall, membrane, or septum, such as an atrial septum 4108. The telescoping needle assembly 4000 is oriented such that the orientation indicator 4146 of the handle 4140 is directed toward a curvature of the dilator 4101 resulting in the curvature of the arcuate portion 4115 of the outer cannula 4110 aligning with the curvature of the dilator 4101 as described previously.

With continued reference to FIG. 38B, the telescoping needle assembly 4000 may be loaded into the dilator 4101 until the distal end 4113 of the outer cannula 4110 abuts an internal shoulder 4105 adjacent the distal end 4103 of the dilator 4101. When abutting against the internal shoulder 4105, the telescoping needle assembly 4000 may be restricted from further advancement. In the illustrated embodiment, the diameter of the lumen of the dilator 4101 distal to the internal shoulder 4105 is smaller than an outer diameter of the outer cannula 4110. A distal end 4123 of the middle cannula 4120 and a distal end 4133 of the needle 4130 extend beyond the distal end 4113 and are positioned adjacent the distal end 4103 of the dilator 4101 but do not extend out of the dilator 4101.

FIG. 38A shows the locking member 4177 of the handle 4140 in a locked state such that the leaf springs 4155 apply an upward force to the bottom surface of the wings 4157 of the locking member 4177. The upward force directs the body 4178 of the locking member 4177 into the recess 4143 of the upper housing 4141. A proximal edge of the wings 4157 is engaged with a distal face of the stops 4151 such that proximal displacement of the locking member 4177 is restricted. In the locked state the button 4179 is positioned distally and the downward projection 4184 abuts against the vertical stop 4163 such that the outer cannula carriage 4158 and the middle cannula carriage 4166 are prevented from longitudinal movement.

FIGS. 39A and 39B illustrate the telescoping needle assembly 4000 in an unlocked state and a needle extending state. FIG. 39A shows the locking member 4177 is in the unlocked state. To transition to the unlocked state, the button 4179 is depressed downwardly and displaced proximally. The leaf springs 4155 are flattened or nearly flattened. The proximal faces of the wings 4157 of the locking member 4177 are disengaged downwardly from the distal face of the stops 4151 such that the wings 4157 may be displaced proximally below the stops 4151. A top surface of the wings 4157 may be slidingly coupled to a bottom surface of the stops 4151. In some embodiments the proximally extending cantilever arms 4182 may be coupled to the proximal detents 4144 such that the locking member 4177 is retained in the unlocked state. The downward projection 4184 is displaced proximally such that the outer cannula carriage 4158 and the middle cannula carriage 4166 are not restricted from longitudinal movement.

To extend the needle 4130, the clinician may grip the handle 4140 with one hand and grip a proximal portion of the dilator 4101 and the sheath 4102 with the other hand. The handle 4140 may be displaced distally by the clinician. The handle 4140, the locking member 4177, and the needle 4130 may be displaced distally relative to the dilator 4101 and the sheath 4102 to the needle extending state. The distal end 4133 of the needle 4130 is telescoped or extended beyond the distal end 4123 of the middle cannula 4120 to penetrate the atrial septum 4108. The outer cannula carriage 4158 and the middle cannula carriage 4166 may be configured to remain stationary relative to the dilator 4101 and the sheath 4102 because the distal end 4113 of the outer cannula 4110 abuts against the internal shoulder 4105 of the dilator 4101. The handle 4140 is displaced distally until the downward projection 4184 engages with the vertical stop 4163 and the gap 4164 remains between the middle cannula carriage 4166 and the outer cannula carriage 4158.

FIGS. 40A and 40B show the telescoping needle assembly 4000 in a middle cannula extending state. The distal end 4123 of the middle cannula 4120 extends beyond the distal end 4103 of the dilator 4101 by continued distal displacement of the handle 4140 by the clinician. A proximal end of the notch 4153 is configured to engage with a proximal end of the laterally extending portion of the middle cannula carriage 4166 and displace the middle cannula carriage 4166 distally while the outer cannula carriage 4158 remains stationary. Distal displacement of the middle cannula carriage 4166 results in closing of the gap 4164 and distal displacement of the middle cannula 4120 such that the distal end 4123 extends from the distal end 4103 of the dilator 4101 and at least partially through the atrial septum 4108.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A telescoping needle assembly, comprising:
   an outer cannula;
   a needle telescopically disposed within the outer cannula;
   a handle operatively coupled to the outer cannula and the needle, wherein the handle comprises a locking member configured to lock the needle in a retracted position; and
   a middle cannula telescopically disposed within the outer cannula, wherein the needle is telescopically disposed within the middle cannula,
   wherein when the locking member is displaced proximally, the locking member unlocks the needle from the retracted position and is configured to distally displace the needle and the middle cannula to an extending position, and
   wherein a distal portion of the needle and a distal portion of the middle cannula extend beyond a distal end of a dilator.

2. The telescoping needle assembly of claim 1, wherein distal ends of the outer and middle cannulae are blunt.

3. The telescoping needle assembly of claim 1, wherein a distal end of the needle is sharp.

4. The telescoping needle assembly of claim 1, wherein the outer cannula has an arcuate shape adjacent a distal end portion.

5. The telescoping needle assembly of claim 1, wherein the outer cannula comprises a spiral cut.

6. The telescoping needle assembly of claim 1, wherein the middle cannula comprises a spiral cut.

7. The telescoping needle assembly of claim 1, wherein when the needle is in the retracted position a distal end of the needle does not extend beyond a distal end of the outer cannula.

8. The telescoping needle assembly of claim 1, wherein when the needle is in the retracted position a distal end of the needle does not extend beyond a distal end of the middle cannula.

9. The telescoping needle assembly of claim 4, wherein a distal end of the needle is constrained away from a dilator lumen wall when the needle is inserted into a dilator lumen.

10. The telescoping needle assembly of claim 1, wherein the locking member is configured to axially displace the needle and the middle cannula to an extending position, and
    wherein a distal portion of the needle and a distal portion of the middle cannula extend beyond a distal end of a dilator.

11. The telescoping needle assembly of claim 1, wherein the handle is configured to axially displace the needle and the middle cannula to an extending position, and
    wherein a distal portion of the needle and a distal portion of the middle cannula extend beyond a distal end of a dilator.

12. The telescoping needle assembly of claim 1, wherein the locking member provides tactile and audible feedback when changing from a locked state to an unlocked state.

13. The telescoping needle assembly of claim 1, wherein the locking member comprises a resilient member configured to retain the locking member in a locked state.

14. A method of performing an atrial transseptal access, comprising:
   inserting a dilator and a sheath into a heart of a patient, wherein a distal end of the dilator is positioned against an atrial septum;
   obtaining a telescoping needle set, comprising: an outer cannula;
      a middle cannula telescopically disposed within the outer cannula; a needle telescopically disposed within the middle cannula; and
      a handle operatively coupled to the outer cannula, the middle cannula, and the needle;
   inserting the telescoping needle set into a lumen of the dilator, wherein the handle is configured to lock the needle in a retracted position, wherein a distal end of the needle is disposed within the middle cannula;
   unlocking the handle;
   advancing the needle through the atrial septum; and
   advancing a distal end of the middle cannula through the atrial septum.

15. The method of claim 14, wherein the handle comprises a locking member.

16. The method of claim 14, wherein the needle is advanced through the atrial septum by distal displacement of the handle.

17. The method of claim 15, wherein the needle is advanced through the atrial septum by distal displacement of the locking member.

18. The method of claim 15, wherein unlocking the handle comprises depressing the locking member.

19. A telescoping needle system, comprising: a dilator;
   a first elongate member;
   a second elongate member telescopically disposed within the first elongate member;
   a needle telescopically disposed within the second elongate member; and
   a handle operatively coupled to the first and second elongate members and the needle,
   wherein the handle comprises a locking member that is configured to lock the needle in a retracted position, wherein a sharp distal end of the needle is disposed within the second elongate member,
   wherein when the locking member is displaced proximally, the locking member unlocks the needle from the retracted position and is configured to distally displace the needle and the second elongate member to an extending position, and
   wherein a distal portion of the needle and a distal portion of the middle cannula extend beyond a distal end of a dilator.

20. The telescoping needle system of claim 19, wherein the sharp distal end of the needle is configured to not skive a lumen wall of the dilator when the needle is inserted into a lumen of the dilator.

21. The telescoping needle system of claim 19, wherein the handle is configured to advance the needle to the extending state.

* * * * *